US007824864B2

(12) United States Patent
Alving et al.

(10) Patent No.: US 7,824,864 B2
(45) Date of Patent: *Nov. 2, 2010

(54) DETECTION OF HUMAN ANTIBODIES TO SQUALENE IN SERUM

(75) Inventors: Carl R Alving, Bethesda, MD (US); Gary R Matyas, Olney, MD (US); Nabila M Wassef, Potomac, MD (US); Mangala Rao, Silver Spring, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 1199 days.

This patent is subject to a terminal disclaimer.

(21) Appl. No.: 11/030,330

(22) Filed: Jan. 7, 2005

(65) Prior Publication Data

US 2006/0160160 A1        Jul. 20, 2006

Related U.S. Application Data

(63) Continuation-in-part of application No. 09/859,389, filed on May 18, 2001, now Pat. No. 6,900,025.

(60) Provisional application No. 60/205,041, filed on May 18, 2000, provisional application No. 60/534,414, filed on Jan. 7, 2004.

(51) Int. Cl.
*G01N 33/53* (2006.01)

(52) U.S. Cl. .......................... 435/7.1; 435/7.2; 435/7.9; 435/7.92

(58) Field of Classification Search .................. 435/7.1, 435/7.2, 7.91, 7.52
See application file for complete search history.

(56) References Cited

U.S. PATENT DOCUMENTS

| 5,210,039 | A | * | 5/1993 | Cummins et al. | ............. 436/17 |
| 5,294,537 | A | * | 3/1994 | Batt | .......................... 435/7.32 |
| 5,419,904 | A | | 5/1995 | Irie | |
| 5,419,921 | A | | 5/1995 | Molacek et al. | |
| 5,709,879 | A | * | 1/1998 | Barchfeld et al. | ........... 424/450 |
| 6,166,050 | A | | 12/2000 | Lombardo et al. | |
| 6,191,108 | B1 | | 2/2001 | Rodkey et al. | |
| 6,214,566 | B1 | | 4/2001 | Asa et al. | |

FOREIGN PATENT DOCUMENTS

| WO | WO 95/00146 A1 | 1/1995 |
| WO | WO 98/20137 A1 | 5/1998 |
| WO | WO 01/87302 A1 | 11/2001 |

OTHER PUBLICATIONS

Harlow et al. "Antibodies a Laboratory Manual," Cold Spring Harbor, NY, Cold Spring Harbor Laboratory Press, 1988, p. 141-155.1.*
Applicant's filed affidavit & declaration in parent case (U.S. Appl. No. 09/859,389).*

Alving, C.R. et al., "Preparation and Use of Liposomes in Immunological Studies". In: G. Gregoriadis (Ed.) Liposome Technology, vol. 3 (Second Ed.), CRC Press, Inc. Boca Raton, p. 317-343, year 1993.
Mayes, P.A., "Cholesterol Synthesis, Transport, & Excretion", *Harper's Biochemistry*, 24th Edition, Appleton & Lang, Stamford, 1996, p. 271-283.
Schuster, B. et al., "Production of Antibodies Against Phosphocholine, Phosphatidylcholine, Sphingomyelin, and Lipid A by Injection of Liposomes Containing Lipid A", J. Immunol., 1979, vol. 122, No. 3, pp. 900-905.
Stollar, B.D. et al., "Cross-Reactions of Nucleic Acids With Monoclonal Antibodies to Phosphatidylinositol Phosphate and Cholesterol", Mol. Immunol., 1989, vol. 26, No. 1, pp. 73-79.
Swartz, Jr. G.M. et al., "Antibodies to Cholesterol", Proc. Natl. Acad. Sci. U.S.A., 1988, vol. 85, No. 6, pp. 1902-1906.
Wassef, N.M. et al, "Phosphate Binding Specificities of Monoclonal Antibodies Against Phosphoinositides in Liposomes", 1984, vol. 21, No. 10, pp. 863-868, Book Molecular Immunology.
Phillps, Christoper J., et al., "Antibodies to squalene in US Navy Persian Gulf War veterans with chronic multisympton illness," Vaccine, 2009, p. 391-3926, vol. 27.
Blanchard, Melvin S., et al., "Chronic Multisympton Illness Complex in Gulf War I Veterans 10 Years Later," American Journal of Epidemiology, 2006, p. 66-75, vol. 163, No. 1.
Bonhoeffer, Jan, et al., "Adverse events following immunization: perception and evidence," Curr Opin Infect Dis, 2007, p. 237-246, vol. 20.
Del Giudice, Giuseppe, et al., "Vaccines with the MF59 Adjuvant Do Not Stimulate Antibody Responses against Squalene," Olin. Vaccine Immunol., Sep. 2006, p. 1010-1013, vol. 13, No. 9.
Diaz-Torne, C., et al., "Abesence of Histologic Evidence of Synovitis in Patients With Gulf War Veterans' Illness With Joint Pain," Arthritis & Rheumatism, Oct. 15, 2007, p. 1316-1323, vol. 57, No. 7.
Ferguson, Eamonn, et al., "Theoretical accounts of Gulf War Syndrome: From environmental toxins to psychoneuroimmunology and neurdegeneration," Behavioural Neurology, 2001/2002, p. 133-147, vol. 13.
Fraser, Claire M., "A Genomics-Based Approach to Biodefence Preparedness," Nature Reviews, Jan. 2004, p. 23-33, vol. 5.
Fukasawa, Lucila O., "Adjuvant can improve protection induced by OMV vaccine against Neisseria meningitidis serogroups B/C in neonatal mice," FEMS Immunology and Medical Microbiology, 2004, p. 205-210, vol. 41.
Hannan, K. L., et al., et al., "Activation of the coagulation system in Gulf War Illness: a potential pathophysiologic link with chronic fatigue syndrome A laboratory approach to diagnosis," Blood Coagulation and Fibrinolysis, 2000, p. 673-678, vol. 11, No. 7.
Holm, Barbro C. et al., "Rats made congenic for Oia3 on chromosome 10 become susceptible to squalene-induced arthritis," Human Molecular Genetics, 2001, p. 565-575, vol. 10, No. 6.

(Continued)

*Primary Examiner*—Jacob Cheu
(74) *Attorney, Agent, or Firm*—Elizabeth Arwine

(57) ABSTRACT

The invention is a method and assay for detecting human squalene antibodies in sera or plasma using a blocking agent of −0.5% casein in a phosphate buffered saline (PBS) solution.

1 Claim, 25 Drawing Sheets

OTHER PUBLICATIONS

Hunt, Stephen C., et al., "Re: Chronic Multisympton Illness Complex in Gulf War I Veterans 10 Years Later," Am J Epidemiol, 2006, p. 706-710, vol. 164.

Kuroda, Yoshiki, et al., "Autoimmunity induced by adjuvant hydrocarbon oil components of vaccine," Biomedicine & Pharmacotheraphy, 2004, p. 325-337, vol. 58.

Little, Stephen F., Anthrax Vaccines A Development Update, Biodrugs, 2005, p. 233-245, vol. 19, No. 4.

Liu, Xiuping, et al., "The PorB porin from commensal Neisseria lactamica induces Th1 and Th2 immune responses to ovalbumin in mice and is a potential immune adjuvant," Vaccine, 2008, p. 786-796, vol. 26.

O'Bryan, Thomas A., MD, et al., "Human Leukocyte Antigens in Gulf War Veterans with Chronic Unexplained Multiple Symptoms," Military Medicine, 2003, p. 1015-1018, vol. 168, No. 12.

Petrik, Michael, S., et al., "Aluminum Adjuvant Linked to Gulf War Illness Induces Motor Neuron Death in Mice," NeuroMolecular Medicine, 2007, p. 83-100, vol. 9.

Richardson, Ralph D., et al., "Are Veterans Seeking Veterans Affairs' Primary Care as Healthy as Those Seeking Department of Defense Primary Care? A Look at Gulf War Veterans' Symptoms and Functional Status," Psychosomatic Medicine, 2002, p. 676-683, vol. 64.

Riedmann, Eva M., et al. "Bacterial ghosts as adjuvant particles," Expert Rev. Vaccines, 2007, p. 241-253, vol. 6. No. 2.

Schultze, Viola, et al., "Safety of MF59™ adjuvant," Vaccine, 2008, p. 3209-3222, vol. 26.

Smith, Tyler C., MS, et al., "The Postwar Hospitalization Experience of Gulf War Veterans Participating in U.S. Health Registries," J Occup Environ Med., 2004, p. 386-397, vol. 2004, No. 46.

Spanggord, Ronald J., et al., "Development and application of an analytical method for the determination of squalene in formulations of anthrax vaccine adsorbed," J. Pharm. Biomed. Anal. 2002, p. 183-93, vol. 29.

Staines, Donald, R., "Is osteoporosis linked to vaccinaitons and Gulf War Syndrome," Medical Hypotheses, 2004, p. 670-673, vol. 62.

Vasudev, Monica, MD, et al., "New-onset rheumatoid arthritis after anthrax vaccination," Ann Allergy Asthma Immunol., 2006, p. 110-112, vol. 97.

Wells, Timothy Steven, et al., "Military Hospitalizations Among Deployed US Service Members Following Anthrax Vaccination, 1998-2001," Human Vaccines, Mar./Apr. 2006, p. 54-59, vol. 2, No. 2.

"Annual Review of Cosmetic Ingredient Safety Assessments—2001/2002," International Journal of Toxicology, 2003, p. 1-35, vol. 22(Suppl. 1).

Fung et al., "3, 4-dicarboxylic Acid (A-87049): A Novel Potent Squalene Synthase Inhibitor", Journal of Medicinal Chemistry, 1997, vol. 40, No. 14, pp. 2123-2125.

Hanley et al., "Solubilization, Partial Purification, and Immunodetection of Squalene Synthetase From Tobacco Cell Suspension Cultures", Plant Physiology, 1992, vol. 98, No. 1, pp. 215-220.

Ryder, N.S. et al., "Interaction of Terbinafine with Human Serum and Serum Proteins", Journal of Medical and Veterinary Mycology, 1992, vol. 30, pp. 451-460.

Aggarwal, B.B. et al., "Human Lymphotoxin: Production by a Lymphoblastoid Cell Line, Purification, and Initial Characterization", J. Biol. Chem., 1984, vol. 259, No. 1, pp. 686-691.

Alving, C.R., "Natural Antibodies Against Phospholipids and Liposomes in Humans", Biochem. Soc. Trans., 1984, vol. 12, No. 2, pp. 342-344.

Alving, C.R. et al., Letters to the Editor, Exp. Mol. Pathol., 2000, vol. 68, pp. 196-198.

Alving, C.R. et al., "Naturally Occurring Antibodies to Cholesterol: A New Theory of LDL Cholesterol Metabolism", Immunol. Today, 1999, vol. 20, No. 8, pp. 362-366.

Alving, C.R. et al., "Antibodies to Cholesterol, Cholesterol Conjugates, and Liposomes: Implications for Atherosclerosis and Autoimmunity", Crit. Rev. Immunol., 1991, vol. 10, No. 5, pp. 441-453.

Alving et al., "Immunization with Cholesterol-Rich Liposomes Induces Anti-Cholesterol Antibodies and Reduces Diet-Induced Hypercholesterolemia and Plaque Formation", J. Lab. Clin. Med., 1996, vol. 127, No. 1, pp. 40-49.

Alving, C.R. et al., "Antibodies to Cholesterol: Biological Implications of Antibodies to Lipids", Curr. Top. Microbiol. Immunol., 1996, vol. 210, pp. 181-186.

Asa, P. et al., "Antibodies to Squalene in Gulf War Syndrome", Exp. Mol. Pathol., 2000, vol. 68, No. 1, pp. 55-64.

Asa, P.B. et al., "Antibodies to Squalene in Recipients of Anthrax Vaccine", Exp. Mol. Pathol., 2002, vol. 73, No. 1, pp. 19-27.

Aniagolu, J. et al., "Analysis of Anticholesterol Antibodies Using Hydrophobic Membranes", J. Immunol. Meth., 1995, vol. 182, No. 1, pp. 85-92.

Banerji, B. et al, "Anti-Liposome Antibodies Induced by Lipid A. I. Influences of Ceramide, Glycosphingolipids, and Phosphocholine on Complement Damage", J. Immunol., 1981, vol. 126, No. 3, pp. 1080-1084.

Beaumont, V. et al., "Antiestrogen Antibodies, Oral Contraception and Systemic Lupus Erythematosus", Clin. Physiol. Biochem., 1989, vol. 7, pp. 263-268.

Brochu, M. et al., "Monoclonal Antibodies for Use With 125-Iodine-Labeled Radioligands in Progesterone Radioimmunoassay", J. Steroid Biochem., 1984, vol. 21, No. 4, pp. 405-411.

Bucala, R. et al., "Anti-oestrogen Antibodies in Users of Oral Contraceptives and in Patients with Systemic Lupus Erythamatosus", Clin. Exp. Immunol., 1987, vol. 67, No. 1, pp. 167-175.

Counihan, K.A., et al., "Anti-estrogen Antibodies in Systemic Lupus Erythematosus: A Quantitative Evaluation of Serum Levels", Immuno. Invest., 1991, vol. 20, No. 3, pp. 317-331.

Cunningham, C.K. et al., "Safety of 2 Recombinant Human Immunodeficiency Virus Type 1 (HIV-1) Envelope Vaccines in Neonates Born to HIV-1-Infected Women", Clin. Infect. Dis., 2001, vol. 32, No. 5, pp. 801-807.

Dijkstra, J. et al., "Interaction of Anti-Cholesterol Antibodies with Human Lipoproteins", J. Immunol., 1996, vol. 157, No. 5, pp. 2006-2013.

Dorsam, H. et al., "Antibodies to Steroids From A Small Human Naive IgM Library", FEBS Lett., 1997, vol. 414, No. 1, pp. 7-13.

Drulak, M.W. et al., "Vaccination of Serpositive Subjects With CHIRON CMV gB Subunit Vaccine Combined With MF59 Adjuvant for Production of CMV Immune Globulin", Viral Immunol., 2000, vol. 13, No. 1, pp. 49-56.

Fahey, J.L. et al., "Proliferation and Differentiation of Lymphoid Cells: Studies With Human Lymphoid Cell Lines and Immunoglobulin Synthesis", Ann. N.Y. Acad. Sci., 1971, vol. 190, pp. 221-234.

Fantl, V.E. et al., Simultaneous Production of Monoclonal Antibodies to Dehydroepiandresterone, Oestradiol, Progesterone and Testosterone, J. Endocrinol., 1984, vol. 100, No. 3, pp. 367-376.

Franek, M., "Structural Aspects of Steroid-Antibody Specificity", J. Steroid Biochem., 1987, vol. 28, No. 1, pp. 95-108.

Fulco, C.E., et al., "Gulf War and Health: Depleted Uranium, Pyridostigmine Bromide, Sarin, Vaccines", National Academy Press, Washington, DC, 2000, vol. 1, p. 307.

Galfré, G. et al., "Preparation of Monoclonal Antibodies: Strategies and Procedures", Methods Enzymol., 1981, vol. 73, (Pt.B), pp. 3-46.

Gasparini, R. et al., "Increased Immunogenicity of the MF-59-adjuvanted Influenza Vaccine Compared to a Conventional Subunit Vaccine in Elderly Subjects", Eur. J. Epidemiol., 2001, vol. 17, No. 2, pp. 135-140.

Gigliotti, F., et al., "Reproducible Production of Protective Human Monoclonal Antibodies by Fusion of Peripheral Blood Lymphocytes With A Mouse Myeloma Cell Line", J. Infect. Dis., 1984, vol. 149, No. 1, pp. 43-47.

Granner, D.K., "Hormones of the Adrenal Cortex", In: R.K. Murray, et al. (Eds.) Harper's Biochemistry, 24$^{th}$ Edition, Appleton & Lang, Stamsord, p. 547-559, year 1996.

Grover, P.K. et al., "Specificity of Antisera to Sex Steroids I—The Effect of Substitution and Sterochemistry", J. Steroid Biochem., 1977, vol. 8, No. 2, pp. 121-126.

Gupta, R.K. et al., "Adjuvant Properties of Non-Phospholipid Liposomes (Novasomes® ) in Experimental Animals for Human Vaccine Antigens", Vaccine, 1996, vol. 14, No. 3, pp. 219-225.

Harro, C.D. et al., "Safety and Immunogenicity Trial in Adult Volunteers of Human Papillomavirus 16 L1 Virus-Like Particle Vaccine", J. Natl. Cancer Inst., 2001, vol. 93, No. 4, pp. 284-292.

Heineman, T.C. et al., "A Randomized, Controlled Study in Adults of the Immunogenicity of A Novel Hepatitis B Vaccine Containing MF59 Adjuvant", Vaccine, 1999, vol. 17, No. 22, pp. 2769-2778.

Kahn, J.O. et al., "Clinical and Immunologic Responses to Human Immunodeficiency Virus (HIV) Type $1_{SF2}$ gp120 Subunit Vaccine Combined With MF59 Adjuvant With or Without Muramyl Tripeptide Dipalmitoyl Phosphatidylethanolamine in Non-HIV-Infected Human Volunteers", J. Infect. Dis., 1994, vol. 170, No. 5, pp. 1288-1291.

Kester, K.E. et al., "Efficacy of Recombinant Circumsporozite Protein Vaccine Regimens Against Experimental *Plasmodium falciparum* Malaria", J. Infect. Dis., 2001, vol. 183, No. 4, pp. 640-647.

Köhler, G. et al., "Continuous Cultures of Fused Cells Secreting Antibody of Predefined Specificity", Nature, 1975, vol. 256, No. 5517, pp. 495-497.

Koivisto, P.V. et al., "Increased Amounts of Cholesterol Precursors in Lipoproteins After Ileal Exclusion", Lipids, 1988, vol. 23, No. 10, Abstract.

Kuwahara, A. et al., "Autoantibody Against Testosterone In A Woman With Hypergonadotropic Hypogonadism", J. Clin. Endocrin. Metab., 1998, vol. 83, No. 1, pp. 14-16.

Lohner, K. et al., "Squalene Promotes The Formation of Non-Bilayer Structures in Phospholipid Model Membranes", Biochem. Biophys. Acta., Year, vol. 1152, No. 1, pp. 69-77, year 1993.

Mais, D.E. et al., "Specific Interactions of Progestins and Anti-Progestins With Progesterone Antibodies, Plasma Binding Proteins and the Human Recombinant Receptor", J. Steroid Biochem. Molec. Biol., 1995, vol. 54, Nos. 1/2, pp. 63-69.

Matyas, G.R. et al., "Induction and Detection of Antibodies to Squalene", J. Immunol. Methods, 2000, vol. 245, Nos. 1/2, pp. 1-14.

Matyas, G.R. et al., "Induction and Detection of Antibodies to Squalene II. Optimization of the Assay for Murine Antibodies", J. Immunol. Methods, 2002, vol. 267, No. 2, pp. 119-129.

McFarland, E.J. et al., "Human Immunodeficiency Virus Type 1 (HIV-1) gp120-Specific Antibodies in Neonates Receiving an HIV-1 Recombinant gp120 Vaccine", Concise Comm., 2001, vol. 184, No. 10, pp. 1331-1335.

Miettinen, T.A., "Diurnal Variation of Cholesterol Precursors Squalene and Methyl Sterols in Human Plasma Lipoproteins", J. Lipid Res., 1982, vol. 23, No. 3, pp. 466-473.

Minutello, M. et al., "Safety and Immunogenicity of an Inactivated Subunit Influenza Virus Vaccine Combined With MF59 Adjuvant Emulsion in Elderly Subjects, Immunized for Three Consecutive Influenza Seasons", Vaccine, 1999, vol. 17, No. 2, pp. 99-104.

Mitchell, D.K. et al., "Immunogenicity of a Recombinant Human Cytomegalovirus gB Vaccine in Seronegative Toddlers", J. Pediatr. Infect. Dis., 2002, vol. 21, No. 2, pp. 133-138.

Moinuddin, A.A., "Binding of Naturally Occurring Anti-DNA Antibodies to Estradiol", Biochem. Mol. Biol. Int., 1998, vol. 45, No. 3, pp. 511-518.

Newhook, R. et al., "Exposure to Styrene in the General Canadian Population", IARC Sci. Pub., 1993, vol. 127, pp. 27-33.

Nicholson, K.G. et al., "Safety and Antigenicity of Non-Adjuvated and MF59-Adjuvanted Influenza A/Duck/Signapore/97 (H5N3) Vaccine: A Randomized Trial of Two Potential Vaccines Against H5N1 Influenza", Lancet, 2001, vol. 357, No. 9272, pp. 1937-1943.

Ott, G. et al., "The Adjuvant MF59: A 10-Year Perspective", *Meth. Mol. Med.*, Humana Press, 2000, vol. 42, pp. 211-228.

Pinto, M. et al., "Anti-Steroid Factor/s in Normal and Pathological Human Sera", Vox Sang, 1970, vol. 18, No. 2, pp. 155-162.

Pittman, P.R. et al., "Anthrax Vaccine: Short-term Safety Experience in Humans", Vaccine, 2002, vol. 20, Nos. 5-6, pp. 972-978.

Podda, A., "The Adjuvanted Influenza Vaccines With Novel Adjuvants: Experience With The MF59-Adjuvanted Vaccine", Vaccine, 2001, vol. 19, Nos. 17-19, pp. 2673-2680.

Relas, H. et al., "Fate of Intravenously Administered Squalene and Plant Sterols in Huamn Subjects", J. Lipid Res., 2001, vol. 42. No. 6, pp. 988-994.

Rickman, L.S. et al., "Use of Adjuvant Containing Mycobacterial Cell-Wall Skeleton, Monophosphoryl Lipid A., and Squalene in Malaria Circumsporozoite Protein Vaccine", Lancet, 1991, vol. 337, No. 8748, pp. 998-1001.

Schuster, B. et al., "Production of Antibodies Against Phosphocholine, Phosphatidylcholine, Sphingomyelin, and Lipid A By Injection of Liposomes Containing Lipid A", J. Immunol., 1979, vol. 122, No. 3, pp. 900-905.

Spanggord, R.J. et al., "Development and Application of an Analytical Method for the Determination of Squalene in Formulations of Anthrax Vaccine Adsorbed", J. Pharm. Biomed. Anal., 2002, vol. 29. No. 1-2, pp. 183-193.

Stewart, M.E., "Sebaceous Gland Lipids", Semin Dermatol., 1992, vol. 11. No. 2, Abstract.

Stoute, J.A. et al., "A Preliminary Evaluation of A Recombinant Circumsporozoite Protein Vaccine Against *Plasmodium falciparum* Malaria", New Engl. J. Med., 1997, vol. 336, No. 2, pp. 86-91.

Stoute, J.A. et al., "Long-Term Efficacy and Immune Responses Following Immunization With The RTS,S Malaria Vaccine", J. Infect. Dis., 1998, vol. 178, No. 4, pp. 1139-1144.

Teng, N.N.H. et al., "Protection Against Gram-Negative Bacteremia and Endotoxemia With Human Monoclonal IgM Antibodies", Proc. Natl. Acad. Sci. U.S.A., 1985, vol. 82, No. 6, pp. 1790-1794.

* cited by examiner

DETECTION OF HUMAN ANTIBODIES TO SQUALENE IN SERUM

This application is a continuation-in-part of U.S. application Ser. No. 09/859,389, filed May 18, 2001 now U.S. Pat. No. 6,900,025 which claims the benefit of U.S. Provisional Application Ser. No. 60/205,041, filed May 18, 2000 and this application claims the benefit of U.S. Provisional Application Ser. No. 60/534,414, filed Jan. 7, 2004.

I. STATEMENT REGARDING FEDERALLY SPONSORED RESEARCH

Not applicable.

II. FIELD OF THE INVENTION

This invention relates to an ELISA-based assay is described for the measurement of antibodies to squalene (SQE) in human serum and plasma.

III. BACKGROUND OF THE INVENTION

Squalene (SQE) is a triterpenoid hydrocarbon oil, $C_{30}H_{50}$, that is widely produced by both plants and animals, and is present in human food. In humans, SQE serves a as precursor in the synthesis of cholesterol and all of the steroid hormones (Mayes, 1996; Granner, 1996) (FIG. 1). Both SQE and cholesterol are transported in the blood on very low density lipoproteins (VLDL) and low density lipoproteins (LDL) (Miettinen, 1982; Koivisto and Miettinen, 1988). Squalene and cholesterol are also synthesized in the liver and in the epidermis of the skin where SQE comprises a large amount of the oil secreted by sebaceous glands (Stewart, 1992) Because it is a naturally occurring biodegradable oil, SQE, and its hydrogenated derivative squalane, each has been proposed as the oil component of oil-in-water emulsions to be used as new adjuvants for vaccines.

Although not included in any vaccines licensed in the United States, a SQE—containing emulsion is part of an influenza vaccine licensed in Italy and has been given without adverse effects to hundreds of thousands of people (Podda, 2001; Ott et al., 2000). Numerous other human clinical trials for influenza (Ott et al., 2000; Nicholson et al., 2001; Gasparini et al., 2001), cytomegalovirus (Drulak et al., 2000), hepatitis B (Heineman et al., 1999), papillomavirus (Harro et al., 2001), HIV (Kahn et al., 1994; Mitchell et al., 2002; McFarland et al., 2001; Cunningham et al., 2001), and malaria (Stoute et al., 1997; Stoute et al., 1998; Kester et al., 2001; Rickman et al., 1991) have used SQE emulsions. Vaccine reactions were typically mild. However, some moderate to severe reactions, that can be attributed to other adjuvants in the formulations, were reported (Kahn et al., 1994; Rickman et al., 1991; Stoute et al., 1997; Kester et al., 2001). Furthermore, no adverse reactions were reported following intravenous injection of humans with chylomicron-like lipid emulsions containing SQE (Relas et al., 2001).

IV. REFERENCES

Aggarwal, B. B., Moffat, B., Harkins, R. N., 1984. Human lymphotoxin: production by a lymphoblastoid cell line, purification, and initial characterization. J. Biol. Chem. 259, 686.

Alving, C. R. 1986. Alving, C. R., 1984. Natural antibodies against phospholipids and liposomes in humans. Biochem. Soc. Trans. 12, 342.

Alving, C. R., Grabenstein, J. D., 2000. Letters to the editor. Exp. Mol. Pathol. 68, 196.

Alving, C. R., Wassef, N. M., 1999. Naturally occurring antibodies to cholesterol: a new theory of LDL cholesterol metabolism. Immunol. Today 20, 362.

Alving, C. R., Swartz Jr., G. M., Wassef, N. M. 1989. Naturally occurring autoantibodies to cholesterol in humans. Biochem. Soc. Trans. 17, 637. Chem. Phys. Lipids 40, 303.

Alving, C. R., Swartz, Jr., G. M. 1991. Antibodies to Cholesterol, Cholesterol Conjugates, and Liposomes: Implications for Atherosclerosis and Autoimmunity. Crit. Rev. Immunol. 10, 441.

Alving, C. R., Shichijo, S., Mattsby-Baltzer, I., Richards, R. L., Wassef, N. M. 1993. Preparation and use of liposomes in immunological studies. In: G. Gregoriadis (Ed.) Liposome Technology, vol. 3, (Second Edition), CRC Press, Inc., Boca Raton, p. 317.

Alving, C. R., Swartz, Jr. G. M., Wassef, N. M., Ribas, J. L., Herderick, E. E., Virmani, R., Kolodgie, F. D., Matyas, G. R., Cornhill, J. F. 1996. Immunization With Cholesterol-Rich Liposomes Induces Anti-Cholesterol Antibodies and Reduces Diet-Induced Hypercholesterolemia And Plaque Formation. J. Lab. Clin. Med. 127, 40.

Alving, C. R., Wassef, N. M., Potter, M. 1996. Antibodies To Cholesterol: Biological Implications of Antibodies To Lipids. Curr. Topics Microbiol. Immunol. 210, 181.

Asa, P., Cao, Y., Garry, R. F. Antibodies to squalene in gulf war syndrome. 2000. Exp. Mol. Path. 68, 55.

Asa, P. B., Wilson, R. B., Garry, R. F., 2002. Antibodies to Squalene in Recipients of Anthrax Vaccine. Exp. Mol. Pathol. 73, 19.

Aniagolu, J., Swartz, Jr., G. M., Dijkstra, J., Madsen, J. W., Raney, J. J., Green, S. J. 1995. Analysis of Anticholesterol Antibodies Using Hydrophobic Membranes. J. Immunol. Meth. 182, 85.

Banerji, B., Alving, C. R. 1981. Anti-Liposome Antibodies Induced By Lipid A. I. Influences Of Ceramide, Glycosphingolipids, and Phosphocholine On Complement Damage. J. Immunol. 126, 1080.

Beaumont, V., Gioud-Paquet, M., Kahn, M. F., Beaumont, J. L., 1989. Antiestrogen Antibodies, Oral Contraception and Systemic Lupus Erythematosus. Clin. Physiol. Biochem. 7, 263.

Brochu, M., Veilleux, R., Lorrain, A., Belanger, A., 1984. Mono-Clonal Antibodies for Use with 125-Iodine-Labeled Radioligands in Progesterone Radioimmunoassay. J. Steroid Biochem. 21, 405.

Bucala, R., Lahita, R. G., Fishman, J., Cerami, A., 1987. Anti-Oestrogen Antibodies in Users of Oral Contraceptives and in Patients With Systemic Lupus Erythamatosus. 67, 167.

Counihan, K. A., Vertosick, F. T., Kelly, R. H., 1991. Anti-Estrogen Antibodies In Systemic Lupus Erythematosus: A Quantitative Evaluation Of Serum Levels. Immunol. Invest. 20, 317.

Cunningham, C. K., Wara, D. W., Kang, M., Fenton, T., Hawkins, E., Mcnamara, J., Mofenson, L., Duliege, A. M., Francis, D., Mcfarland, E. J., Borkowsky, W. Pediatric AIDS Clinical Trials Group 230 Collaborators, 2001. Safety Of 2 Recombinant Human Immunodeficiency Virus Type 1 (HIV-1) Envelope Vaccines In Neonates Born To HIV-1-Infected Women. Clin. Infect. Dis. 32, 801.

Dijkstra, J., Swartz, Jr., G. M, Raney, J. J., Aniagolu, J., Toro, L., Nacy, C. A., Green, S. J. 1996. Interaction Of Anti-Cholesterol Antibodies With Human Lipoproteins. J. Immunol. 157, 2006.

Do Rsam, H., Rohrabach, P., Ku Rschner, T., Kipriyanov, S., Renner, Braunagel, M., Welschof, M., Little, M., 1997. Antibodies To Steroids From A Small Human Naive Igm Library. FEBS Lett. 414, 7.

Drulak, M. W., Malinoski, F. J., Fuller, S. A., Stewart, S. S., Hoskin, S., Duliege, A.-M., Sekulovich, R., Burke, R., Winston, S., 2000. Vaccination Of Serpositive Subjects With CHIRON CMV Gb Subunit Vaccine Combined With MF59 Adjuvant For Production Of CMV Immune Globulin. Viral Immunol. 13, 49.

Fahey, J. L., Buell, D. N., Sox, H. C., 1971. Proliferation And Differentiation Of Lymphoid Cells: Studies With Human Lymphoid Cell Lines And Immunoglobulin Synthesis. Ann. N.Y. Acad. Sci. 190, 221.

Fantl, V. E., Wang, D. Y., 1984. Simultaneous Production Of Mono-Clonal Antibodies To Dehydroepiandresterone, Oestradiol, Progesterone And Testosterone. J. Endocrinol. 100, 367.

Franek, M., 1987. Structural Aspects Of Steroid-Antibody Specificity. J. Steroid Biochem. 28, 95.

Fulco, C. E., Liverman, C. T., Sox, H. C., 2000. Gulf War And Health: Depleted Uranium, Pyridostigmine Bromide, Sarin, Vaccines, Vol. 1. National Academy Press, Washington, D.C., P. 307.

Galfré, G., Milstein, C. 1981. Monoclonal Antibodies: Strategies And Procedures. Meth. Enzymol. 73, 3.

Gasparini, R., Pozzi, T., Montomoli, E., Fragapane, E., Senatore, F., Minutello, Podda, A., 2001. Increased Immunogenicity Of The MF-59-Adjuvanted Influenza Vaccine Compared To A Convention-Al Subunit Vaccine In Elderly Subjects. Eur. J. Epidemiol. 17, 135.

Gigliotti, F., Smith, L., Insel, R. A., 1984. Reproducible Production Of Protective Human Monoclonal Antibodies By Fusion Of Peripheral Blood Lymphocytes With A Mouse Myeloma Cell Line. J. Infect. Dis. 149, 43.

Granner, D. K. 1996. Hormones Of The Adrenal Cortex. In: R. K. Murray, D. K. Granner, P. A. Mayes And V. W. Rodwell (Eds.) Harper's Biochemistry, $24^{th}$ Edition, Appleton & Lang, Stamsord, P. 547.

Grover, P. K., Odell, W. D., 1977. Specificity Of Antisera To Sex Steroids I—The Effect Of Substitution And Sterochemistry. J. Steroid Biochem. 8, 121.

Gupta, R. K., Varanelli, C. L., Griffin, P., Wallach, D. F. H., Siber, G. R. 1996. Adjuvant Properties Of Non-Phospholipid Liposomes (Novasomes®) In Experimental Animals For Human Vaccine Antigens. Vaccine 14, 219.

Harro, C. D., Pang, Y.-Y. S., Roden, R. B. S., Hildesheim, A., Wang, Z., Reynolds, M. J., Mast, T. C., Robinson, R., Murphy, B. R., Karron, R. A., Dilner, J., Schiller, J. T., Lowy, D. R., 2001. Safety And Immunogenicity Trial In Adult Volunteers Of Human Papillomavirus 16 L1 Virus-Like Particle Vaccine. J. Natl. Cancer Inst. 93, 284.

Heineman, T. C., Clements-Mann, M. L., Poland, G. A., Jacobson, R. M., Izu, A. E., Sakamoto, D., Eiden, J., Van Nest, G. A., Hsu, H. H., 1999. A Randomized Controlled Study In Adults Of The Immunogenicity Of A Novel Hepatitis B Vaccine Containing MF59 Adjuvant. Vaccine 17, 2769.

Irie, R. F., 1995. Human B-Lymphoblastoid Cell Line Secreting Antiganglioside Antibody. U.S. Pat. No. 5,419,921.

Kahn, J. O., Sinangil, F., Baenziger, J., Murcar, N., Wynne, D., Coleman, R. L., Steiner, K. S., Dekker, C. L., Chernoff, D., 1994. Clinical And Immunologic Responses To Human Immunodeficiency Virus (HIV) Type $^1$S F 2 Gp120 Subunit Vaccine Combined With MF59 Adjuvant With Or Without Muramyl Tripeptide Dipalmitoyl Phosphatidylethanolamine In Non-HIV Infected Human Volunteers. J. Infect. Dis. 170, 1288.

Kester, K. E., Mckinney, D. A., Tornieporth, N., Ockenhouse, C. F., Heppner, D. G., Hall, T., Krzych, U., Delchambre, M., Voss, G., Dowler, M. G., Palensky, J., Wittes, J., Cohen, J., Ballou, W. R., 2001. Efficacy Of Recombinant Circumsporozite Protein Vaccine Regimens Against Experimental Plasmodium Falciparum Malaria. J. Infect. Dis. 183, 640.

Köhler, G., Milstein, C., 1975. Continuous Cultures Of Fused Cells Secreting Antibody Of Predefined Specificity. Nature 256, 495.

Koivisto, P. V. I., Miettinen, T. A., 1988. Increased Amount Of Cholesterol Precursors In Lipoprotein After heal Exclusion. Lipids 23, 993.

Kuwahara, A., Kamada, M., Irahara, M., Naka, O., Yamashita, T., Aono, T., 1998. Autoantibody Against Testosterone In A Woman With Hypergonadotropic Hypogonadism. J. Clin. Endocrinol. Metab. 83, 14.

Larrick, J. W., Raubitschek, A. R., Truitt, K. E., 1986. Human Lymphoblastold Cell Line And Hybridoma Derived Thereform. U.S. Pat. No. 4,624,921.

Lohner, K., Degovics, G., Laggner, P., Gnamusch, E., Paltauf, F. 1993. Squalene Promotes The Formation Of Non-Bilayer Structures In Phospholipid Model Membranes. Biochim. Biophys. Acta 1152, 69.

Mais, D. E., Hayes, J. S., Heap, R. B., Wang, M.-W., 1995. Specific Interactions Of Progestins And Anti-Progestins With Progesterone Antibodies, Plasma Binding Proteins And The Human Recombinant Receptor. J. Steroid Biochem. Mol. Biol. 54, 63.

Matyas, G. R., Wassef, N. M., Rao, M., Alving, C. R., 2000. Induction And Detection Of Antibodies To Squalene. J. Immunol. Methods 245, 1.

Matyas, G. R., Rao, M., Alving, C. R., 2002. Induction And Detection Of Antibodies To Squalene II. Optimization Of The Assay For Murine Antibodies. J. Immunol. Methods 267, 119.

Mayes, P. A. 1996. Cholesterol Synthesis, Transport, & Excretion. In: R. K. Murray, D. K. Granner, P. A. Mayes And V. W. Rodwell (Eds.) Harper's Biochemistry, $24^{th}$ Edition, Appleton & Lang, Stamsord, P. 271.

Mcfarland, E. J., Borkowsky, W., Fenton, T., Wara, D., Mcnamara, J., Samson, P., Kang, M., Mofenson, L., Cunningham, C., Duliege, A.-M., Sinangil, F., Spector, S. A., Jimenez, E., Bryson, Y., Burchett, S., Frankel, L. M., Yogev, R., Giglitotti, K., Luzuriaga, K., Livingston, R. A. The AIDS Clinical Trials Group 230 Collaborators, 2001. Human Immunodeficiency Virus Type 1 (HIV-1) Gpl 20-Specific Antibodies In Neonates Receiving An HIV-1 Recombinant Gp120 Vaccine. J. Infect. Dis. 184, 1331.

Metcalf, J., 2000. Http://www.House.Gov/Metcalf/Report.Htm, Appendix 25.

Miettinen, T. A. 1982. Diurnal Variation Of Cholesterol Precursors Squalene And Methyl Sterols In Human Plasma Lipoproteins. J. Lipid Res. 23, 466.

Minutello, M., Senatore, F., Cecchinelli, G., Bianchi, M., Andreani, T., Podda, A., Crovari, P. 1999. Safety And Immunogenicity Of An Inactivated Subunit Influenza Virus Vaccine Combined With MF59 Adjuvant Emulsion In Elderly Subjects, Immunized For Three Consecutive Influenza Seasons. Vaccine 17, 99.

Mitchell, D. K., Holmes, S. J., Burke, R. L., Duliege, A. M., Adler, S. P., 2002. Immunogenicity Of A Recombinant Human Cytomegalovirus Gb Vaccine In Seronegative Toddlers. Pediatr. Infect. Dis. 21, 133.

Moinuddin, Ali, A., 1998. Binding Of Naturally Occurring Anti-DNA Antibodies To Estradiol. Biochem. Mol. Biol. Int. 45, 511.

Newhook, R., Caldwell, I., 1993. Exposure To Styrene In The General Canadian Population. IARC Sci. Publ. 127, 27.

Nicholson, K. G., Colegate, A. E., Podda, A., Stephenson, I., Wood, Ypma, E., Zambon, M. C., 2001. Safety And Antigenicity Of Non-Adjuvanted And MF-59-Adjuvanted Influenza A/Duck/Singpore 97 (H5N3) Vaccine: A Randomized Trial Of Two Potential Vaccines Against H5N1 Influenza. Lancet 357, 1937.

Ott, G., Radhakrishnan, R., Fant, J., Hora, M., 2000. The Adjuvant MF59: A 10 Year Perspective. In: O'Hagan, D. T. (Ed.), Vaccine Adjuvants: Preparation Methods And Research Protocols. Meth. Mol. Med., Vol. 42. Humana Press, Totowa, P. 211.

Pinto, M., Rimon, A., 1970. Anti-Steroid Factor/S In Normal And Pathological Human Sera. Vox Sang. 18, 155.

Pittman, P. R., Gibbs, P. H., Cannon, T. L., Friedlander, A. M., 2002. Anthrax Vaccine: Short-Term Safety Experience In Humans. Vaccine 20, 972.

Podda, A., 2001. The Adjuvanted Influenza Vaccines With Novel Adjuvants: Experience With The MF59-Adjuvanted Vaccine. Vaccine 19, 2673.

Relas, H., Gylling, H., Miettinen, T. A., 2001. Fate Of Intravenously Administered Squalene And Plant Sterols In Human Subjects. J. Lipid Res. 42, 988.

Rickman, L. S., Gordon, D. M., Wistar Jr., R., Krzych, U., Gross, M., Hollingdale, M. R., Egan, J. E., Chulay, J. D., Hoffman, S. L. 1991. Use Of Adjuvant Containing Mycobacterial Cell-Wall Skeleton, Monophosphoryl Lipid A, And Squalene In Malaria Circumsporozite Protein Vaccine. Lancet 337, 998.

Schuster, B., Neidig, M., Alving, B. M., Alving, C. R. 1979. Production Of Antibodies Against Phosphocholine, Phosphatidylcholine, Sphingomyelin, And Lipid A By Injection Of Liposomes Containing Lipid A. J. Immunol. 122, 900.

Spanggord, R. J., Wu, B., Sun, M., Lim, P., Elis, W. Y., 2002. Development And Application Of An Analytical Method For The Determination Of Squalene In Formulations Of Anthrax Vaccine Adsorbed. J. Pharm. Biomed. Anal. 29, 183.

Stewart, M. E., 1992. Sebaceous Gland Lipids. Semin. Dermatol. 11, 100.

Stollar, B. D., Mcinerney, T., Gavron, T., Wassef, N. M., Swartz, G. M., Jr., Alving, C. R. 1989. Cross-Reactions Of Nucleic Acids With Monoclonal Antibodies To Phosphatidylinositol Phosphate And Cholesterol. Mol. Immunol. 26, 73.

Stoute, J. A., Slaoui, M., Heppner, G., Momin, P., Kester, K. E., Desmons, P., Wellde, G. T., Garcon, N., Krzych, U., Marchand, M., Ballou, W. R., Cohen, J. D., 1997. A Preliminary Evaluation Of A Recombinant Circumsporozoite Protein Vaccine Against Plasmodium Falciparum Malaria. New Engl. J. Med. 336, 86.

Stoute, J. A., Kester, K. E., Krzych, U., Welide, B. T., Hall, T., White, Glenn, G., Ockenhouse, C. F., Garcon, N., Schwenk, R., Lanar, D. E., Sun, P., Momin, P., Wirtz, R. A., Golenda, C., Slaoui, M., Wortmann, G., Holland, C., Dowler, M., Cohen, J., Ballou, W. R., 1998. Long-Term Efficacy And Immune Responses Following Immunization With The RTS,S Malaria Vaccine. J. Infect. Dis. 178, 1139.

Swartz, Jr., G. M., Gentry, M. K., Amende, L. M., Blanchette-Mackie, E. J., Alving, C. R. 1988. Antibodies To Cholesterol. Proc. Natl. Acad. Sci. U.S.A. 85, 1902.

Teng, N. N. H., Kaplan, H. S., Herbert, J. M., Morre, C., Douglas, H., Wunderlibh, A., Braude, A. I., 1985. Protection Against Gram-Negative Bacteremia And Endotoxemia With Human Monoclonal Igm Antibodies. Proc. Natl. Acad. Sci. U. S. A. 82, 1790.

Wassef, N. M., Roerdink, F., Swartz, Jr., G. M., Lyon, J. A., Berson, B. J., Alving, C. R. 1984. Phosphate Binding Specificities Of Monoclonal Antibodies Against Phosphoinositides In Liposomes. Mol. Immunol. 21 863.

V. SUMMARY OF THE INVENTION

It is an object of this invention to advance the state of the art in connection with detection and methods arising therefrom in connection with human squalene antibodies.

It is an object of this invention to provide a method for detection of and assay for human squalene antibodies.

It is an object of this invention to minimize undersirable interference from non-target moieties in the detection of human antibodies to squalene.

These and other objects are satisfied by a method for detecting the presence of human squalene antibodies capable of specific binding with squalene, comprising the steps of: providing a solid support suitable for allowing specific binding of squalene with human squalene antibodies; immobilizing squalene on the solid support; washing the immobilized squalene with blocking agent; contacting the immobilized squalene with a sample containing human squalene antibodies or fragments thereof capable of specific binding with squalene; allowing the squalene antibodies to specifically bind to the immobilized squalene to form a specific antibody complex; contacting the antibody complex with a ligand that specifically binds to the complex; contacting the ligand with an indicator agent; and detecting the indicator agent.

Still other objects are satisfied by a method for detecting the presence of squalene antibodies in human sera comprising the step of using an ELISA protocol using 0.5% casein as a blocking agent.

Further stated objects are satisfied by an assay kit for detecting human antibody to squalene induced by injection of squalene, comprising: a solid support suitable for immobilizing human squalene antibodies; a blocking agent comprising casein; a diluent comprising Phosphate Buffered Saline; a ligand capable of forming a complex with the blocked antibodies to form a terneiary complex therewith; and an detectable indicator agent capable of binding to the terniary complex.

The present invention builds on and comprises an improvement to the original assay described in the earlier above-reference '389 application. That assay used 96 well plates containing hydrophobic PVDF membranes. The assay was highly reproducible, but was very labor intensive. The new assay herein utilized 96 well polystyrene tissue culture plates (Matyas et al., 2002). The new assay provides a high throughput capacity, is reproducible and quantitative, and has increased sensitivity. The invention herein is directed to this latter assay for the measurement of human antibodies to SQE. The experimental data has been developed from cohorts of nonselected military and civilian populations, and in populations selected for their exposure to numerous vaccines, including AVA.

To develop the highly reliable assay for antibodies to SQE as described below, murine monoclonal antibodies to SQE were made to serve as positive controls [Matyas, et al., "Induction and Detection of Antibodies to Squalene," *J. Immunol. Meth.* 245:1 (2000)]. These monoclonal antibodies were used to develop an assay for measuring antibodies to squalene in human serum.

The improvement to the prior ELISA-based assay is that it measures antibodies to squalene (SQE) in human serum and plasma. This improved assay was adapted from the previously described assay for murine antibodies to SQE (Matyas et al., 2002. J. Immunol. Methods 267, 119). Like the murine SQE antibody assay, the human antibody assay used sterile cell culture 96-well plates coated with SQE (20 nmol/well). Phosphate-buffered saline (PBS)-0.5% casein was used as both a blocking agent and dilution buffer. The assay has a high through-put capacity and is reproducible and quantitative.

This improved assay for human antibody detection was used to evaluate samples from three different human cohorts. The first cohort was retired employees of the United States Army Medical Research Institute of Infectious Diseases (US-AMRIID alumni). The mean age was 68; (N=40; range 58-82). Most were vaccinated with the U.S. licensed anthrax vaccine (AVA) and most had received several other vaccines through a USAMRIID special immunization program. The second cohort was of similar age (N=372; mean age 67; range 54-97) from the normal population of Frederick, Md. and were not vaccinated with AVA. The third cohort (N=299) was from Camp Memorial Blood Center, United States Army Medical Department Activities, Fort Knox, Ky. (No additional volunteer information is available).

Using this new ELISA method, antibodies to SQE were detected in all three of the cohorts. IgG antibodies to SQE were detected in 7.5% and 15.1% of the samples from the USAMRIID alumni and Frederick cohorts, respectively. These differences were not significantly different ($?_1$)=1.69, p=0.19). In contrast, no IgG antibodies to SQE were detected in the Fort Knox cohort which is significantly different than the Frederick cohort ($?_1$)=49.25, p<0.0001). IgM antibodies to SQE were detected in 37.5% and 32.3% of the samples from the USAMRIID and Frederick cohorts, respectively, but there was no significant difference between the cohorts. In the Fort Knox cohort, 19.4% of the samples were positive for IgM antibodies to SQE, which was significantly different from the Frederick cohort ($?_1$)=14.23, p=0.0002). Although the age of the volunteers from the Fort Knox cohort is unknown, the demographic of the donors at the blood bank volunteers is 85% 17-21 years of age. This suggested that the prevalence of antibodies to SQE may increase with age. This was confirmed with mouse studies in which the presence of antibodies was monitored as a function of time. No antibodies to SQE were detected in female BALB/c, B10.Br and C57BL/6 mice at 2 months of age, but they reached a maximum prevalence with 100% and 89% of animals testing positive for IgG and IgM antibodies to SQE, respectively, in the C57BL/6 mice at 18 months of age. BALB/c and B10.Br mice also developed antibodies to SQE over time, but were at a lower prevalence than those observed in the C57BL/6 mice.

Thirty-five of the 40 volunteers in the USAMRIID were vaccinated with AVA (mean no. doses=26; range 3-47). Comparison of the prevalence of antibodies to SQE from the AVA immunized group with the Frederick cohort revealed that there was no statistical differences for IgG ($?_1$)=2.3, p=0.13) or IgM ($?$,=0.33, p=0.56). When the data from the USAMRIID and Frederick cohorts were combined and analyzed for the presence of antibodies to SQE with respect to the sex of the volunteer, females (40.8%) were found to have a higher prevalence of IgM antibodies to SQE than men (28.4%) ($?_1$=6.59, p=0.01). No significant difference was observed in the prevalence for IgG antibodies to SQE in females (17.7%) and males (12.5%). We conclude that antibodies to SQE occur naturally in humans; have an increased prevalence in females; are not correlated with vaccination with AVA; and appear to increase in prevalence with age.

In summary, the invention herein describes a highly reproducible, high throughput, and quantitative assay for measuring antibodies to SQE in human serum. Using this newly developed assay, both naturally occurring IgG and IgM antibodies to SQE are observed in human serum. The antibody titers are generally low and, notably, there is an increased prevalence of antibodies to SQE in serum from females as compared to males. No correlation appears to exist between the presence of antibodies to SQE and previous immunization with AVA and the results indicate that the prevalence of antibodies to SQE in human serum increases with the age of the volunteer. Longitudinal studies in three different strains of mice confirmed the presence of naturally occurring IgG and IgM antibodies to SQE and the prevalence of antibodies to SQE increased with the age of the mice.

In the following description, reference is made to the accompanying drawing, and which is shown by way of illustration to the specific embodiments in which the invention may be practiced. The following illustrated embodiments are described in sufficient detail to enable those skilled in the art to practice the invention. It is to be understood that other embodiments may be utilized and that changes based on presently known structural and/or functional equivalents may be made without departing from the scope of the invention.

Given the following detailed description, it should become apparent to the person having ordinary skill in the art that the invention herein provides a novel detection method for human antibodies to squalene.

VI. DESCRIPTION OF THE DRAWINGS

FIG. 1 shows the structure of squalene, cholesterol and polystyrene.

FIG. 2 shows the binding activity of mouse serum IgM to SQE by ELISA. Mice were immunized biweekly with: A) Liposomes containing lipid A as an adjuvant and composed of DMPC/DMPG/SQE in a molar ratio of 9:1:2.5 (group 4); or B) an emulsion containing of 20% SQE, 5% Tween 80, 5% Span 85 and lipid A (group 6); or C) the above liposomes containing lipid A as an additional adjuvant. Serum obtained from these mice were tested by ELISA as described in the Materials and Methods. Polystyrene "U" bottom plates were coated with 10 μg/well of SQE in ethanol. Binding activity of the indicated dilutions of preimmune and immune serum was assayed at the indicated time points. Results are presented as the mean absorbance from triplicate wells containing squalene subtracted from the absorbance of triplicate wells lacking squalene±SD.

FIG. 3 shows the end point dilution IgM titers of immune mouse serum against SQE, and liposomes containing or lacking SQE. Serum from mice immunized biweekly with liposomes containing lipid A as an additional adjuvant and composed of DMPC/DMPG/SQE in a molar ratio of 9:1:2.5 (group 4) were tested by ELISA. Capture antigens for the assay consisted of SQE or of liposomes containing or lacking squalene. Polystyrene "U" bottom plates were coated with 10 μg/well of SQE in ethanol, or with the equivalent amount of L(SQE), or with the equivalent amount of L. The results shown were obtained by subtracting the absorbance of triplicate wells containing the appropriate capture antigen from the absorbance of triplicate wells lacking antigens. Endpoint IgM antibody titers were calculated from the highest dilution of serum giving twice the absorbance of the background.

FIG. 4 shows the comparative binding of a mAb to SQE or SQA coated on PVDF or PS flat bottom plates. Each well contained 10 μg of SQA or SQE dissolved in 0.1 ml of isopropanol, or isopropanol alone (control), as appropriate, at the concentrations indicated. The culture supernatant of a mAb was diluted in PBS-4% fetal bovine serum (PVDF plates) or PBS-0.3% gelatin (PS plates). ELISAs were performed as described in the Methods section for the PVDF (poly vinylidenefloride) and PS plates, respectively. Similar results were observed with 8 other clones. Values are the mean±standard deviation of triplicate wells.

Figure 7:
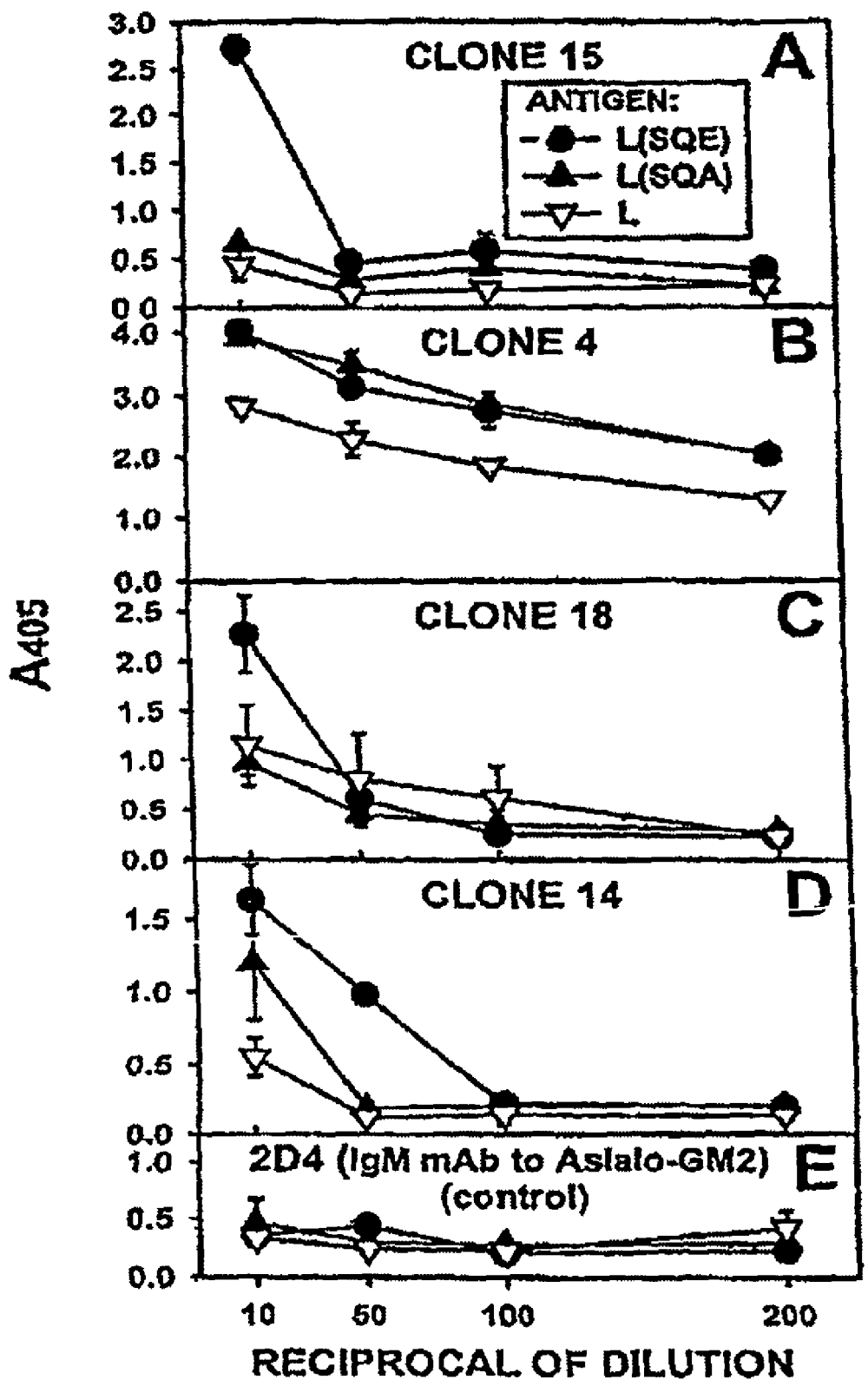

FIG. 7 shows the reactivity of monoclonal antibodies to liposomes containing or lacking SQE or SQA. L(SQE), L(SQA) and L (33 nmol of phospholipid) in 0.05 ml of PBS was placed in each well of a PS (polystyrene) "U" bottom plate. The plates were processed as described in the Methods. Culture supernatants from the indicated clones were diluted in PBS-0.3% gelatin and 0.05 ml was placed in each well. Values are the mean±standard deviation of triplicate wells. A, B, C, D: Binding of the indicated culture supernatants to L(SQE), L(SQA), and L. E: Negative controls consisting of binding of an irrelevant IgM secreting clone 2D4 (IgM anti-$G_{M2}$).

Figure 8:
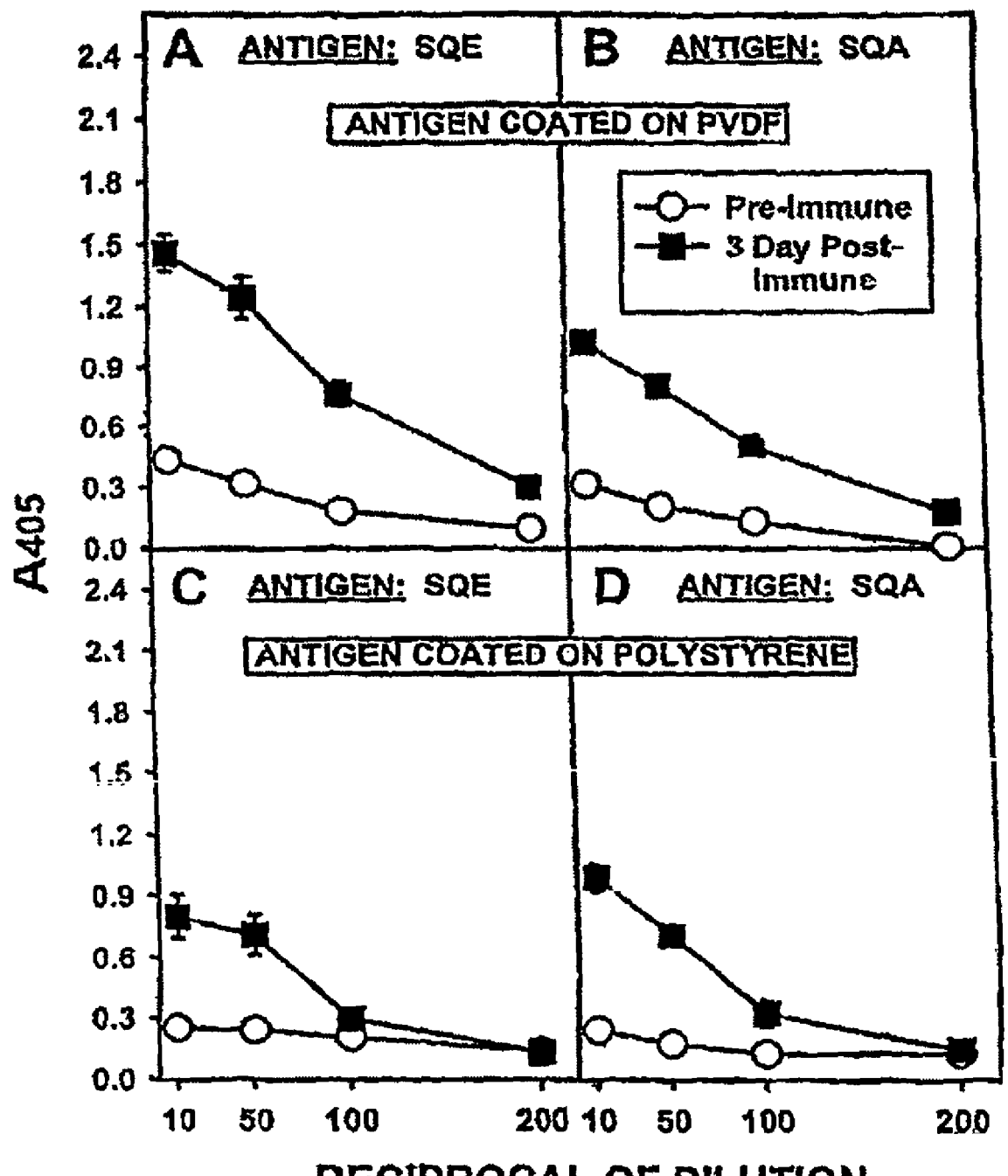

FIG. 8 shows the binding of serum IgM to SQE and SQA on PVDF and PS flat bottom ELISA plates. Pre-immune or 3 day post-immune serum from mice immunized with liposomes containing 71% SQE was diluted in PBS-4% fetal bovine serum (PVDF plates) or PBS-0.3% gelatin (PS plates). ELISAs were performed as described in the Methods section for the PVDF and PS plates, respectively. Values are the mean±standard deviation of triplicate wells.

Figure 9:
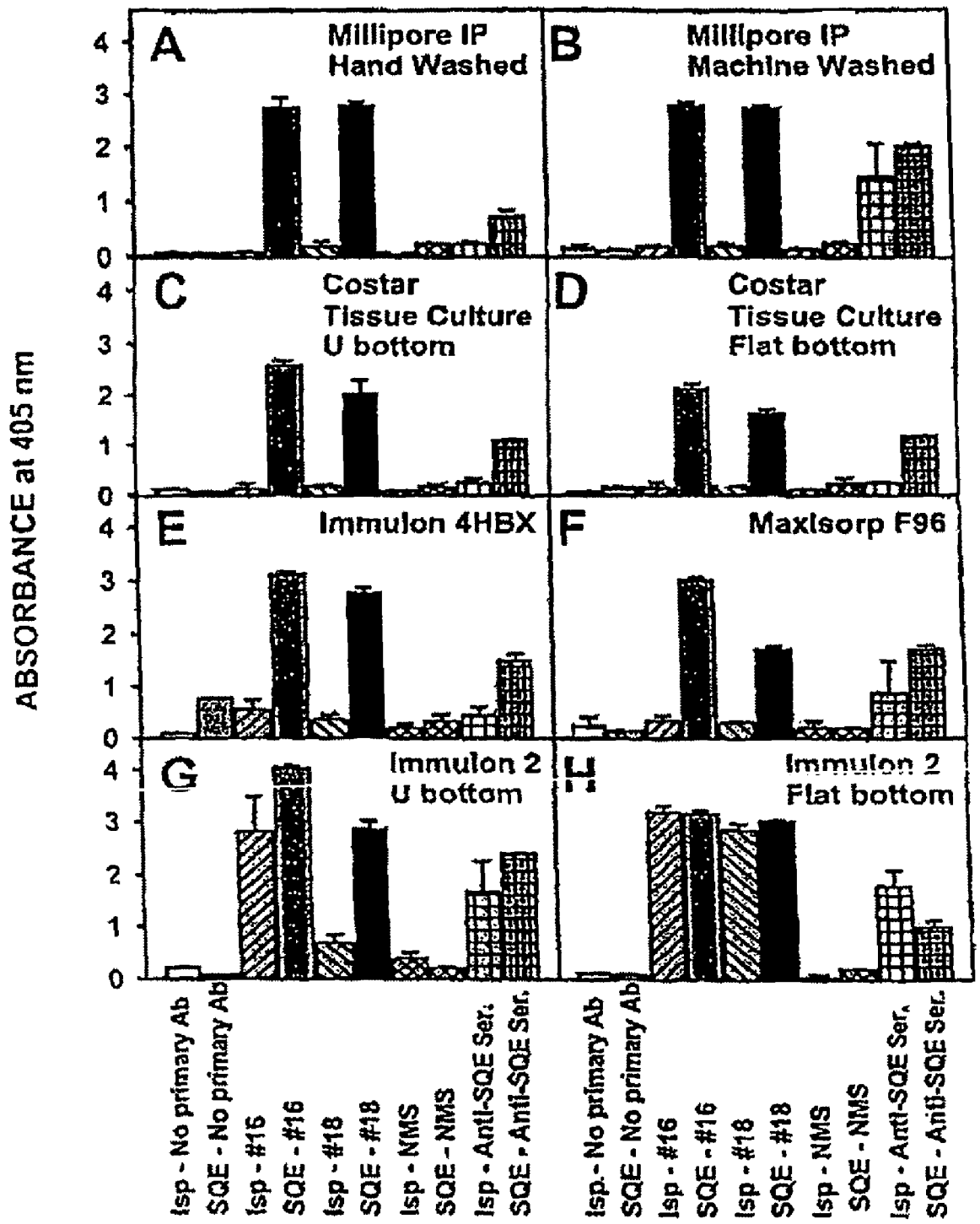

FIG. 9 shows the comparison of plates from different manufacturers with PBS-4% FBS as a blocker/diluent. Plates were coated with 100 nmol of SQE. mAbs SQE #16 and SQE #18 were diluted 1:10. The normal mouse serum and anti-SQE serum were diluted 1:50. The ELISA was performed as described for the standard protocol using PBS-4% FBS. Values are the mean of triplicate determination±standard deviation.

Figure 10:
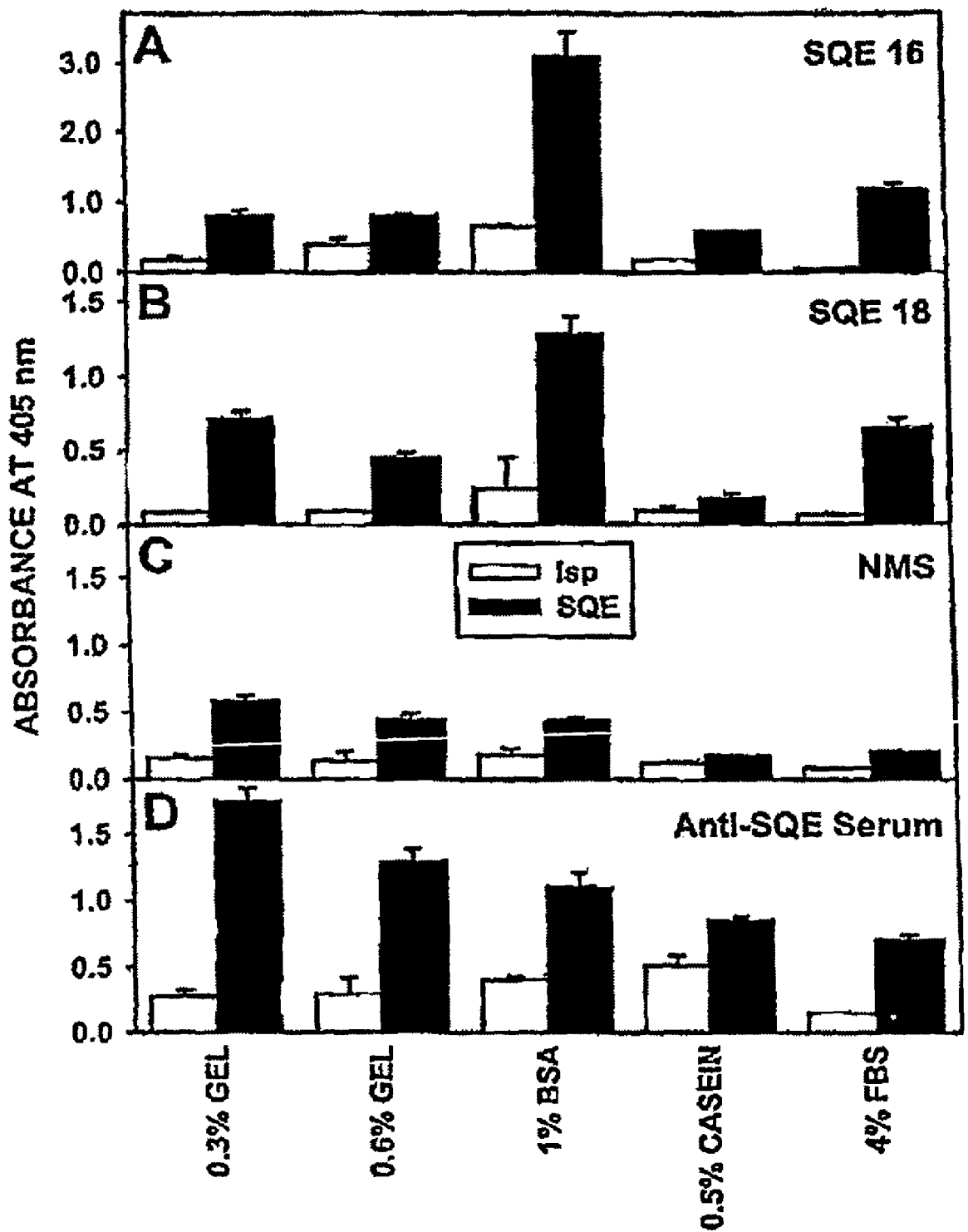

FIG. 10 shows the comparison of different blocker/diluents on the binding of antibodies to SQE. Costar U bottom plates were used. Plates were coated with 100 nmol of SQE. Clone SQE #16 (A) and SQE #18 (B) were diluted 1:10 in PBS, pH 7.4 containing the blocker/diluents indicated. Normal mouse serum (C) and anti-SQE serum (D) were diluted 1:50. The ELISA was performed as described for the standard protocol. Values are the mean of triplicate determination±standard deviation.

Figure 11:
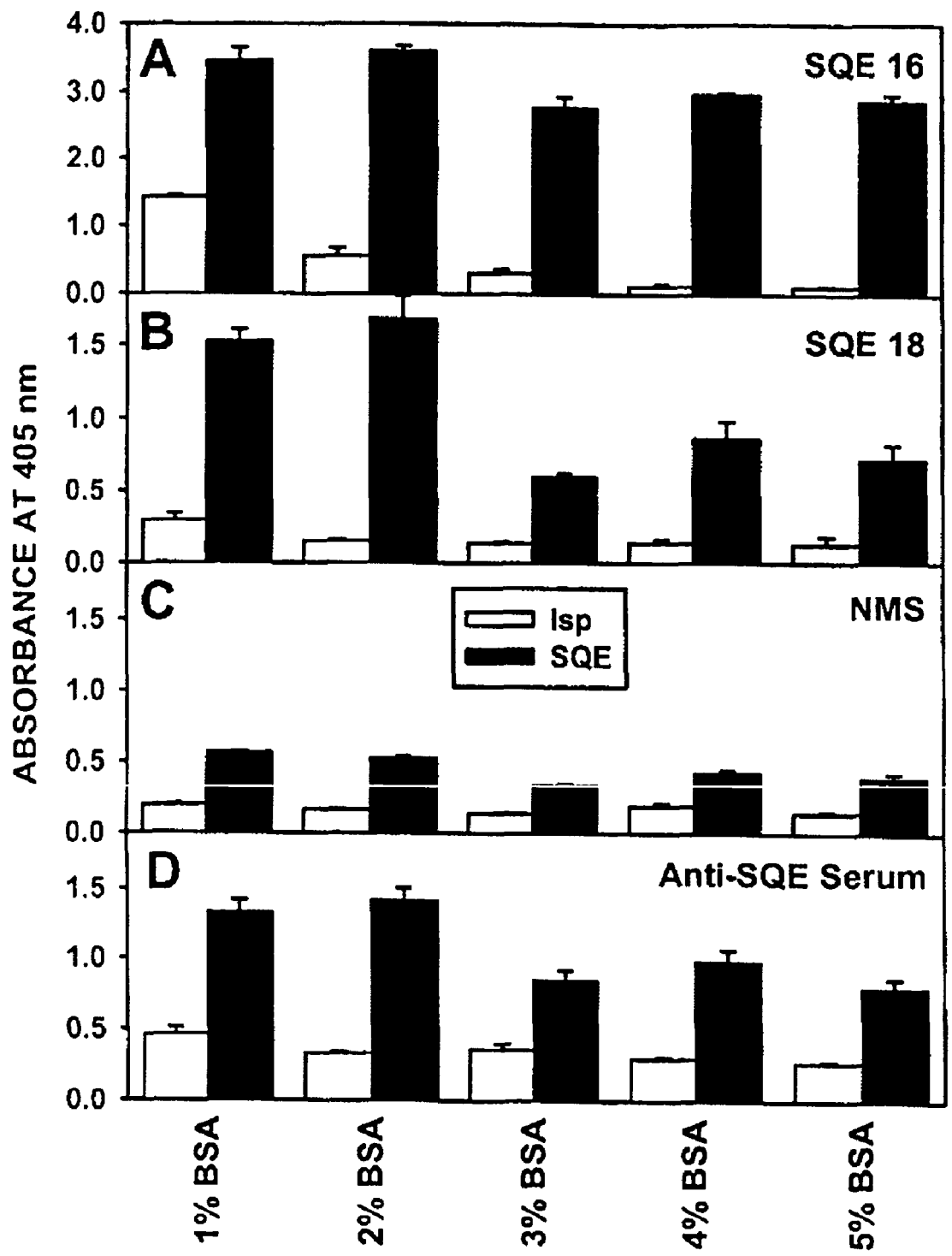

FIG. 11 shows the comparison of different amounts of BSA used as the blocker/diluent. Costar U bottom plates were used. Plates were coated with 100 nmol of SQE. Antibodies were diluted in PBS containing the percent BSA indicated. Clone SQE #16 (A) and SQE #18 (B) were diluted 1:10. Normal mouse serum (C) and anti-SQE serum (D) were diluted 1:50. The ELISA was performed as described for the standard protocol. Values are the mean of triplicate determination±standard deviation.

Figure 12:
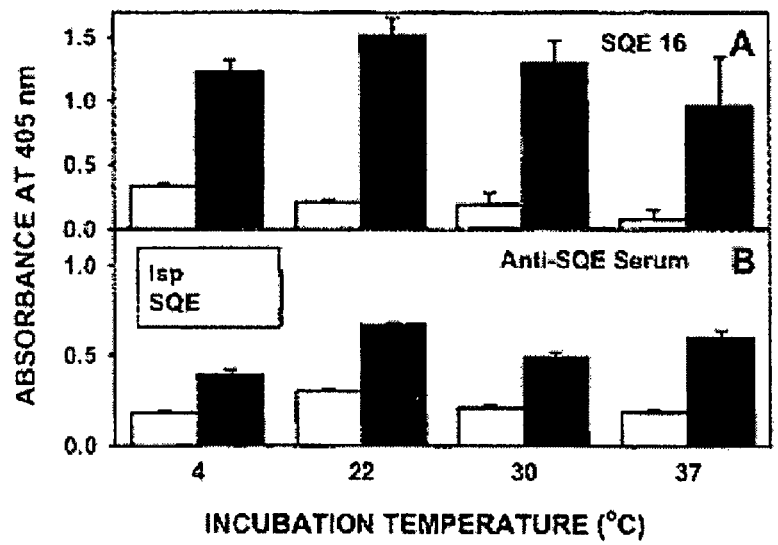

FIG. 12 shows the binding of anti-SQE antibodies to SQE-coated plates as a function of incubation temperature. Plates were coated with 100 nmol of SQE. PBS-2% BSA was used as a blocker/diluent, which was equilibrated to temperature indicated. Clone SQE #16 (A) and the anti-SQE serum (B) were diluted 1:50 and 1:100 respectively. The ELISA was performed as described for the standard assay except the incubations were at the temperature indicated. Values are the mean of triplicate determination±standard deviation.

Figure 13:
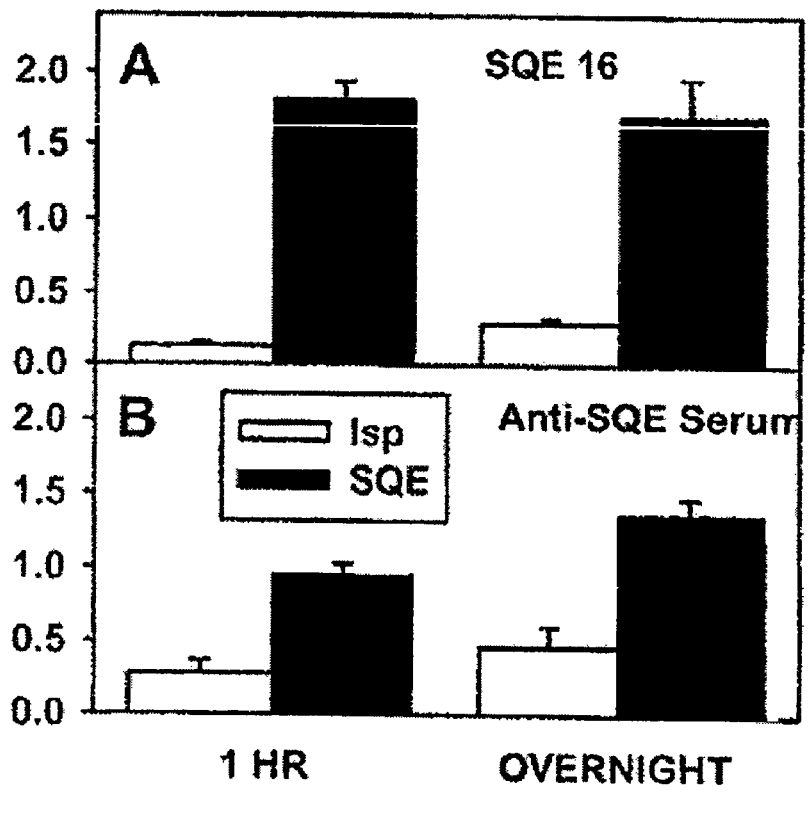

FIG. 13 shows the binding of anti-SQE antibodies to SQE-coated plates as a function of primary antibody incubation time. Plates were coated with 100 nmol of SQE. PBS-2% BSA was used as a blocker/diluent. Clone SQE #16 and the anti-SQE serum were diluted 1:100. The ELISA was performed as described for the standard protocol except for the primary antibody incubation time. Values are the mean of triplicate determination±standard deviation.

Figure 14:
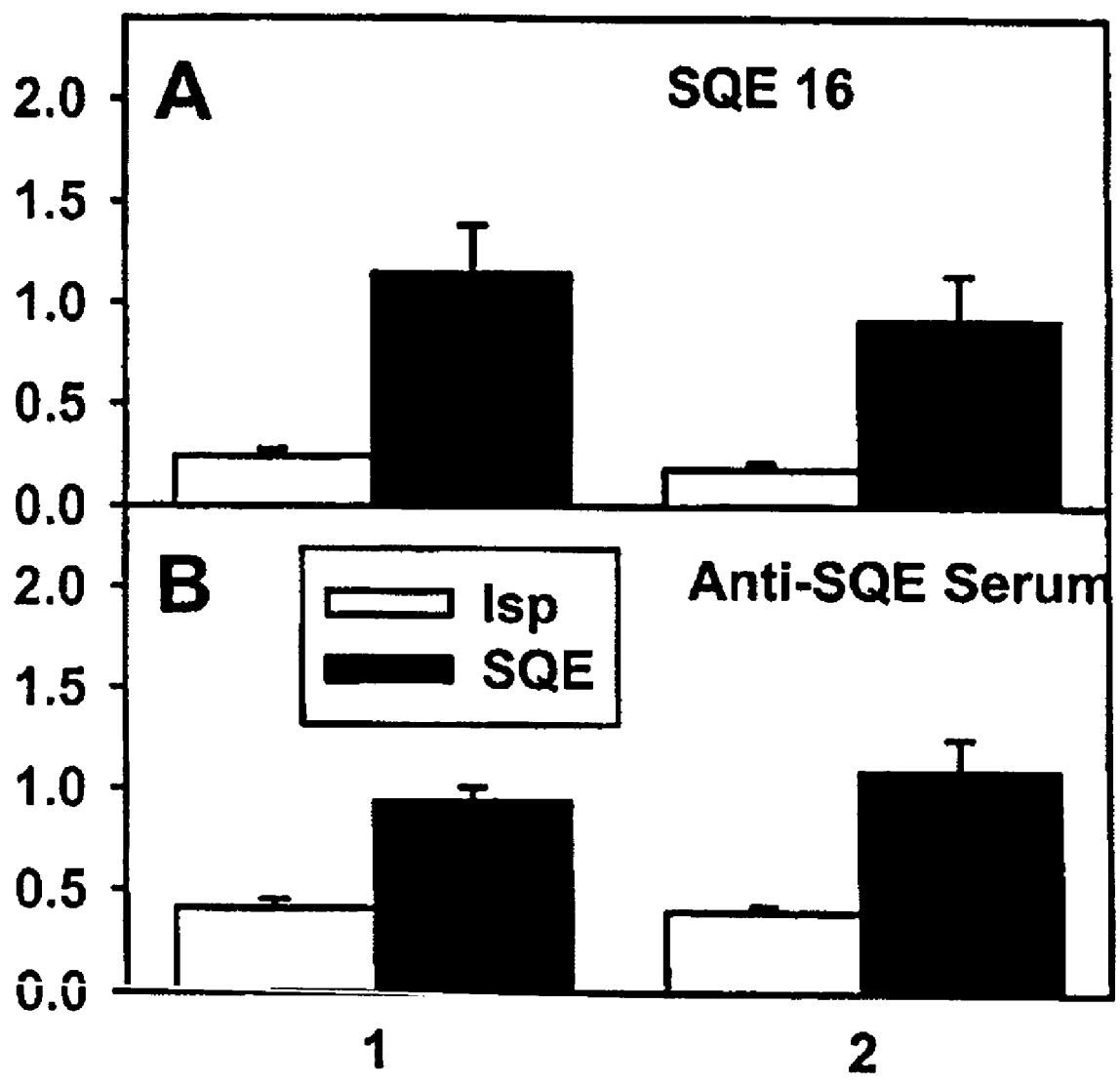

FIG. 14 shows the effect of secondary antibody incubation time on ELISA absorbance of antibodies binding to SQE. Plates were coated with 100 nmol of SQE. PBS-2% BSA was used as a blocker/diluent. Clone SQE #16 and the anti-SQE serum were diluted 1:40 and 1:50, respectively. The ELISA was performed as described for the standard protocol except for the secondary antibody incubation time. Values are the mean of triplicate determination±standard deviation.

Figure 15:
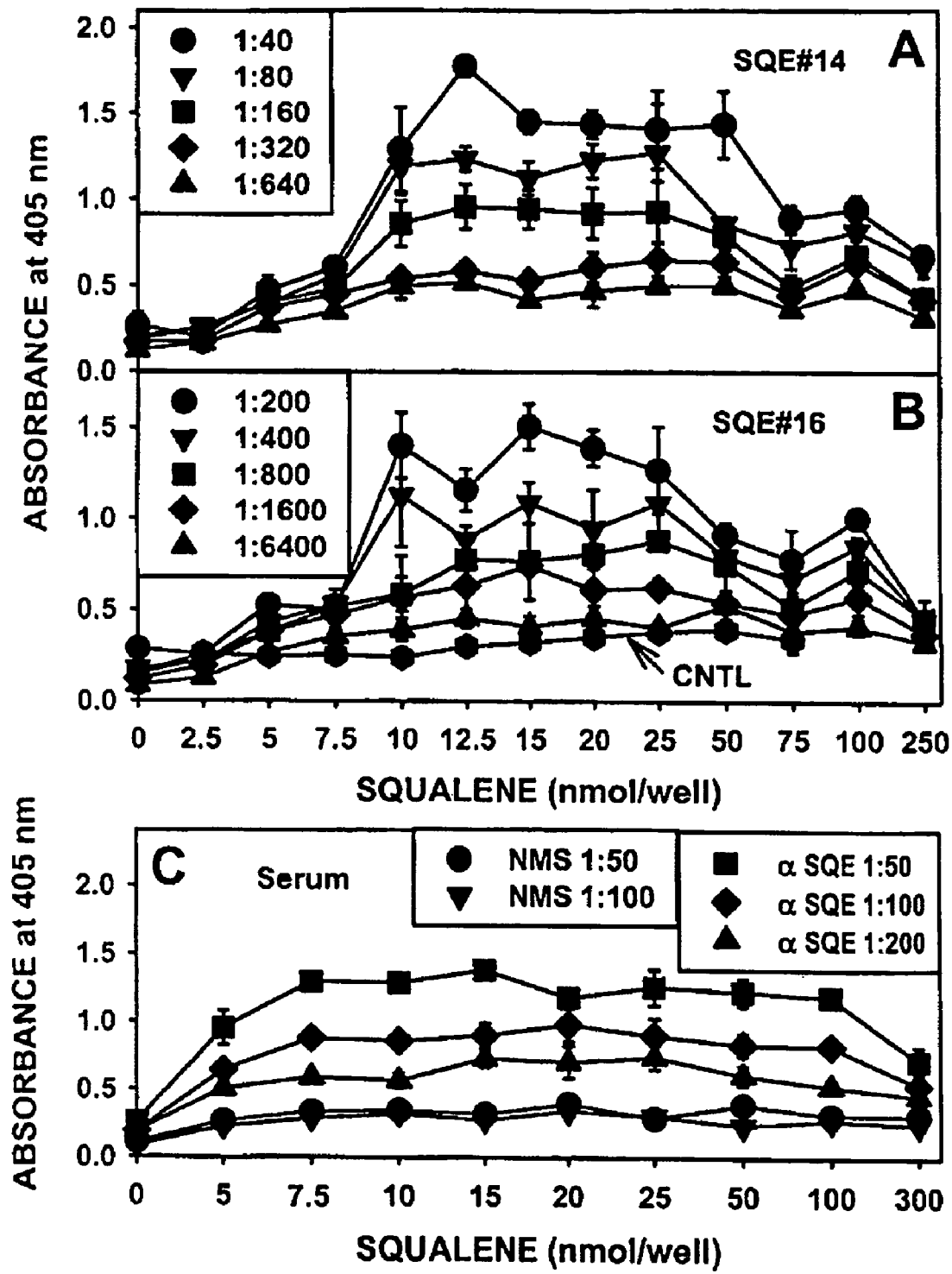

FIG. 15 shows the binding of anti-SQE antibodies as a function of SQE-coated on the well. Plates were coated with the amount of SQE indicated. PBS-2% BSA was used as a blocker/diluent. Clones SQE #14 (A) and SQE #16 (B) and serum (C) was diluted as indicated. The ELISA was performed as described for the standard protocol. Values are the mean of triplicate determination±standard deviation.

Figure 16:
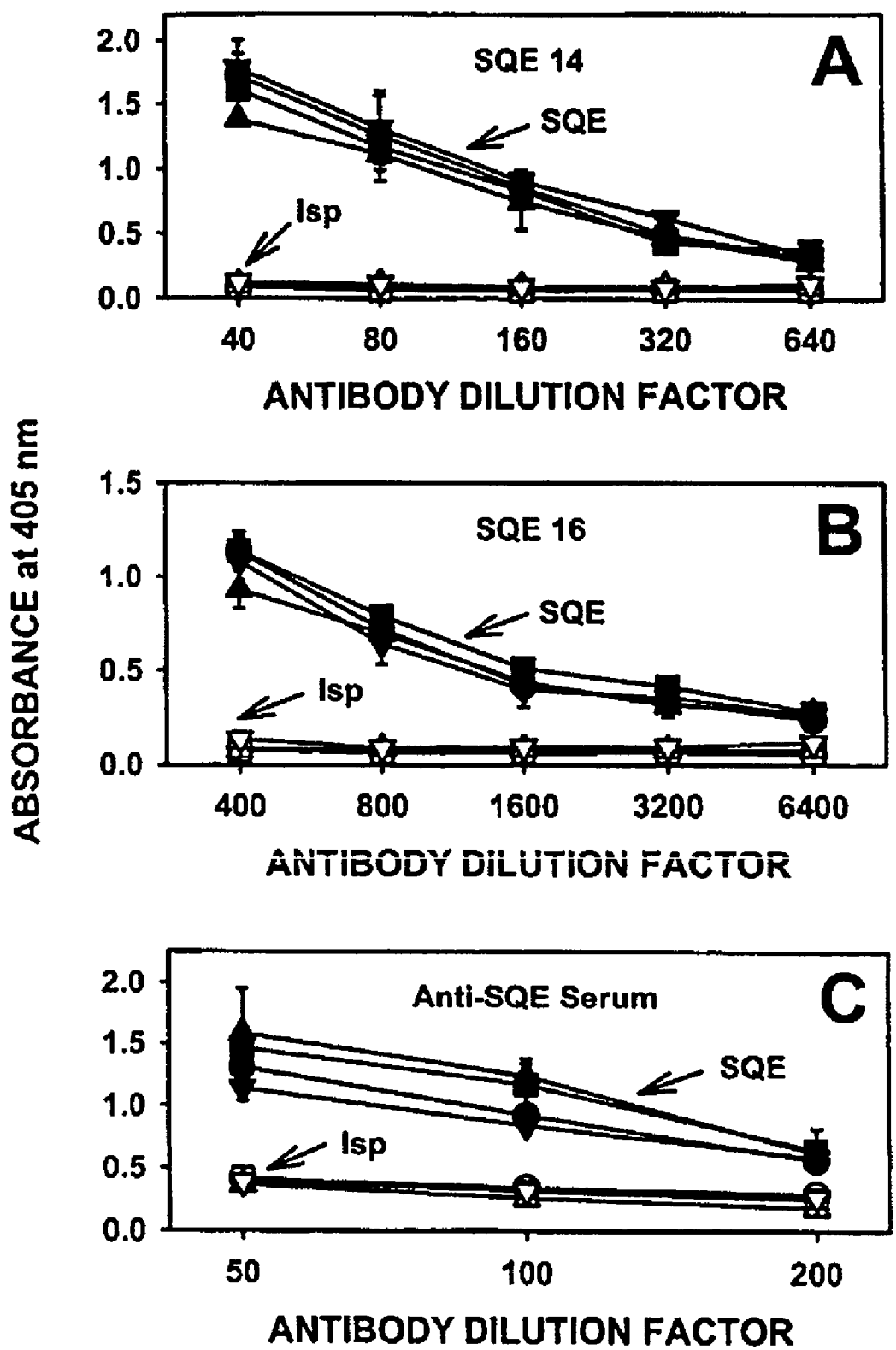

FIG. 16 shows the comparison of different lots of plates. Plates were coated with 10 nmol of SQE. PBS-2% BSA was used as a blocker/diluent. Clone SQE #14 (A), clone SQE #16 (B) anti-SQE serum (C) were used as primary antibodies. The ELISA was performed as described for the standard protocol. Each symbol is a plate with a different lot number. Values are the mean of triplicate determination±standard deviation.

Figure 17:
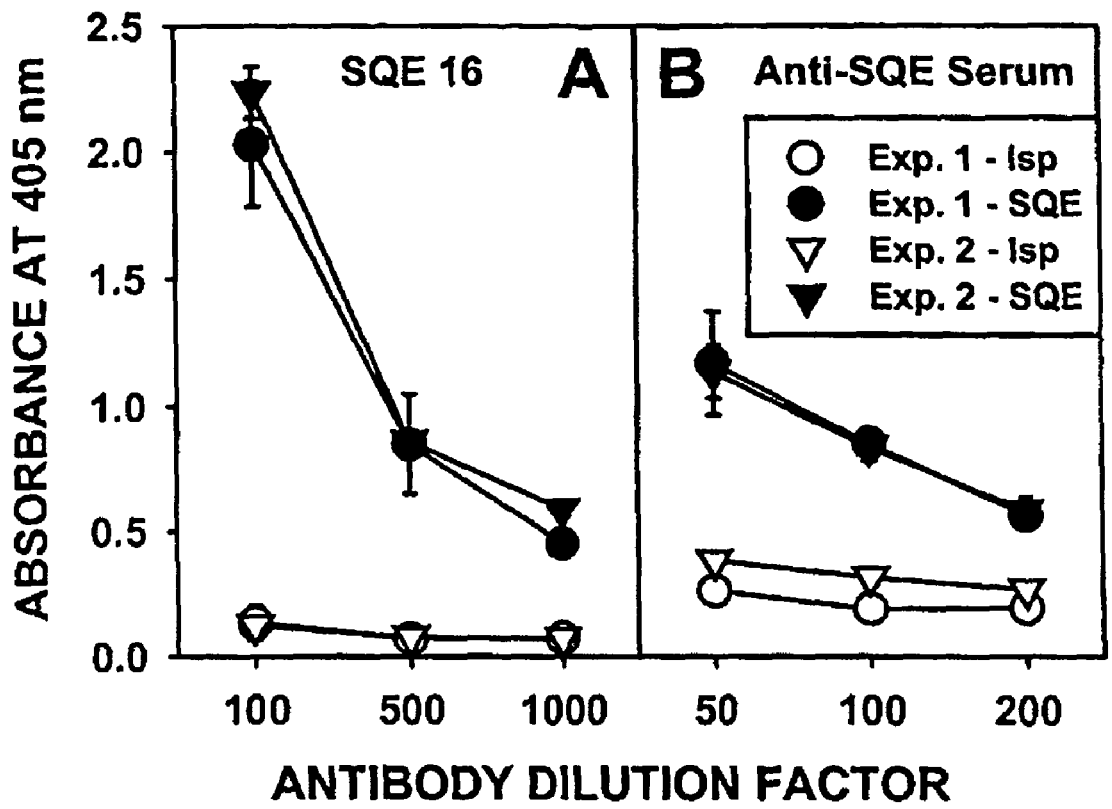
Figure 18:
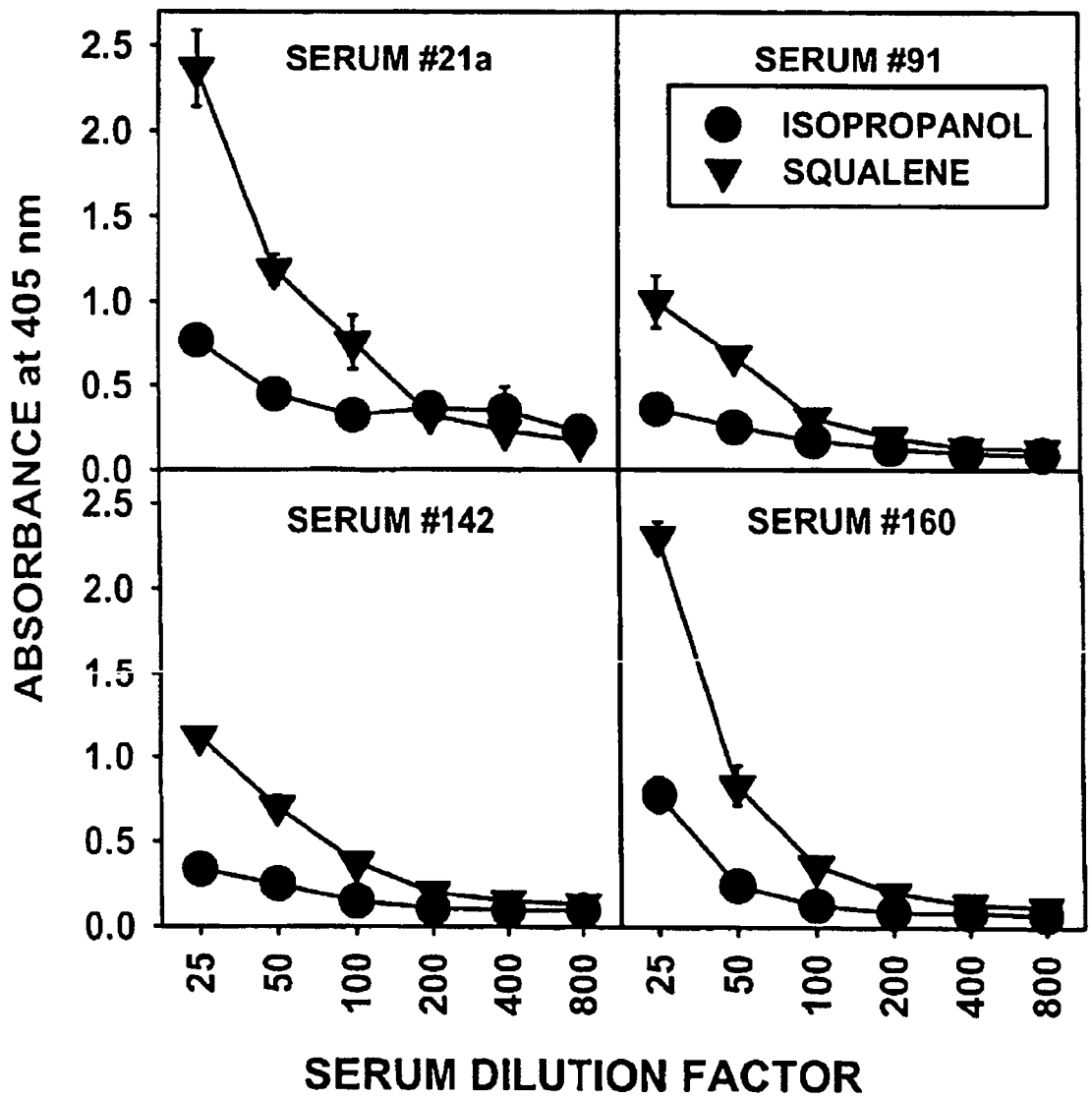
Figure 19:
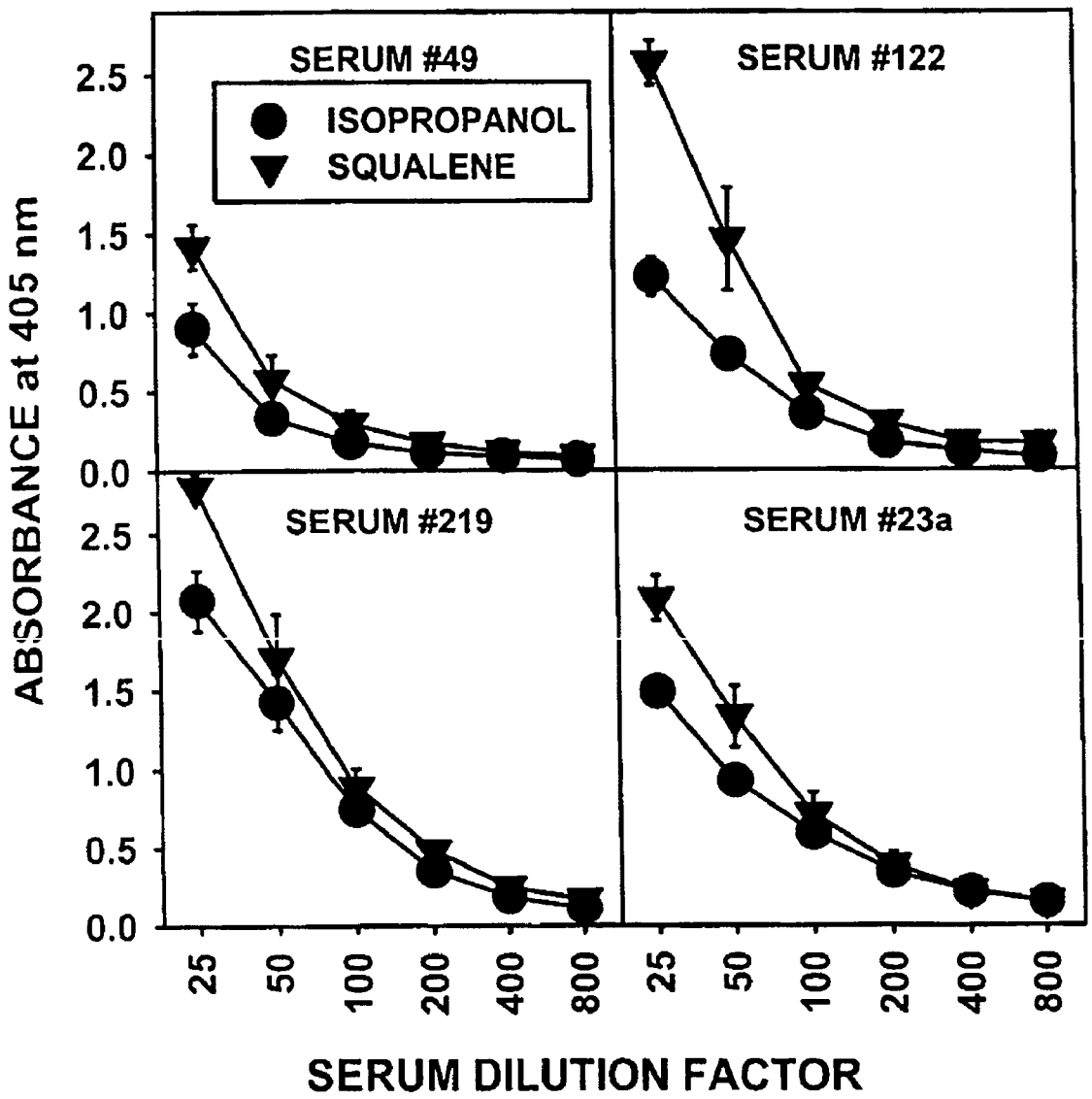
Figure 20:
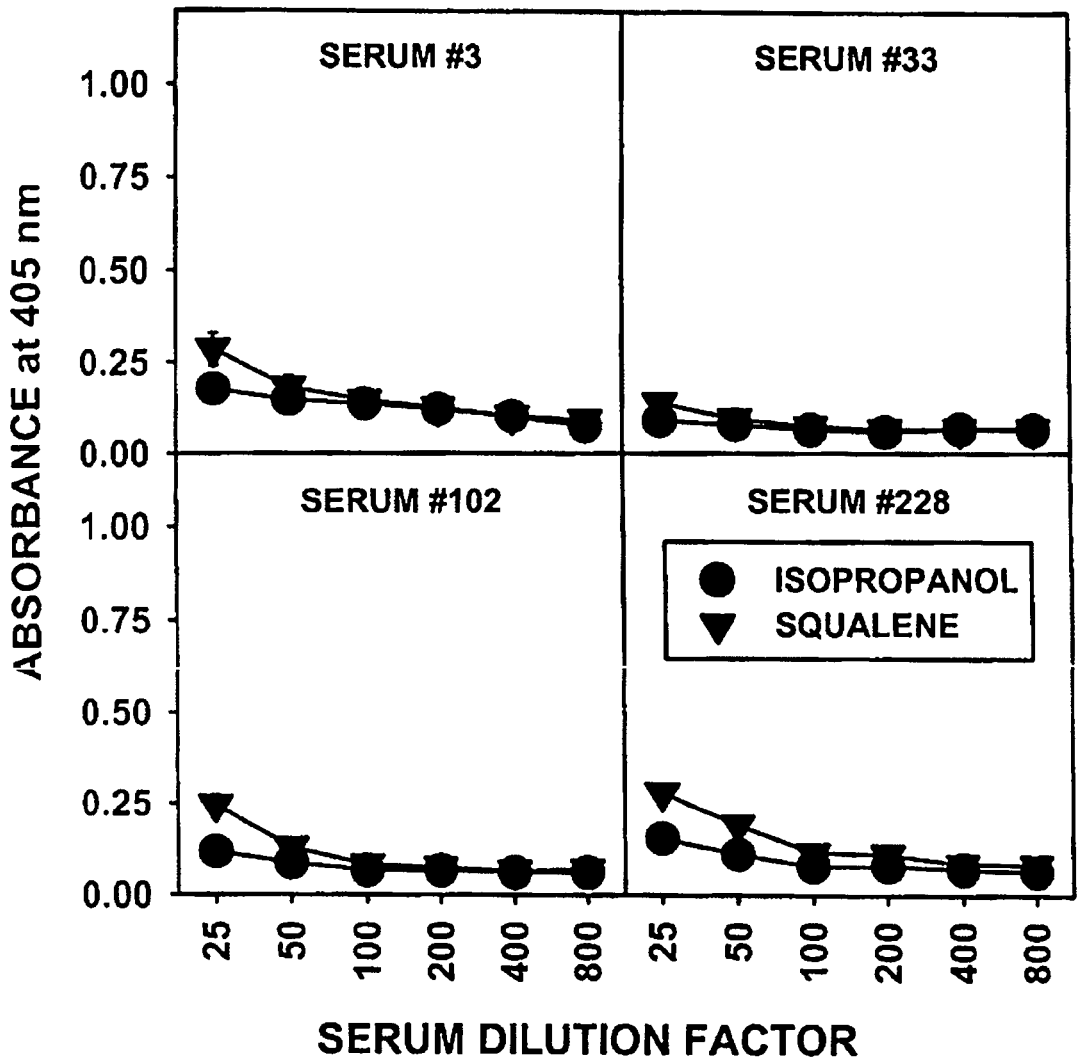
Figure 21:
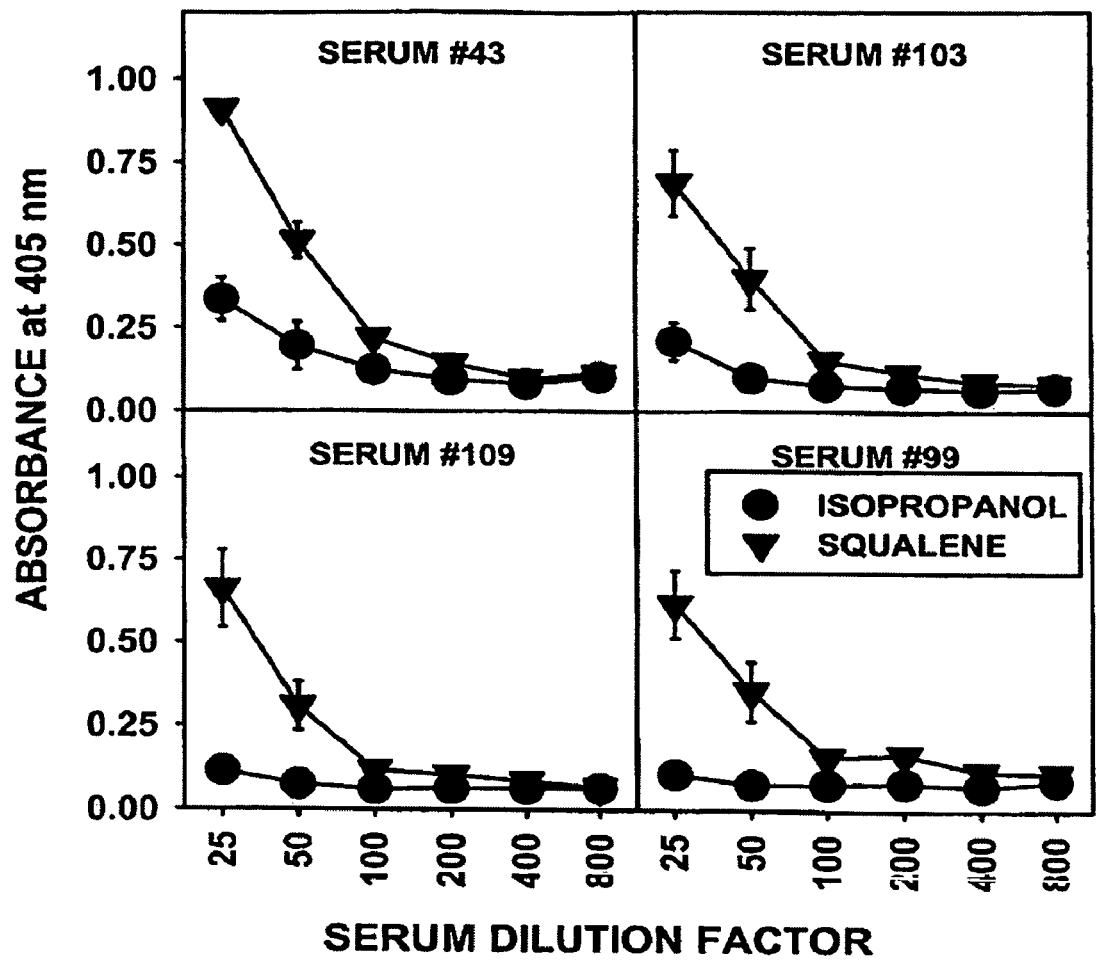
Figure 22:
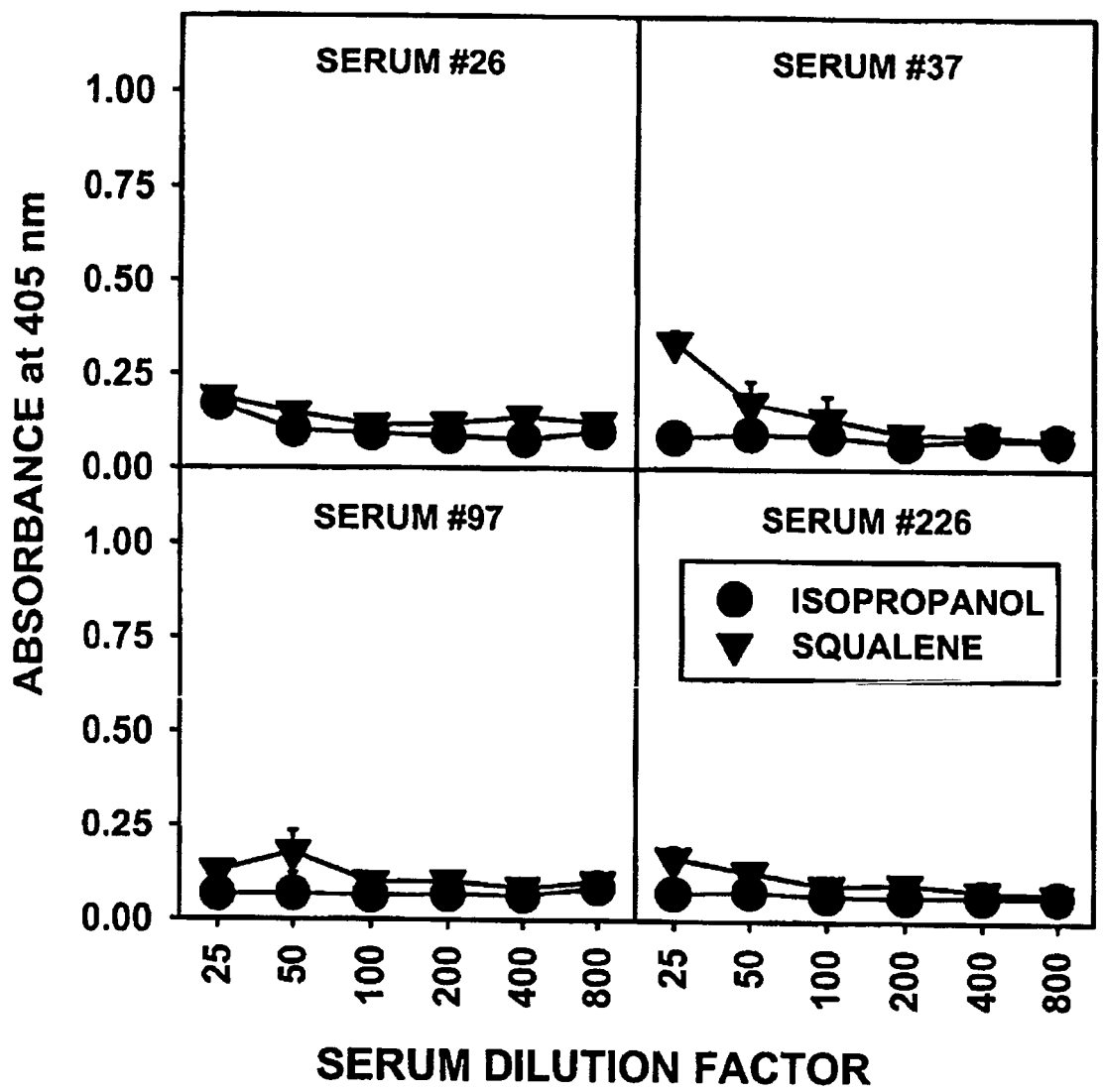

FIG. 17 shows the day to day reproducibility of the ELISA assay for antibodies to SQE. Plates were coated with 10 nmol of SQE. PBS-2% BSA was used as a blocker/diluent. Experiments 1 and 2 were done on separate days using the standard protocol. Values are the mean of triplicate determination±standard deviation.

FIGS. 18-22 shows the results of the experiments described in Example 19, illustrating the applicability of the method of the present invention to detecting anti-squalene antibodies in human sera.

Figure 23:
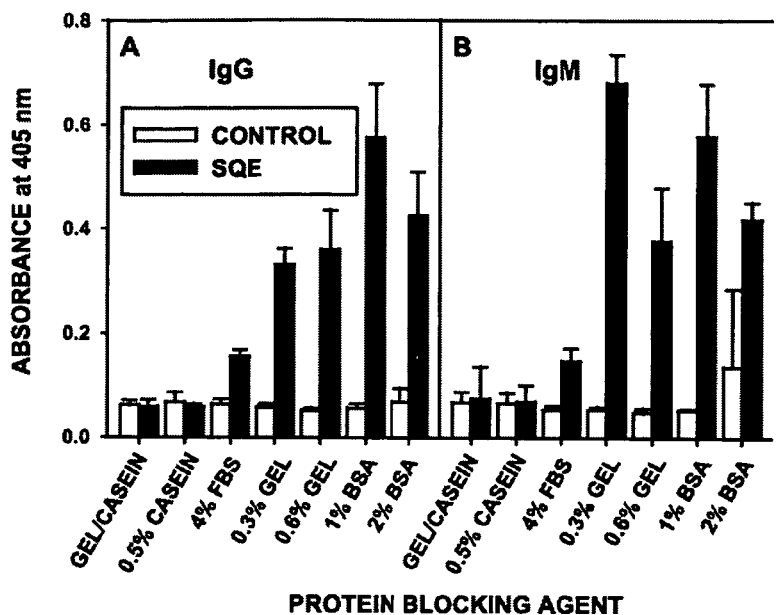

FIG. 23 illustrates comparison of blocking and diluent agents on secondary antibody binding to control (ISP (isopropanol)-treated) and SQE-coated wells (20 nmol/well). Assays were conducted in PBS, pH 7.4 containing the blocker and diluent protein indicated. GEUCASEIN wells were blocked in 0.6% gelatin and the secondary antibody was diluted in 0.5% casein. All other samples were blocked and diluted in the protein buffer indicated. Values were the mean of triplicate determinations±standard deviation.

Figure 24:
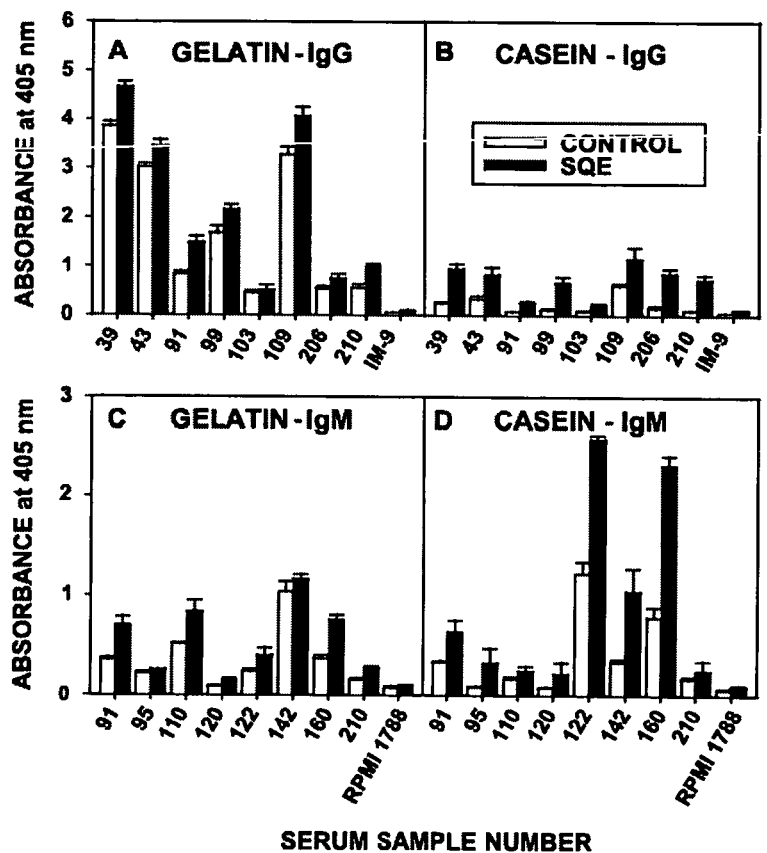

FIG. 24 depicts comparison of blocking agents on antibodies binding to control (ISP-treated) and SQE-coated wells (20 nmol/well). Wells were blocked with PBS-0.6% gelatin (A, C) or PBS-0.5% casein (B, D). The serum and secondary antibodies were diluted in PBS-0.5% casein. Values were absorbances from sera diluted 1:25 and assayed for IgG (A, B) and IgM (C, D) and are the mean of triplicate determinations F standard deviation. Culture supernatants of control human monoclonal antibodies IM-9 (IgG) and RPMI 1988 (IgM) were used at a concentration of 4 µg/ml.

Figure 25:
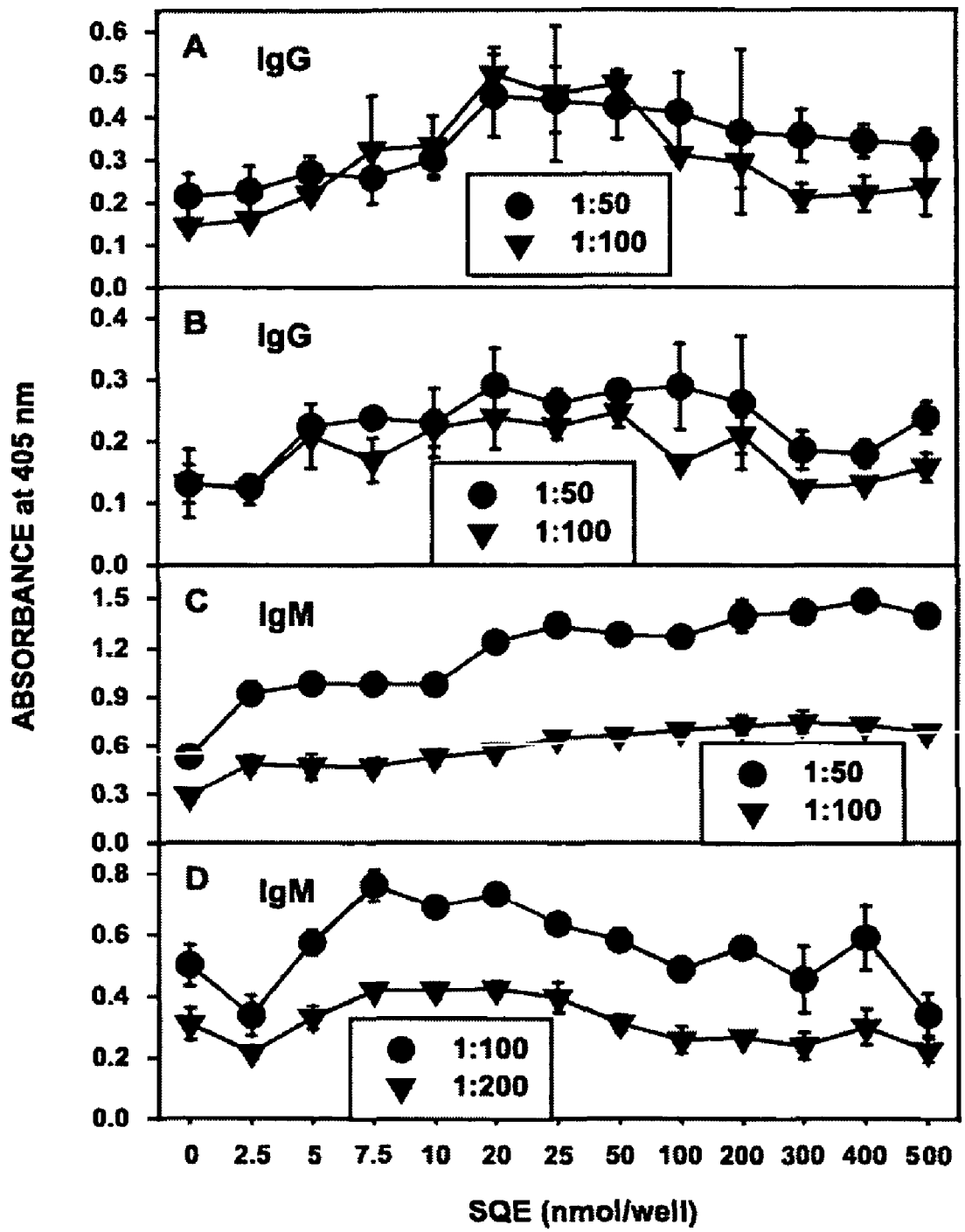

FIG. 25 is a graph illustrating the binding of serum anti-SQE antibodies as a function of the amount of SQE added to the well. Wells were incubated with the amount of SQE indicated in 100 µl of ISP. The ELISA was performed using the protocol described herein with PBS –0.5% casein as the blocker and diluent. Values were the mean of triplicate determinations F standard deviation.

Figure 26:
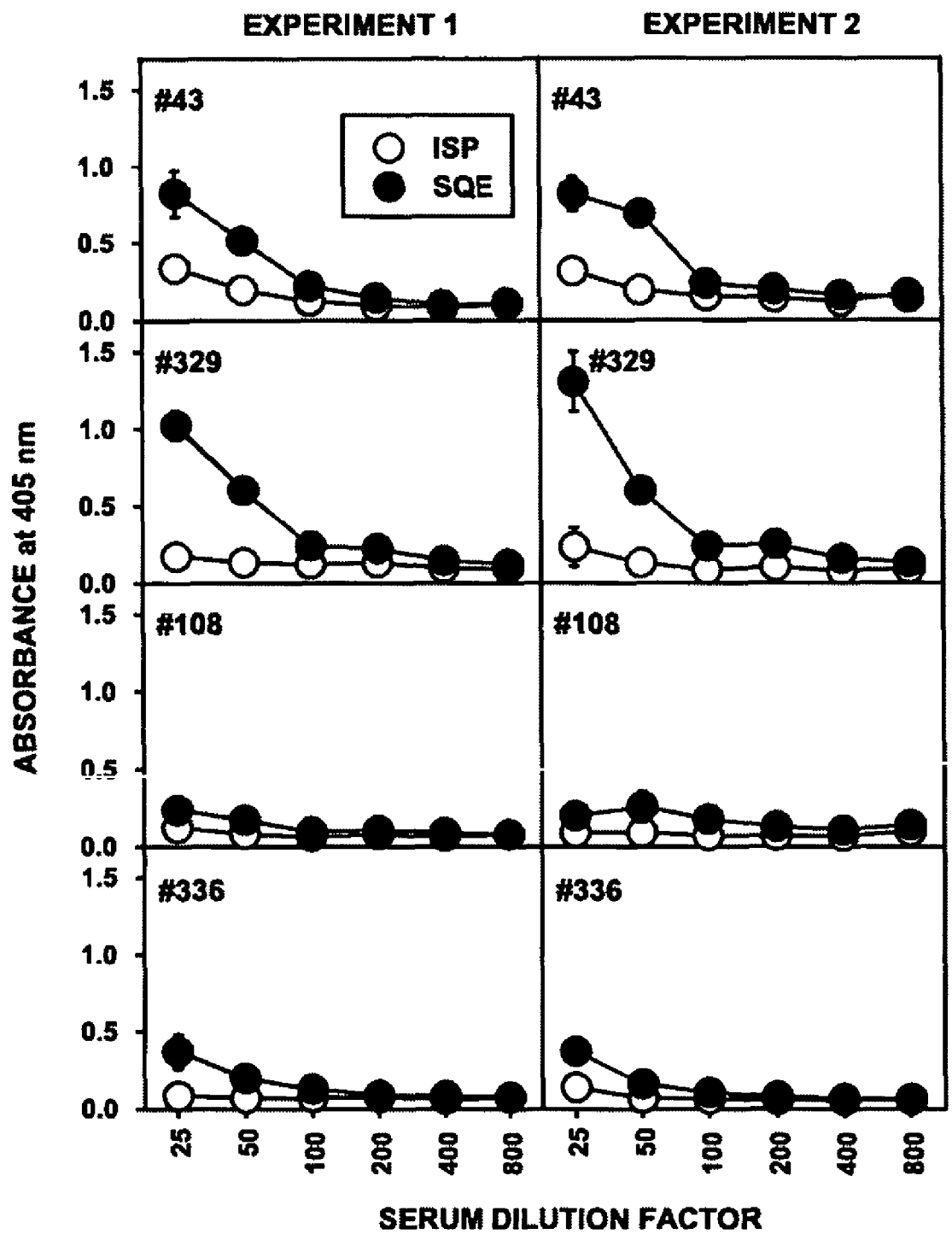

FIG. 26 is a graph showing ELISA dilution curves from representative human sera assayed in two different experiments for IgG antibodies to SQE. Samples positive for antibodies to SQE are serum #43 and 329. Samples negative for antibodies to SQE are serum #108 and 336. The ELISA assay was performed using the protocol described in herein with PBS −0.5% casein as the blocker and diluent. Values were the mean of triplicate determinations F standard deviation. Sera were judged to be positive for antibodies to SQE if two dilutions (i.e., 1:25 and 1:50) had absorbances that were greater than 3 times baseline. Baseline was defined as the absorbance at which the dilution curve became horizontal.

Figure 27:
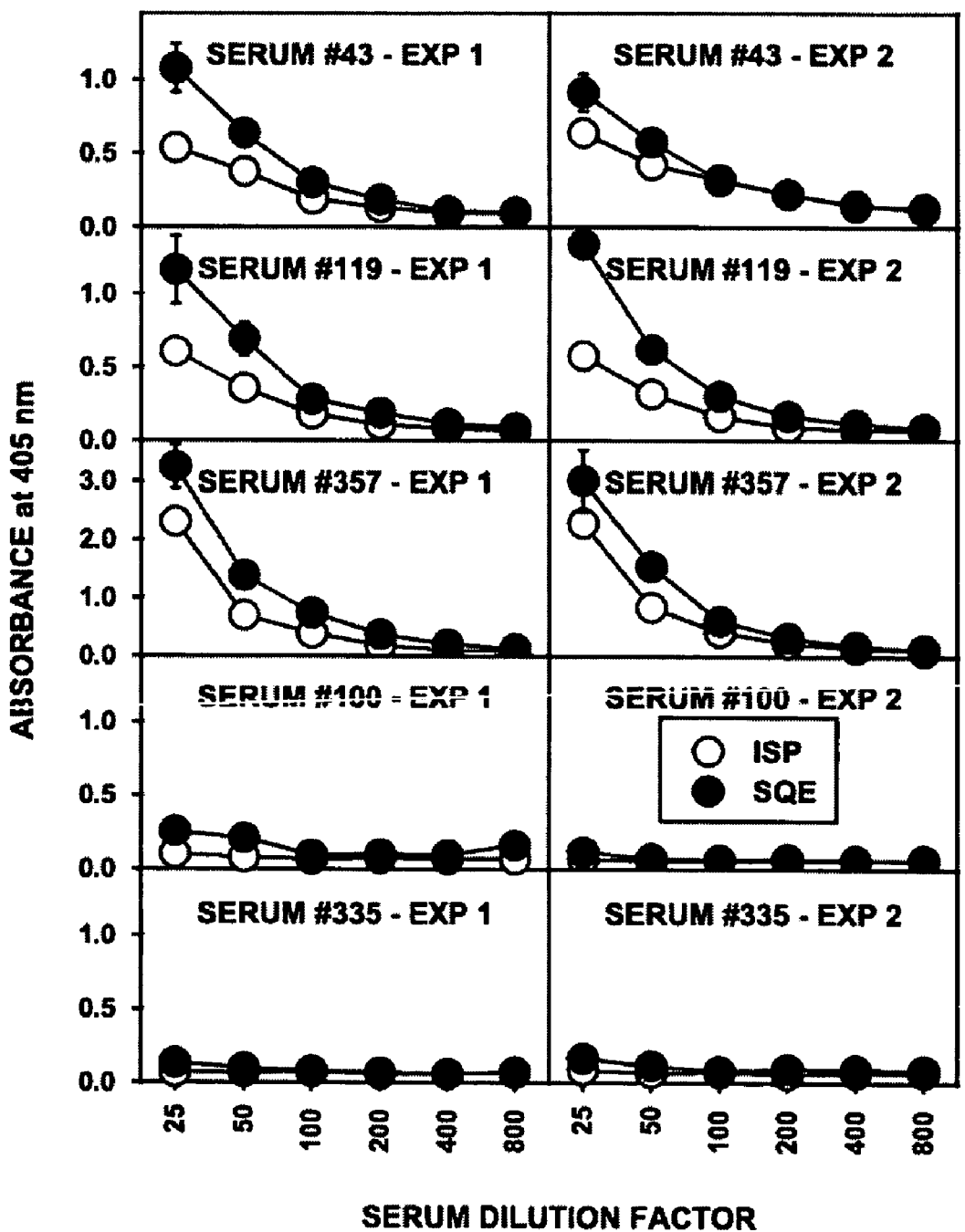

FIG. 27 depicts the effect of freeze-thaw on the ELISA dilution curves for antibodies to SQE from representative human serum samples. Serum was obtained frozen, thawed and assayed. An aliquot was frozen at −70° C. overnight and assayed the next day. The ELISA assay was performed using the protocol described herein with PBS-0.5% casein as the blocker and diluent and peroxidase-linked anti-mouse IgM as the second antibody. Values were the mean of triplicate determinations F standard deviation. Sera were from the USAMRIID alumni cohort #4 (A, B), #5 (C, D), #21 (E, F) and the Frederick cohort #329 (G, H).

Figure 28:
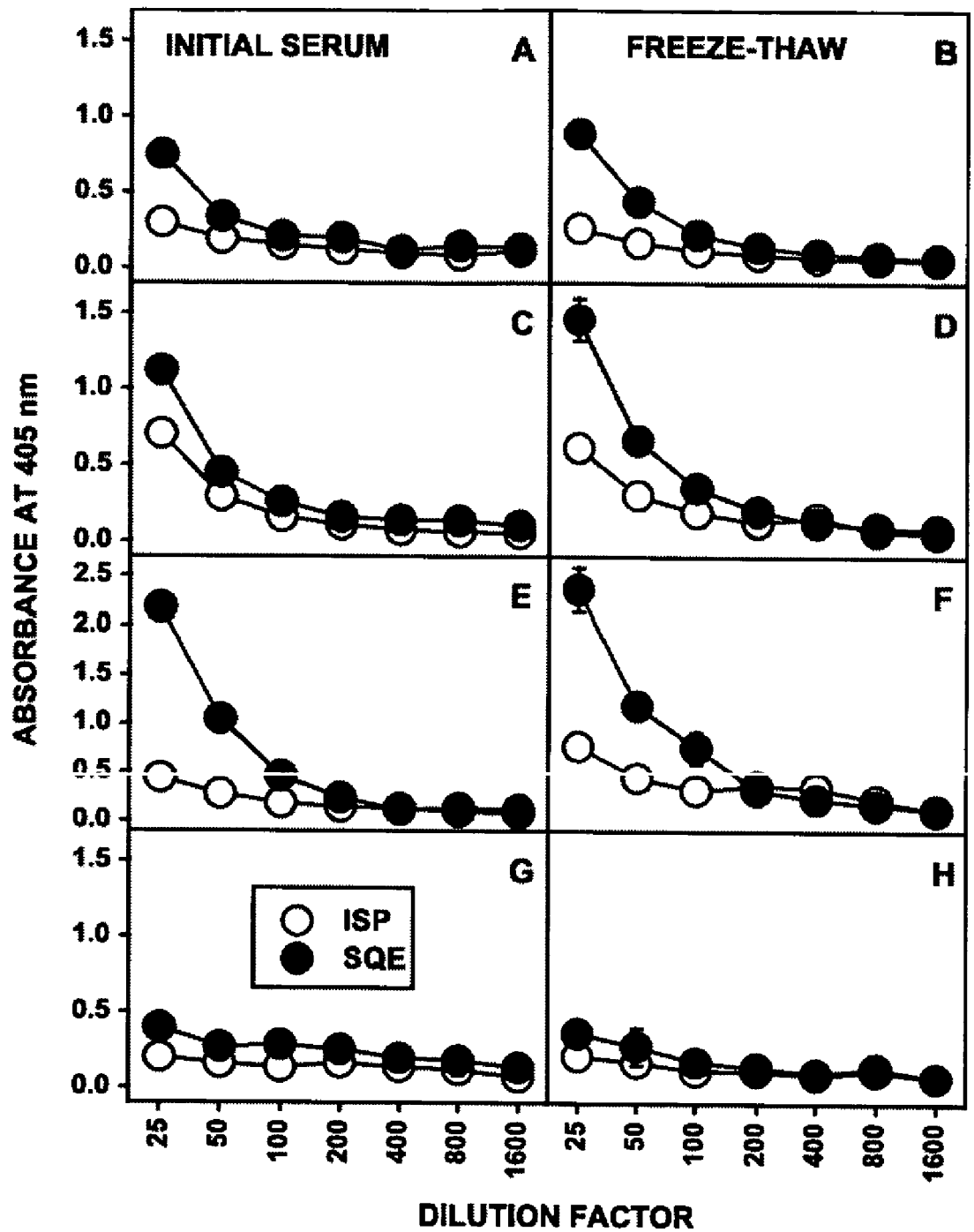

FIG. 28 shows ELISA dilution curves from representative human sera assayed in two different experiments for IgM antibodies to SQE. Samples positive for antibody to SQE are serum #43 and 119. Sample #357 has high background. Samples negative for antibodies to SQE are serum #100 and 335. The ELISA assay was performed using the protocol described herein with PBS-0.5% casein as the blocker and diluent. Values were the mean of triplicate determinations F standard deviation. Sera were judged to be positive for antibodies to SQE if two dilutions (i.e., 1:25 and 1:50 dilutions) had absorbances that were greater than 3 times baseline. Baseline was defined as the absorbance at which the dilution curve became horizontal.

Figure 29:
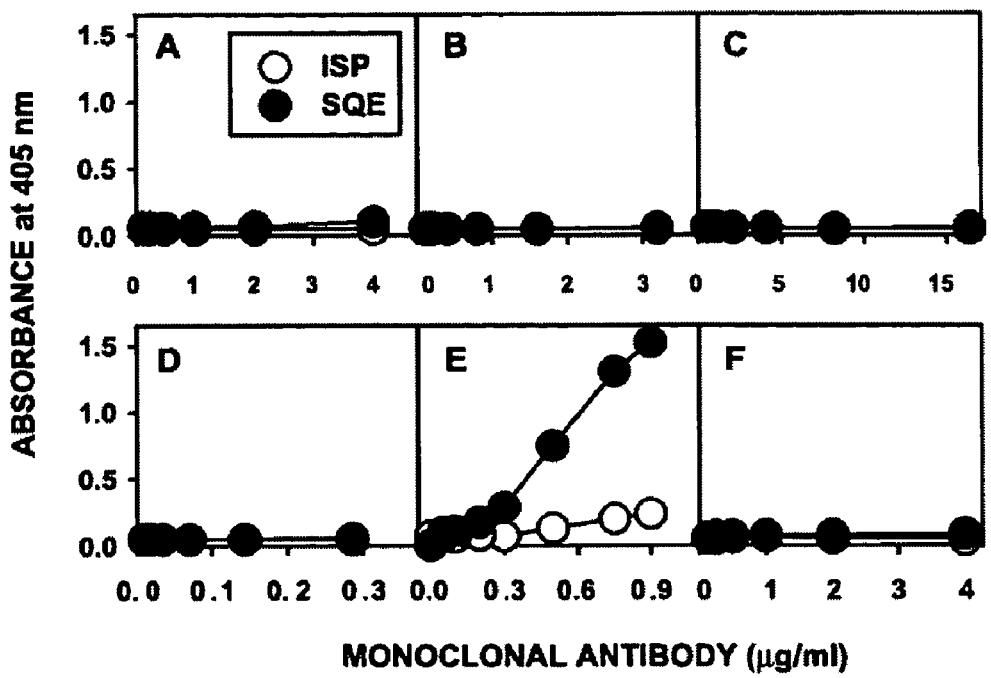

FIG. 29 depicts culture supernatants containing human monoclonal antibodies were assayed by ELISA for reactivity to SQE or polystyrene. The ELISA assay was performed using the protocol described herein with PBS-0.5% casein as the blocker and diluent. Values were the mean of triplicate determinations F standard deviation. Panel A was IM-9, which secreted an IgG antibody of unknown specificity cloned from a human myeloma (Fahey, 1971). Panel B was 16M3F10, which secreted an IgG antibody to diphtheria toxoid (Gigliotti, 1984). Panel C was SA13, which secreted an IgG antibody to tetanus toxoid (Larrick, 1986). Panel D was L612, which secreted an IgM antibody to the gangliosides GM3 and GM4 (Irie, 1995). Panel E was C5, which secreted an IgM antibody to lipid A of Gram negative bacteria (Teng, 1985). Panel F was RPMI 1788, which secreted an IgM antibody to tumor necrosis factor beta (Aggarwal, 1984).

Figure 30:
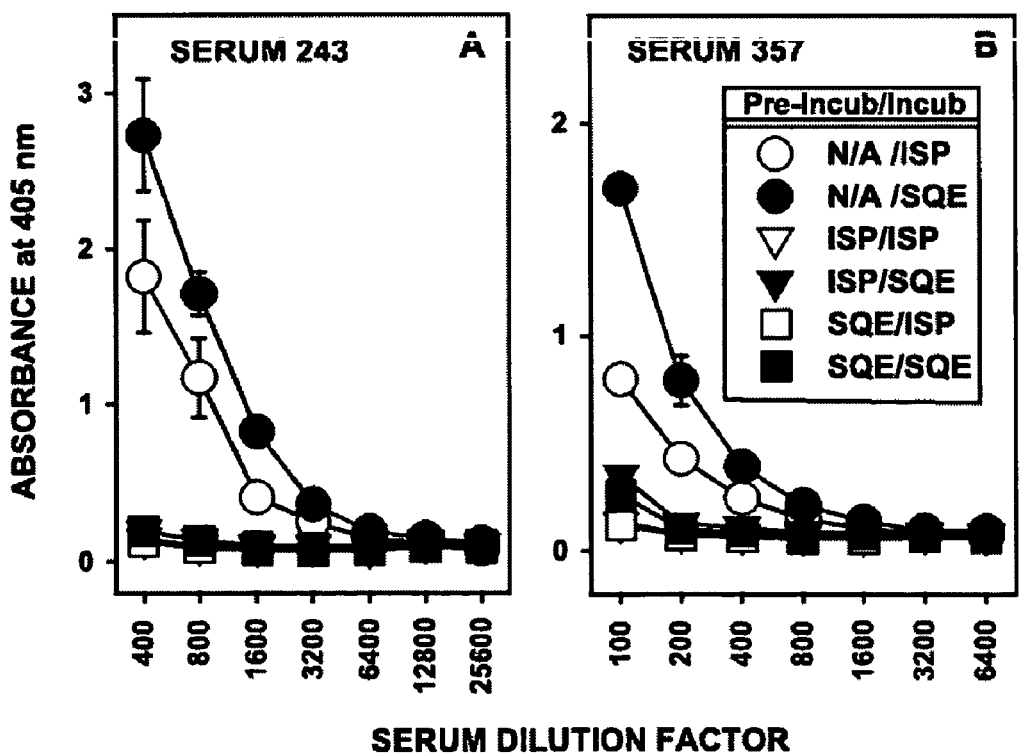

FIG. 30 represents the effect of pre-incubation of serum on control (ISP-treated) or SQE-coated wells on the binding to control or SQE-coated wells. Sera was diluted in PBS-0.5% casein and plated on 96-well plates treated with ISP or coated with SQE. Following incubation for 2 h at room temperature, the contents of the wells were transferred to a new plate containing wells treated with ISP or SQE. Following incubation overnight at room temperature, the supernatant were removed and assayed by the standard ELISA for IgM antibodies to SQE. Unabsorbed sera (circles) were serum samples assayed by ELISA without prior adsorption. Values were the mean of triplicate determinations F standard deviation.

Figure 31:
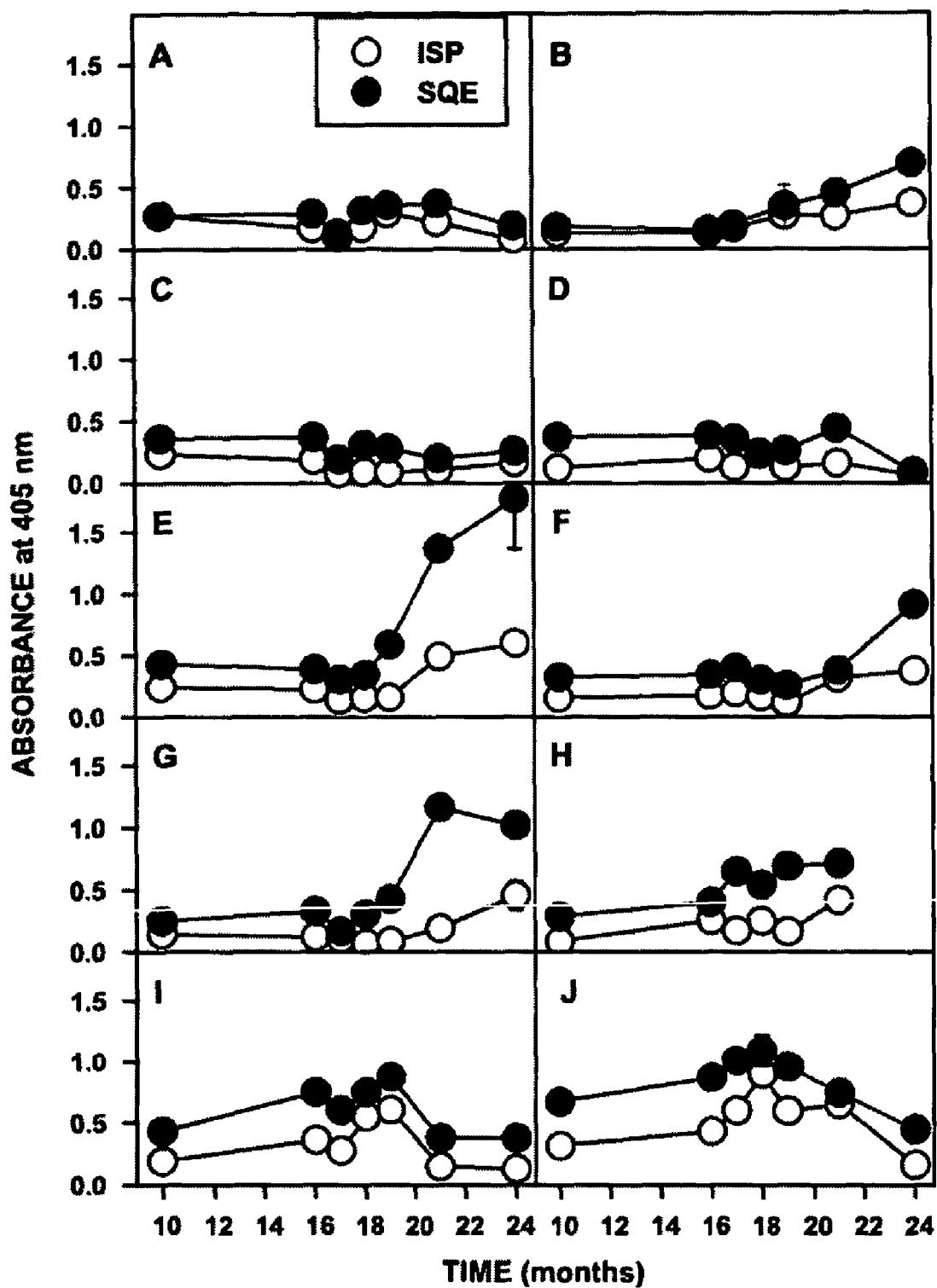

FIG. 31 shows the occurrence of naturally occurring antibodies to squalene in mice as a function of age. Each panel represents a different mouse. Panels A and B are IgG and panels C-J are IgM. Values were the mean of triplicate determinations F standard deviation of the serum diluted 1:100.

VII. DETAILED DESCRIPTION OF THE INVENTION

The earlier subject matter upon which the present invention is based is replicated so as to emphasize the improvement and to delineate overlapping references, techniques, and materials employed in the practice of the improvement represented by the present invention also contemplates the use of that monoclonal antibody, or a segment or portion thereof, in an immunoassay for the detection of human anti-squalene antibodies. "Anti-squalene antibody" refers to an antibody capable of complexing with squalene. Such an antibody may complex with squalene, or with any antigenic epitope presented by squalene.

The present invention is for detection of human antibodies that specifically bind to squalene, and methods for producing the monoclonal antibody. "Squalene" refers to a hydrocarbon of the chemical formula $C_{30}H_{50}$ [2, 6, 10, 15, 19, 23-hexamethyl-2, 6, 10, 14, 18, 22-tetracosahexaene], CAS Number [111-02-4]. In preferred embodiments of the invention, the immunoassay is specific for human anti-squalene antibodies.

The test sample may generally be any type of biological material containing antibodies. Such materials may be processed so that they are provided in a suitable form. The test sample is preferably provided from a bodily fluid, more preferably is provided from blood, and most preferably provided from serum. The test samples may generally be any organism which contains antibodies but consistent with the invention herein, the organism is human.

In accordance with the teachings of the inventor's prior application, in some embodiments of the present invention the immunoassay uses a polystyrene support in combination with certain blockers/diluents. Fetal bovine serum should not be used as a blocker/diluent because it appears to compete with antibody binding in the assay. Not intending to be limited to a particular theory, it is believed that fetal bovine serum itself includes an amount of squalene sufficient to block or diminish antibody binding.

In embodiments of the previously described invention, the assay uses a blocker/diluent that does not compete with squalene and/or anti-squalene antibodies. Exemplary blockers/diluents suitable for use with polystyrene supports include but are not limited to phosphate buffered saline (PBS), bovine serum albumin (BSA), gelatin, casein, or combinations or mixtures thereof. Preferred blockers/diluents include BSA; most preferred blockers/diluents include BSA and PBS. As noted in more detail in the examples, the preferred amount of BSA is up to about 5% by volume BSA, for example, from about 1% to about 2%.

In accordance with some embodiments of the previously disclosed invention, the immunoassay may use a hydrophobic membrane support, preferably polyvinylidene difluoride.

In accordance with the present invention, any assay suitable for use with a human monoclonal antibody or antibody fragment may be used to detect squalene antibodies. Preferred assays are a radioimmunoassay and ELISA.

The present invention also includes detecting a human antibody that specifically binds to or reacts with squalene. In preferred embodiments of the invention, the monoclonal antibody binds to squalene but not squalane (hydrogenated form of squalene).

The present invention also includes a method for detecting human squalene antibodies. The present invention also includes a method for selectively detecting the squalene antibodies, i.e., differentiating between squalene antibodies and squalane antibodies.

The present invention also contemplates a kit for detecting human squalene antibodies, said kit including one or more of the following: components used for a radioimmunoassay; components used for ELISA; one or more monoclonal antibodies; one or more antibody fragments; one or more washes; one or more buffers; one or more detection agents or labels, including but not limited to peroxidase; and one or more solid supports configured and suitable for use with the particular assay being conducted. A diagnostic kit may be designed to aid the performance of the above method. Such a kit may contain vessels containing squalene and the indicator regent, respectively.

Exemplary solid supports include but are not limited to polystyrene or polyvinyldiene fluoride (PVDF).

The description of such elements from the prior disclosure contained in the '389 application is now reiterated.

Exemplary binding agents include, but are not limited to: monoclonal antibodies ("MAb"); chimeric monoclonal antibodies ("C-MAb"); humanized antibodies; genetically engineered monoclonal antibodies ("G-MAb"); fragments of monoclonal antibodies (including but not limited to "F(Ab)$_2$", "F(Ab)" and "Dab"); single chains representing the reactive portion of monoclonal antibodies ("SC-MAb"); antigen-binding peptides; tumor-binding peptides; a protein, including receptor proteins; peptide; polypeptide; glycoprotein; lipoprotein, or the like, e.g., growth factors; lymphokines and cytokines; enzymes, immune modulators; hormones, for example, somatostatin; any of the above joined to a molecule that mediates an effector function; and mimics or fragments of any of the above. The binding agent may be labeled or unlabeled.

A binding agent according to the invention is preferably a monoclonal or polyclonal antibody. The antibody includes, but is not limited to native or naked antibodies; modified antibodies, such as activated or photoactivated antibodies. As used herein, native refers to a natural or normal antibody; naked refers to removing a non-native moiety, e.g., removing the label from a labeled antibody.

Methods for producing and obtaining an antibody are well known by those skilled in the art. An exemplary method includes immunizing any animal capable of mounting a usable immune response to the antigen, such as a mouse, rat, goat sheep, rabbit or other suitable experimental animal. In the case of a monoclonal antibody, antibody producing cells of the immunized animal may be fused with "immortal" or "immortalized" human or animal cells to obtain a hybridoma which produces the antibody. If desired, the genes encoding one or more of the immunoglobulin chains may be cloned so that the antibody may be produced in different host cells, and if desired, the genes may be mutated so as to alter the sequence and hence the immunological characteristics of the antibody produced. Fragments of binding agents may be obtained by conventional techniques, such as by proteolytic digestion of the binding agent using pepsin, papain, or the like; or by recombinant DNA techniques in which DNA encoding the desired fragment is cloned and expressed in a variety of hosts. Irradiating any of the foregoing entities, e.g., by ultraviolet light will enhance the immune response to a multi-epitopic antigen under similar conditions. Various binding agents, antibodies, antigens, and methods for preparing, isolating, and using the binding agents are described in U.S. Pat. No. 4,471,057 (Koprowski), U.S. Pat. No. 5,075,218 (Jette, et al.), U.S. Pat. No. 5,506,343 (Fufe), and U.S. Pat. No. 5,683,674 (Taylor-Papadimitriou, et al), all incorporated herein by reference. Furthermore, many of these antibodies are commercially available from Centocor, Abbott Laboratories, Commissariat a L'Energie Atomique, Hoffman-LaRoche, Inc., Sorin Biomedica, and FujiRebio.

The compositions and methods of the present invention are suitable for use in any immunoassay capable of detecting a human antibody or the like bound to an antigen. Exemplary assays include labeled binding reagent assays, including non-competitive and competitive binding assays, including assays in which the solid phase is the binding reagent or the ligand, and sandwich assays, including precipitation, radioimmunoassay, or enzyme-linked immunosorbent assay. It is intended that the invention is not to be limited by the type of immunoassay employed or the specific protocol used in performing the assay. Exemplary immunoassays techniques are shown in the Examples.

The squalene provided in the above method may be immobilized on a solid support., The solid support may be provided in one of many different forms. These forms may include a membrane, filter, plastic, bead, agarose bead, SEPHAROSE (SEPHAROSE is a registered trademark of Pharmacia Biotech, Piscataway, N.J.) Bead, or magnetic bead.

In addition to the different forms, the solid support may be made from a variety of materials. The solid support is preferably nitrocellulose, polyvinylidene difluoride, nylon, rayon, cellulose acetate, agarose, SEPHAROSE, metal, polypropylene, polyethylene, polystyrene, polyvinyl chloride, polyvinyl acetate, polyamide, polyimide, polycarbonate, polyether, polyester, polysulfono, polyacetal, or polymethyl methacrylate, more preferably is polypropylene, polystyrene, polyvinylchloride, polyamide, polycarbonate, polyether, polymethyl methacrylate, nitrocellulose, polyvinylidene difluoride, or nylon, and most preferably is nitrocellulose.

The squalene may generally be from any source. Commercial preparations are readily available (Sigma, St. Louis, Mo.). Alternatively, it may be synthesized from various precursors or obtained from an organism. Squalene is a relatively large hydrocarbon which may contain multiple antigenic epitopes. As a result any portion of squalene containing an antigenic epitope may be used in place of squalene in the present invention.

It is preferred that during the assay process, substantially all or at least one predetermined ligand or ligand receptor remains in a predetermined position. Any technique for immobilizing a ligand or ligand receptor is included in the scope of the present invention. In a preferred embodiment, a ligand or ligand receptor is bound or immobilized on or in a solid phase. Typical immobilization mechanisms include, but are not limited to, covalent binding, non-covalent binding, chemical coupling, physical entrapment, and adsorption.

Included within the scope of the present invention is changing or incorporating different surface properties on the membrane in order to achieve a desired result, e.g., the surface properties of a membrane designed for a competitive binding assay for a hormone may be different than an immunometric assay for a therapeutic drug. For example, it has been shown that treating the surface of a hydrophilized PVDF membrane with ethanolamine reduces the non-specific binding of the membrane surface. Selection of a particular surface treatment agent or surface property may be based on the desired chemical characteristic to be imparted to the surface; the inability or reduced capability of denaturing or impairing the functionality of a bioactive agent on or in the reaction zone; the desire to effect a certain orientation of an immobilized bioactive molecule; the desire to promote long-term stability of an immobilized bioactive molecule; the inclusion of a desired nucleophilic substituent; and the availability and cost of treatment agents. The use of other surface treatment agents, including bifunctional or multi-functional reagents, to affect the surface properties of the membrane are included within the present invention.

There are many other suitable detection methods compatible with the instant invention. In each case, the detection agent and its method of use are well known to one of ordinary skill in the art. The indicator reagent is typically conjugated to a detectable label. The detectable label may be an enzyme, such as alkaline phosphatase, β-galactosidase, or peroxidase; a protein, such as biotin or digoxin; a fluorochrome, such as rhodamine, phycoerythrin, or fluourescein; a fluorescent protein, such as GFP or one of its many modified forms; a radioisotope; or a nucleic acid segment. Enzymes, such as horseradish peroxidase, alkaline phosphatase, and β-galactosidase, may also be used as detection labels. Detection agents for enzymes generally utilize a form of the enzyme's substrate. The substrate is typically modified, or provided under a set of conditions, such that a chemiluminescent, colorimetric, or fluorescent signal is observed after the enzyme and substrate have been contacted (Vargas, et al. Anal Biochem 209: 323, 1993).

A signal-producing agent refers to any agent or marker which produces a detectable signal or which permits the detection of a ligand or ligand-receptor. Preferred signal-producing agents are those which permit detection of the analyte without instruments, preferably by visual means. Exemplary signal-producing agents include, but are not limited to color forming agents, such as an enzyme, polymer containing dyes, chemiluminescent agents, fluorescent agents, radioisotopes or ferromagnetic particles. The color forming agent may be a colored particle, a colored molecule or some species, such as an enzyme, which is capable of triggering a sequence of events leading to the formation of a colored marker. The colored molecule may be a fluorescent dye, such as fluorescein, rhodamine or alexa flour; a chemiluminescent compound; a bioluminescent compound; or a compound that may be detected by the absorption of electromagnetic radiation (and possible reemission of radiation at another wavelength), including ultraviolet radiation, visible radiation and infrared radiation. The colored molecule may be directly or indirectly conjugated to a ligand or ligand-receptor. Alternatively, the colored molecule may be incorporated in a particle, particularly a microsome.

Enzymes, useful as color forming agents, include alkaline phosphatase, horseradish peroxidase or B-galactosidase. Such enzymes are often used in conjunction with a chromogenic substrate.

In the methods of the invention, it may be desirable to control or specify the amount of squalene bound to the solid support. Determining the appropriate amount of squalene for a particular assay is well within the capability of one skilled in the art. The present inventors have found that, for the murine assays shown in the Examples, up to about 100 nmol, preferably between about 7.5 and about 100 nmol, and most preferably, between about 10 and about 25 nmol of squalene yields a reproducible assay. For the human assays shown in the Examples, up to about 500 nmol, preferably between about 7.5 and about 100 nmol, and most preferably, between about 7.5 and about 20 nmol of squalene yields a reproducible assay.

Novel Aspects of the Present Invention

Turning now to the human squalene antibody detection specifically, the improvement represented by the present invention of which the interpretive results are first presented.

Effects of Blocking Agents on the ELISA

Several different blocking and diluent agents were investigated for use in developing the ELISA for human samples. In the absence of primary antibody, either 0.5% casein (CASEIN) or 0.6% gelatin (GEL/CASEIN) as blockers followed by 0.5% casein as the diluent, worked best for blocking of binding of the peroxidase-linked anti-human IgG (FIG. 23A) and anti-human IgM (FIG. 23B) to the plate. The binding of peroxidase-linked anti-human IgG and anti-human IgM to SQE-coated wells was only slightly elevated when 4% FBS was used as blocker and diluent. Due to concern that the SQE, which is known to be present in lipoprotein, might inhibit the binding of anti-SQE antibodies to SQE-coated wells, FBS was not considered for further use. Based on these data, 0.5% casein was chosen as the best diluent for human serum and the secondary antibodies.

In order to determine the best blocking agent, wells either were coated with SQE or not coated with SQE (ISP treatment alone) and then blocked with 0.6% gelatin or 0.5% casein. Human serum was diluted in 0.5% casein and plated on the wells A control human monoclonal IgG (IM-9) did not bind to control (ISP-treated) or SQE-coated wells when 0.6% gelatin or 0.5% casein were used as the blocking agent (FIG. 24A,B). 0.6% gelatin did not effectively block the binding of human serum IgG antibodies to control (ISP-treated) wells (FIG. 24A). Absorbance values for serum numbers 39, 43, 99, and 109 were >1.0, when incubated on control wells. Furthermore, when 0.6% gelatin was used as the blocker, the absorbance of serum IgG antibodies binding to SQE-coated wells was detectable, but was only slightly above that of control wells (FIG. 24A). In contrast, when 0.5% casein was used as the blocker, the binding of serum IgG antibodies to control wells was greatly reduced for all sera studied (FIG. 24B). The absorbance for serum IgG antibodies incubated on SQE-coated wells was readily detectable when 0.5% casein was used as the blocker (FIG. 24B). Consequently, 0.5% casein was used in all further experiments for the measurement of IgG antibodies to squalene in human serum.

Gelatin and casein were also tested as blocking agents for the measurement of serum IgM antibodies to SQE (FIGS. 24C,D). Control human IgM monoclonal antibody (RPMI 1788) did not bind to control (ISP-treated) or SQE-coated wells with either the casein or gelatin blocker (FIGS. 24C,D). The absorbances for serum containing IgM antibodies incubated on control wells were essentially the same for gelatin and casein blocked wells (FIGS. 24C,D; open bars). However, the absorbance of serum containing IgM antibodies incubated on SQE-coated wells was dramatically higher when the casein blocker was used than when gelatin was used as a blocker (FIGS. 24C,D; solid bars). Consequently, casein was chosen as the preferred blocker for the ELISA assay on human IgM antibodies to SQE.

Effect of the Amount of SQE Coated on the Well

The binding of human serum antibodies to SQE-coated wells was dependent upon the amount of SQE (FIG. 25). Three types of binding curves were observed. The first type had an optimal absorbance range in which the absorbance increased with SQE, reached a plateau, and then decreased (FIGS. 25A,D). The plateau region typically ranged from 5-50 nmol, but was dependent upon the serum assayed. The second type was relatively independent of SQE (FIG. 25B). The third type of curve continued to increase in absorbance over the entire range of SQE assayed (FIG. 25C). These three types of absorbance curves were observed for both IgG and IgM. Because the absorbances at 20 nmol were high in all of the serum assayed, 20 nmol was chosen as the optimal amount of SQE to use for the detection of antibodies to SQE in human serum.

Antibody Binding to SQE in Human Cohorts

When serum samples were assayed for antibodies to SQE, seven types of IgG (FIG. 26) or IgM (FIG. 27) binding patterns were observed. 1) Sera were positive for IgG antibodies to SQE (FIG. 26; sera 43, 329). Absorbances for serum IgG binding to SQE-coated wells were elevated above control wells at more than one dilution of serum. 2) Sera were negative for IgG antibodies to SQE (FIG. 26; sera 108). Absorbances for serum IgG binding to SQE-coated wells were not different from control wells, which had very low absorbance (FIG. 26, serum 108). 3) Absorbances for serum IgG binding to SQE-coated wells were elevated at only the 1:25 dilution (FIG. 26; serum 336) and were considered negative. 4) Sera were positive for IgM antibodies to SQE (FIG. 27; sera 43, 119). Absorbances for serum IgM binding to SQE-coated wells were elevated above serum IgM binding to control wells at more than one dilution of serum. Absorbances on control wells were approximately 50% of the absorbance of that on the SQE-coated wells (FIG. 27 sera 43, 119). 5) Sera contained high absorbance values for IgM binding to both control and SQE-coated wells (FIG. 27; serum 357). 6) Sera were negative for IgM antibodies to SQE (FIG. 27; sera 100, 335). Absorbances for serum IgM binding to SQE-coated wells were not different from control wells, which had very low absorbances. 7) Absorbances for serum IgM binding to SQE-coated wells were elevated at only slightly at the 1:25 dilution (not shown) and therefore were considered negative.

were highly reproducible (FIG. 27, serum 43, 357). Freeze-thaw had no effect on the measurement of antibodies to squalene (FIG. 28). Positive samples remained positive after freeze-thaw with approximately the same dilution curve (FIGS. 28A-F) and negative samples remained negative (FIGS. 28G-H). The absorbances on control wells also were not affected by freeze-thaw.

Prevalence of Antibodies to SQE in Human Sera

To establish a basis for comparison of the prevalence of antibodies to SQE in different cohorts, we defined what constitutes a positive result: A serum sample was scored as positive if it had absorbances greater than 3× baseline at two dilutions. Dilutions consisted of 1:25, 1:50, 1:100, 1:200, 1:400 and 1:800. As shown in Table 1, 42.6% of the sera assayed from the cohort from Frederick, Md. were positive for IgG or IgM antibodies to SQE. The predominant antibody to SQE was IgM which was 2-fold greater than IgG (Table I). Only 4.9% of the sera assayed from the Frederick cohort were positive for both IgG and IgM antibodies to SQE.

The Frederick cohort served as a control cohort of similar aged individuals for the USAMRIID alumni cohort. None of the individuals in the Frederick cohort had been employees at USAMRIID. There were no significant differences between these two cohorts in the prevalence of antibodies to SQE (Table I, 95% confidence interval). There is a 2-fold difference in the prevalence of IgG antibodies to SQE observed in the USAMRIID alumni (7.5%) and Frederick cohorts (15.1%), but this difference is not statistically significant ($?_1=1.69$, p=0.19). IgM antibodies to SQE were 37.5% and 32.3% for the USAMRIID and Frederick cohorts, respectively ($?_1=0.43$, p=0.51). Forty percent of the sera from the USAMRIID alumni were positive for IgG or IgM antibodies to SQE compared with 42.6% from the Frederick cohort (Table I) ($?_1=0.10$, p=0.75). Only 5% of the sera from the USAMRIID alumni and 4.9% of the Frederick cohort had both IgG and IgM antibodies to SQE (Table I) ($?_1=0.00$, p=0.97).

TABLE I

Frequency of Antibodies to SQE in Human Serum

| | SQE-Coated Wells (Percent Positive) | | | Wells Lacking SQE (Percent Positive) | | |
| --- | --- | --- | --- | --- | --- | --- |
| Antibody Type | USAMRIID (N = 40) | Frederick (N = 372) | Fort Knox (N = 299) | USAMRIID (N = 40) | Frederick (N = 372) | Fort Knox (N = 299) |
| IgG | 7.5 [1.6-20.4]* | 15.1 [11.6-19.1] | 0.0 [0.0-1.0] | 0.0 | 0.5 | 0.0 |
| IgM | 37.5 [22.7-54.2] | 32.3 [27.4-37.4] | 19.4 [15.1-24.3] | 2.5 | 7.3 | 13.0 |
| IgG or IgM | 40.0 | 42.6 | 19.4 | 2.5 | 7.8 | 13.0 |
| IgG & IgM | 5.0 | 4.9 | 0.0 | 0.0 | 0.0 | 0.0 |

Sera having absorbances of >3X baseline on SQE-coated wells or wells lacking SQE (ISP-treated) at the 1:25 and 1:50 dilutions were scored as positive.
*95% confidence intervals for binomial proportions Reproducibility of the Assay The assay was highly reproducible for both positive and negative responses for IgG (FIG. 26) and IgM (FIG. 27) antibodies to squalene. Some sera were assayed three times with similar results on each assay. Slight differences were observed in the absorbances for positive responses from assay to assay, but positive responses were always positive (FIG. 26, serum 43, 329). High absorbances on control wells also Of the 299 samples from the Fort Knox blood bank cohort, only 19.4% were scored as positive for antibodies to SQE (Table I). Compared to the samples from the Frederick cohort, the samples from the blood bank at Fort Knox had a significantly reduced prevalence of antibodies to SQE (Table I; 95% confidence interval). The most pronounced difference between the two cohorts was in IgG antibodies to SQE. There were no detectable IgG antibodies to SQE in the samples from the Fort Knox blood bank compared with 15.1% in the Frederick cohort (Table I) ($?_1$=49.25, p<0.0001). The incidence of IgM antibodies to SQE was also significantly reduced in the Fort Knox Blood Bank cohort (19.4%) compared to the Frederick cohort (32.3%) (Table I) ($?_1$=14.23, p=0.0002). It should be noted that the estimated average age of the Fort Knox cohort (age range 17-21) was considerably lower than the Frederick control or USAMRIID cohorts (mean 68, age range 58-82).

The titers of the positive samples in each of the three cohorts were generally low. Only one serum sample was positive both for IgG and IgM at the 1:100 dilution in the USAMRIID alumni. In this one serum sample, the endpoint titers were 100 for the IgG and 400 for the IgM. There was only one positive IgG serum sample out of 372 at the 1:100 dilution in the Frederick cohort, and that serum had an endpoint titer of 400. There were 27 positive IgM samples at the 1:100 dilution in the Frederick cohort. Titers ranged from 100-1600, with 12 samples having endpoint titers of 100, 4 samples having endpoint titers of 200, 3 samples having endpoint titers of 400, and 1 each with endpoint titers of 800 and 1600. Only 3 of the samples from the Fort Knox cohort had IgM endpoint titers≧100, with titers of 100, 200 and 400, respectively.

Antibodies to SQE in USAMRIID Alumni who Received Anthrax Vaccine

As a condition for employment most of the USAMRIID employees were vaccinated with anthrax vaccine AVA before access was granted to biocontainment laboratories where *Bacillus anthracis* was studied. Most of the USAMRIID alumni received several other vaccines as well as AVA through the USAMRIID special immunization program (Pittman et al., 2002). Six of the forty individuals in the cohort were not vaccinated or the AVA vaccination status was unknown, and all 6 have been removed from analysis in this section. One of the latter 6 samples removed from analysis was positive for IgG to SQE and 2 out of 6 were positive for IgM (Table II).

TABLE II

Age, Sex, AVA Doses, and Antibodies to SQE Among the USAMRIID Alumni

| ID No. | Age | Sex | AVA # Doses | SQE IgG | SQE IgM |
|---|---|---|---|---|---|
| 1 | 59 | M | 3 | 0 | 0 |
| 2 | 66 | M | 33 | 0 | 0 |
| 3 | 63 | F | 0 | 0 | 0 |
| 4 | 82 | F | 31 | Pos | Pos |
| 5 | 68 | M | Unknown | 0 | Pos |
| 6 | 71 | M | 4 | 0 | 0 |
| 7 | 69 | F | 0 | 0 | Pos |
| 8 | 59 | M | 37 | 0 | Pos |
| 9 | 72 | M | 25 | 0 | 0 |
| 10 | 70 | M | Unknown | Pos | 0 |
| 11 | 66 | M | 47 | Pos | Pos |
| 12 | 65 | M | 16 | 0 | 0 |
| 13 | 79 | M | 27 | 0 | Pos |
| 14 | 70 | M | 0 | 0 | 0 |
| 15 | Unknown | M | 41 | 0 | 0 |
| 16 | 60 | M | 24 | 0 | 0 |
| 17 | 74 | M | 39 | 0 | Pos |
| 18 | 59 | M | 14 | 0 | 0 |
| 19 | 65 | M | 40 | 0 | Pos |
| 20 | 75 | M | 28 | 0 | 0 |
| 21 | 68 | M | 20 | 0 | Pos |
| 22 | 69 | M | 15 | 0 | 0 |
| 23 | 64 | F | 8 | 0 | Pos |
| 24 | 72 | M | 32 | 0 | Pos |
| 25 | 70 | M | 31 | 0 | Pos |
| 26 | 61 | F | 8 | 0 | 0 |
| 27 | 71 | M | 30 | 0 | 0 |
| 28 | 58 | M | 26 | 0 | 0 |
| 29 | Unknown | M | 35 | 0 | 0 |
| 30 | 70 | M | 36 | 0 | 0 |
| 31 | 76 | M | 36 | 0 | 0 |
| 32 | 78 | M | 33 | 0 | 0 |
| 33 | 67 | M | 27 | 0 | 0 |
| 34 | 71 | M | 29 | 0 | 0 |
| 35 | 59 | M | Unknown | 0 | 0 |
| 36 | 64 | M | 14 | 0 | 0 |
| 37 | 71 | M | 45 | 0 | Pos |
| 38 | Unknown | M | 9 | 0 | Pos |
| 39 | 70 | M | 24 | 0 | 0 |
| 40 | 72 | M | 20 | 0 | Pos |

The mean number of doses of AVA that had been administered to the remaining individuals was 26 (range 3-47 doses) (Table II). After removal of the 6 samples, the prevalence of antibodies to SQE was basically unchanged from that shown in Table 1 for the USAMRIID alumni. 5.7% were positive for IgG or both IgG and IgM antibodies to SQE. 37.1% were positive for IgM alone or IgG or IgM antibodies to squalene. There were no statistical differences between the USAMRIID alumni who received AVA and the controls of similar ages from Frederick (IgG—$?_1$=2.3, p=0.13; IgM—$?_1$=0.33, p=0.56; IgM—$?_1$=0.39, p=0.53). Analyses of the health information from the USAMRIID alumni revealed no obvious relationship between the health of the individuals and antibodies to SQE. Many of the individuals in both the USAMRIID and the Frederick control cohorts did have various illnesses or chronic diseases, but this was expected to be the case for any cohort from the general population with an average age of approximately 68 and an age range of 58-82.

Increased Prevalence of Antibodies to SQE in Women

The Frederick cohort contained 230 males and 142 females. There were 35 males and 5 females in the USAMRIID cohort. The data from these two cohorts were combined for analysis of the effect of sex on the prevalence of antibodies to SQE. Thus, there were 265 males and 147 females enrolled in the study. Thirty-three (12.5%) of the male samples and 26 (17.7%) of the female samples were positive for IgG antibodies to SQE. There was no statistical difference in the prevalence of IgG antibodies to SQE between males and females ($?_1$=2.07, p=0.15). However, there was a statistically significant increase in prevalence of IgM antibodies to SQE in females as compared to males. Seventy-five (28.4%) of the male samples and 60 (40.8%) of the female samples were positive ($?_1$=6.72, p=0.01). Female subjects were 1.75 times more likely to be positive for IgM antibodies to SQE (95% confidence interval on the odds ratio: lower limit=1.14, upper limit=2.66). Similarly, females were 1.67 times more likely to be positive for IgG or IgM antibodies to SQE (95% Cl on the odds ratio: 1.11, 2.51). There were 100 (37.7%) samples from males and 74 (50.3%) samples from females having either IgG or IgM antibodies to SQE ($?_1$=6.16, p=0.013). In order to ensure that this observed increase in prevalence of antibodies to SQE in females did not alter the conclusions drawn from the comparison of the USAMRIID and Frederick cohorts as homogeneity of Odds Ratio test was conducted but no modification was necessary.

Antibody Binding to Wells Lacking SQE

In assaying sera for antibodies to SQE, absorbances to wells lacking SQE served as controls. However, upon examination of all of the human samples assayed (n=711), absorbances for IgM antibodies binding to control wells were elevated at the 1:25 and 1:50 dilutions in 32.5 and 9.4%, of the samples respectively. In contrast, only 2.9% (1:25 dilution) and 0.3% (1:50 dilution) of the samples assayed were elevated for IgG antibodies binding to control wells. Overall, these elevations typically were approximately 50% of the absorbance levels observed for binding to SQE-coated wells (FIG. 27, sera 43 and 119). In a small number of samples, the absorbances for control wells were almost equal to the absorbance for SQE-coated wells (FIG. 27, serum 357). These elevations in absorbance in control wells lacking SQE were invariably observed only in samples which also were scored as positive for antibodies to SQE. When culture supernatants containing human monoclonal IgG or IgM antibodies to other antigens were assayed in the SQE ELISA, no binding was detected either to control or SQE-coated wells (FIGS. 29A-D, F), except for the antibody from the clone that secretes an IgM antibody to lipid A (FIG. 29E). This latter monoclonal antibody bound to SQE-coated wells, but not to control wells.

The binding of the latter monoclonal anti-lipid A antibody to SQE was approximately 10% of the binding of the antibody to lipid A (data not shown). The above data suggest that antibody binding to control wells was not due to a nonspecific interaction between the polystyrene well and the antibody. Although the precise region of cross-reactivity of the anti-lipid A monoclonal antibody between lipid A and SQE is unknown, several possible regions of similarity could be identified. In any case, the existence of the binding specificity to SQE by this human monoclonal antibody permitted its use as a positive control for standardizing and validating the assays with unknown human serum samples.

In order to investigate the nature of the elevated absorbance on control wells, diluted serum was plated on ISP-treated wells lacking SQE, or on SQE-coated wells, to adsorb the antibodies. After two rounds of adsorption, the supernatant was placed on ISP-treated wells lacking SQE or on SQE-coated wells, followed by ELISA. Two rounds of absorption removed both the polystyrene and SQE binding activities from serum 243 (FIG. 30A). Absorption on ISP-treated control wells lacking SQE greatly diminished the binding of serum 357 to SQE-coated wells (FIG. 30B).

Antibodies to SQE in Mouse Serum

IgG and IgM antibodies to SQE were not observed in the individual sera of 2-month old mice in any of the strains studied (Table II). However, many individual mice developed either IgG or IgM antibodies to SQE as a function of time (Table II). The degree of tendency to develop antibodies was strain specific: C57BL/6>B10.BR>/BALB/c.

TABLE III

Appearance of Antibodies to SQE in Mouse Serum as Function of Age

| Age (months) | BALB/c % positive (# positive/total) [95% confidence interval] | | B10.Br % positive (# positive/total) [95% confidence interval] | | C57BL/6 % positive (# positive/total) [95% confidence interval] | |
|---|---|---|---|---|---|---|
| | IgG | IgM | IgG | IgM | IgG | IgM |
| 2* | 0 (0/49) [0.0-5.9] | 0 (0/60) [0.0-4.9] | 0 (0/25) [0.0-11.3] | 0 (0/25) [0.0-11.3] | 0 (0/25) [0.0-11.3] | 0 (0/25) [0.0-11.3] |
| 10 | 11 (2/18) [1.4-34.7] | 32 (6/19) [12.6-56.6] | 0 (0/18) [0-15.3] | 10.5 (2/19) [1.3-33.1] | 12 (2/17) [1.5-36.4] | 30 (6/20) [11.9-54.3] |
| 16 | 10 (2/19) [1.3-33.1] | 37 (7/19) [16.3-61.6] | 10 (2/20) [1.2-31.7] | 0 (0/20) [0.0-13.9] | 74 (14/19) [48.8-90.9] | 90 (18/20) [68.3-98.8] |
| 17 | 0 (0/19) [0.0-14.6] | 63 (12/19) [38.4-83.7] | 5 (1/20) [0.1-24.9] | 5 (1/20) [0.1-24.9] | 65 (13/20) [40.8-84.6] | 80 (16/20) [56.3-94.3] |
| 18 | N.D. | 39 (7/18) [17.3-64.3] | 85 (17/20) [62.1-96.8] | 5 (1/20) [0.1-24.9] | 100 (17/17) [83.8-100] | 89 (16/18) [65.3-98.6] |
| 19 | 6 (1/17) [0.1-28.7] | 65 (11/17) [38.3-85.8] | 60 (12/20) [36.1-80.9] | 25 (5/20) [8.7-49.1] | 100 (18/18) [84.7-100] | 72 (13/18) [46.5-90.3] |
| 21 | 10 (1/10) [0.3-44.5] | 62 (8/13) [31.6-86.1] | 45 (9/20) [23.1-68.5] | 55 (11/20) [31.5-76.9] | 94 (16/17) [71.3-99.9] | 62 (10/16) [35.4-84.8] |
| 24 | 17 (1/6) [0.4-64.1] | 86 (6/7) [42.1-99.6] | 0 (0/17) [0.0-16.2] | 50 (9/18) [26.0-74.0] | 46 (6/13) [19.2-74.9] | 58 (7/12) [27.7-84.8] |
| At any time point | 35 (7/20) | 85 (17/20) | 95 (19/25) | 65 (13/20) | 100 (20/20) | 100 (20/20) |

Mice were bled at the time intervals indicated and the sera were assayed for antibodies to SQE. Serum was scored as positive for IgG or IgM antibodies to SQE if the absorbance was >3 times the baseline at both the 1:50 and 1:100 dilutions. Baseline absorbances ranged from 0.1-0.18 in different assays.
*Sera from 2 month old mice were from different animals than the retired breeders used for the remaining time points.

The incidence of IgG antibodies to SQE was 100% at 18-19 months of age for the C57BL/6 mice. B10.Br had a maximal incidence of 85% at 18 months of age. This incidence decreased for both strains, with none of the B10.Br mice testing positive, and 46% for the C57BL/6 mice testing positive, at 24 months of age. Ninety-five and 100% of B10.Br and C57BL/6 mice, respectively, tested positive for IgG antibodies to SQE some time during the course of the experiment. Only a low incidence of IgG antibodies to SQE was observed in the serum of BALB/c mice, and low absorbances with positive sera were only slightly above three times baseline. Although 35% of BALB/c mice tested positive for IgG antibodies to SQE at some time in the course of the experiment, this only occurred at one time point for each positive mouse.

As with IgG antibodies, IgM antibodies to SQE were not observed in the serum from mice at 2 months of age (Table III). The prevalence of mouse serum testing positive for IgM antibodies to SQE increased with the age of the mice in all three strains assayed. There was a higher incidence of IgM antibodies to SQE in the BALB/c and C57BL/6 stains as compared to the B10.Br mice, and the IgM antibodies to SQE were observed earlier in the BALB/c and C57BL/6 mouse sera than the B10.Br mouse sera. Only 65% of the B10.Br mice were positive for IgM antibodies to SQE sometime during the experiment. In contrast, 85% and 100% of BALB/c and C57BL/6 mice, respectively, developed IgM antibodies to SQE.

Although the data in Table III is not designed to illustrate the titers of the IgG or IgM antibodies to SQE, endpoint titers (absorbance>3× assay baseline) of positive samples, when examined in detail, were typically 100-400. However, a small number of samples were observed to have positive absorbances at a 1:800 dilution (highest dilution assayed). There were 3 types of individual animal responses for antibodies to SQE. 1) Animals were negative for IgG or IgM antibodies to SQE (FIGS. 31A,C,D). 2) Animals were initially negative for antibodies to SQE and later developed antibodies to SQE which remained elevated (FIGS. 31B, E-H). 3) Animals were initially negative or slightly positive for antibodies to SQE developed higher titers to antibodies to SQE and then became negative for antibodies to SQE at later time points (FIGS. 31I-J). There was no observed relationship between IgG and IgM antibodies to SQE. Twenty-two animals died during the course of the experiment with the deaths occurring after 17 months of age. Most of the deaths occurred in the BALB/c mice. There appeared to be no relationship between antibodies to squalene and death. As with the human serum, some of the mouse sera had elevated absorbances on control wells. This was observed for both IgG and IgM antibodies (FIG. 31).

Discussion

A highly reproducible, high throughput, and quantitative assay for measuring antibodies to SQE in human serum is described. The assay was modified from a previously described assay for murine antibodies to SQE (Matyas et al., 2002). Like the mouse assay, the human assay used Costar tissue culture 96 well plates, which were plates that are not routinely used for ELISA assay. As with murine antibodies to SQE, none of the standard ELISA plates were useful for this human SQE antibody assay (data not shown). The use of the standard ELISA plates resulted in high background absorbances in control (ISP-treated) wells.

The murine assay used BSA as a blocker/diluent. However, BSA did not effectively block the binding of peroxidase-linked anti-human IgG and IgM to SQE-coated plates. Casein effectively blocked this non-specific binding in the human assay. The optimal amount of SQE added to the plates was similar for both the human and mouse assays. The human assay used 20 nmol of SQE and the mouse assay used 15 nmol. The quantification of the amount of SQE bound to the wells under the conditions used in the human antibody assay was virtually identical to that described for the mouse (Matyas et al., 2002). In the mouse assay, the primary serum was incubated on the assay plate for 1 h. Early experiments during assay development suggested that an increased incubation time (overnight) increased the sensitivity of the assay for human antibodies. The optimal dilution of the secondary antibody was determined to be 1:1000 (data not shown). There were no differences observed with different lots of plates (data not shown).

Elevated absorbances were observed on control wells of some of the samples testing positive for antibodies to SQE in both the human and mouse serum (FIG. 24D; FIG. 26—sample 43; FIG. 27—samples 43, 119 and 357; FIGS. 28C,D; and FIGS. 31B,E,G,H,I,J). This was most prevalent for IgM antibodies at 1:25 and 1:50 dilutions for the human and mouse samples, respectively. This was not a result of the ISP treatment itself, since similar results were obtained when control wells were untreated. Furthermore, only 32.5% of the human samples that were positive for antibodies to SQE had elevated absorbances on control wells. With any given serum, absorbance in the control wells never exceed those found in the SQE-coated wells.

Figure 1:
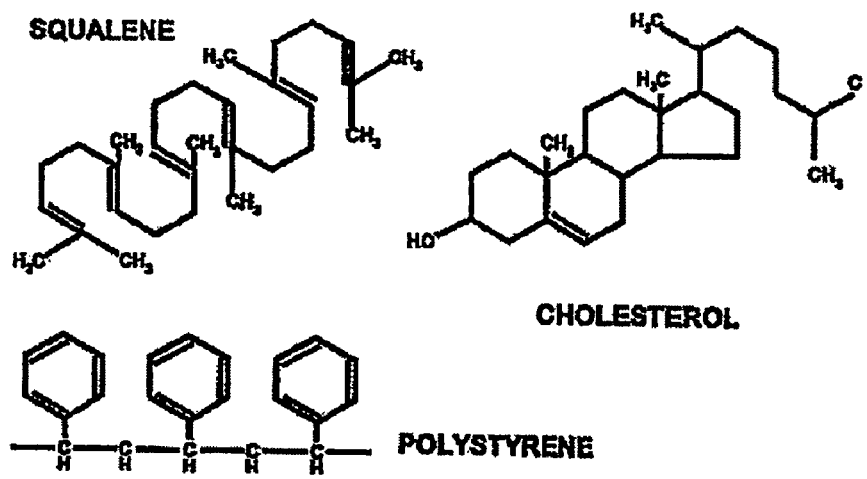

In view of the foregoing, it is reasonable to deduce that the above binding of SQE-positive serum samples to the control wells was due to crossreactivity of SQE antibodies to polystyrene. This is supported by the following evidence. 1) None of the samples that tested negative for antibodies to SQE from humans or mice had elevated absorbances on control wells. 2) As shown in FIG. 27, human monoclonal IgG or IgM antibodies did not bind nonspecifically to control wells (ISP-treated). Two additional antibodies, one IgG and one IgM, (not shown) were also assayed and no reactivity was observed to control wells or SQE-coated wells. Similarly, control murine monoclonal antibodies (six IgM antibodies) did not have elevated absorbances on control wells (Matyas et al., 2000, 2002; data not shown). 3) Pre-incubation of serum for two rounds on ISP-treated wells removed not only the absorbance seen on control wells, but also effectively all of the SQE binding activity (FIG. 9). Thus, it appears that the binding to control wells was a specific binding of IgG and IgM antibodies to the wells. 4) Polystyrene is a polymer of styrene ($CH_2=CH-C_6H_6$) (FIG. 1), and sterilization of the cell culture plates by gamma irradiation can lead to cleavage of one or more of the double bonds in the benzyl rings and the hydrocarbon backbone. Gamma irradiation may also induce fusion of the benzyl rings. Consequently, irradiated polystyrene may have elements that are structurally similar to SQE in that irradiated polystyrene has open ring structures that still contain double bonds. One interesting possibility may be that the observed antibodies to SQE may be antibodies to polystyrene that cross-react with SQE. Styrene is a widespread environmental contaminant that is particularly derived from cigarette smoke or is present in food after having been leached from polystyrene food containers, especially containers containing yoghurt or fat products (Newbook and Caldwell, 1993). Although there is no direct evidence for the induction of antibodies to styrene or polystyrene, the structural similarities of styrene and polystyrene with SQE (FIG. 1) raise this as a hypothetical possibility.

Sera from three human cohorts were assayed for antibodies to SQE. Antibodies to SQE were detected in some of the samples in all three cohorts. The volunteers from Frederick were an age-restricted cohort from Frederick, Md.: The presence of antibodies to SQE in this cohort implies that antibodies to SQE are a naturally occurring phenomenon in humans.

This is not surprising, since previous studies have demonstrated naturally occurring human antibodies to cholesterol (Alving et al., 1989) and to phospholipids (Alving, 1984). Naturally-occurring antibodies to cholesterol have been found in essentially 100% of volunteers studied (Alving and Wassef, 1999). Antibodies to cholesterol do not appear to have an adverse impact on health and may play a role in the regulation of LDL (Alving and Wassef, 1999). Since SQE is present on LDL particles in plasma, it is possible that naturally occurring antibodies to SQE may also contribute to the regulation of LDL.

Although no IgG antibodies to SQE were detected in the sera from the Fort Knox cohort, 7.5 and 15.1% of the samples from the USAMRIID alumni and Frederick cohorts, respectively, were positive for IgG antibodies. With respect to IgM, the samples from the USAMRIID alumni and the Frederick cohorts were 37.5 and 32.3% positive, respectively, while the Fort Knox samples were 19.4%. It should be noted that there is a 9.3-fold difference between the number of volunteers in the USAMRIID alumni (N=40) and the Frederick cohort (N=372). The low number of volunteers in the USAMRIID alumni greatly reduced the power to determine significant differences between the two cohorts. The samples from the USAMRIID alumni and the Frederick cohorts were from volunteers >58 years old. Compared to the Frederick cohort, the prevalence of both IgG and IgM antibodies to SQE was significantly reduced in the Fort Knox cohort. Although no individual age information was available from the volunteers of the Fort Knox cohort, the demographics of the volunteer population at the Camp Memorial Blood Center, Fort Knox (85% of the individuals are17-20 years of age) suggested to us that antibodies to SQE may increase as a function of age.

There are numerous circumstances in which natural antibodies are related to age. One example of this is that reported by Pinto and Rimon (1970) that demonstrated the presence of antibodies to hydrocortisone hemisuccinate in 26% of the serum samples from normal human adults aged 25-65; but in only 3% of infants 9 months-3 years of age. In support of this hypothesis, it was noted that young mice (2 months old) had no antibodies to SQE. Ten month old mice had a 10-30% incidence of antibodies to SQE. The incidence increased as a function of age, with 100% of the C57BL/6 mice testing positive for antibodies to SQE at 18 and 19 months of age. This mouse study also demonstrated that antibodies to SQE developed naturally without vaccination with AVA or other vaccines. The development of antibodies to SQE varied with the strain of the mouse, thus suggesting that genetic factors may also be involved.

Thirty-four volunteers from the USAMRIID alumni cohort had been immunized with the anthrax vaccine AVA. Most had received numerous vaccinations (mean=26 doses, range 3-47 doses). Comparison of the AVA-immunized USAMRIID alumni with the similar aged cohort from the normal population of Frederick, none of whom received AVA, revealed that immunization with AVA did not significantly increase the prevalence of antibodies to SQE (IgG—?$_1$=2.3, p=0.13; IgM—?$_1$=0.33, p=0.56; IgG or IgM—?$_1$=0.39, p=0.53). Although not significant, the prevalence of IgG antibodies to SQE in the AVA immunized group (5.1%) was approximately 3-fold less than the unimmunized Frederick control group. Asa et al., (2002) also found that there was no statistical difference in the incidence of antibodies to SQE between AVA immunized and unimmunized individuals. They also reported a 15.8% prevalence of IgG antibodies to SQE in their controls, which was similar to the 15.1% prevalence of IgG antibodies to SQE in the Frederick cohort. However, no IgG antibodies to SQE were observed in the Fort Knox cohort. Asa et al., (2002) did not report the age of their control population, but in the data presented herein includes a control group with a similar age distribution to that of the AVA immunized group.

The existence of naturally-occurring antibodies to SQE raises the issue of whether such antibodies are produced as a result of immunization with SQE (for example, SQE present as a contaminant of AVA), or by immunization with a substance similar to SQE in the environment that might induce cross-reacting antibodies. Induction of antibodies to SQE by SQE contaminants of AVA or other vaccines seems highly unlikely. Using an HPLC assay with a detection limit of 70 ng/ml, Spanggord et al., (2002) reported that squalene was not present in 17 different lots of AVA. However, the FDA provided written testimony to Congress that several lots of AVA and several other vaccines had squalene contamination in the "low parts per billion" (ng/ml) as detected by gas chromatography (Metcalf, 2000). The data from which these latter determinations were not provided to Congress, nor were the experiments published in the scientific literature, making the scientific validity of the testimony difficult to evaluate. However, even if the FDA data were correct and an individual was given 10 ng of SQE in an AVA dose, it is difficult to believe that this minute amount of SQE contaminant could induce antibodies to SQE. As has been previously reported, there exists an inability to induce antibodies to SQE in mice with multiple immunizations with large amounts of SQE alone or mixed with alum and other potent adjuvants and immuno-stimulatory formulations (Matyas et al., 2000). Only with 2 of 8 formulations were low to moderate titers of IgM antibodies to SQE observed. No IgG antibodies to SQE were observed. Furthermore, the amount of SQE present as an infinitesimal contaminant in vaccines or other injectables pales by comparison with the huge amounts of SQE that are normally continually synthesized and that are present in skin and liver, and normally circulating in blood. It has been hypothesized that naturally-occurring antibodies to cholesterol might be derived from inflammatory processes involving the skin (Alving and Wassef, 1999), and antibodies to SQE might be derived in a similar manner.

Although increased prevalence of natural antibodies is often seen in the serum of women, increased prevalence of antibodies to SQE was an unanticipated finding in the present study. However, this increased prevalence of antibodies to SQE in females did not alter the conclusions drawn between the Frederick and USAMRIID (and AVA subcohort), since the crude and gender adjusted odds ratios estimated using logistic regression for IgG, IgM and IgG or IgM antibodies to SQE were not significant. It is unclear as to the reasons for this increased prevalence in women. One possibility may be that some women may have developed antibodies to steroid sex hormones such as progesterone, testosterone or estrogens and that these antibodies may cross-react with SQE. Antibodies to estradiol (Counihan et al., 1991), 16-a-hydroxyestrone (Bucala et al., 1987) and ethinylestradiol (Beaumont et al., 1989) were reported in sera from women who used oral contraceptives or had systemic lupus erythematosus. Patients with systemic lupus erythematosus also were reported to have antibodies to β-estradiol (Mionuddin, 1998). Antibodies to testosterone have been reported in a woman with hypergonadotropic hypogonadism (Kuwahara et al., 1998). Furthermore, using human lymphocyte-derived DNA libraries, antibodies to digoxigenin, estradiol, testosterone and progesterone were found (Dorsam et al., 1997). Since the steroid sex hormones are synthesized from cholesterol (which, in turn, is synthesized from SQE) and since they have the fused cholesterol ring structure, antibodies to these hormones may cross-react with SQE. Murine monoclonal antibodies to steroid hormones have been extensively studied (Franek, 1987; Grover and Odell, 1977). They generally cross-reacted to varying degrees with a small number of other steroid hormones (Fanti and Wang, 1984; Mais et al., 1995; Brochu et al., 1984). Limited analysis of the specificity of murine monoclonal antibodies to SQE (Matyas et al., 2000 and 2002) indicated that some of the clones cross-reacted with cholesterol and/or testosterone (unpublished data).

EXAMPLES

Materials and Methods for Detection of Mouse Antibodies to Squalene

Lipids

Squalene, squalane oils, and bovine serum albumin (essentially fatty acid free; cat. # A-7030) (BSA) were purchased from Sigma-Aldrich Chemical Company, St. Louis, Mo. Isopropanol was purchased from J. T. Baker, Phillipsburg, N.J. Emulsifiers for creating oil-in-water emulsions consisted of Span 85 and Arlacel A (both from Sigma) and Tween 80 (Aldrich Chemical Co., Milwaukee, Wis.). Dimyristoyl phosphatidylcholine (DMPC) and dimyristoyl phosphatidylglycerol (DMPG), both used in the formation of liposomes, were purchased from Avanti Polar Lipids, Alabaster, Ala. Lipid A from *Salmonella minnesota* R595 was purchased from List Biological Laboratories, Campbell, Calif. PVDF plates (Multiscreen-IP) were from Millipore, Bedford, Mass. Immullon 2 U and flat bottom and Immulon 4HBX 96 well ELISA plates were from Dynex, Chantily, Va. F96 Maxisorp 96 well ELISA plates were from Nalge Nunc International Corp., Naperville, Ill. Flat and U bottom tissue culture plates were from Costar-Corning, Corning, N.Y. FBS was from GIBCO BRL, Grand Island N.Y. and was heated at 56° C. for 1 h prior to use. Gelatin was from BioRad Laboratories, Richmond, Calif. Seal plate adhesive film was from PGC Scientific, Gaithersburg, Md. Affinity purified and adsorbed peroxidase-linked sheep anti-mouse IgM was from The Binding Site, San Diego, Calif. ABTS substrate was purchased from Kikegaard and Perry Laboratories, Gaithersburg, Md. Female Balb/c mice were purchased from Jackson Laboratories, Bar Harbor, Me.

Immunologic and Culture Reagents

Aluminum hydroxide gel, Alhydrogel, was purchased from Superfos Biosector, Vedbaek, Denmark. Mouse myeloma X63/Ag8.653 was purchased from American Type Culture Collection, Chantilly, Va. Polyethylene glycol 1500 was from Boehringer Mannheim, GmbH, Germany. Dulbecco's modified Eagle's medium with high glucose (DMEM), MEM sodium pyruvate (100 mM), MEM nonessential amino acids (NEAA) (100×), penicillin (10,000 units/ml)-streptomycin (10,000 µg/ml), 200 mM glutamine, 100×HAT (10 mM sodium hypoxanthine, 40 µM aminopterin, 1.6 mM thymidine) 100×HT (10 mM sodium hypoxanthine and 1.6 mM thymidine) supplements, Hank's Balanced Salts Solution, and fetal bovine serum were from GIBCO BRL, Grand Island, N.Y. Fetal bovine serum was heated at 56° C. for 1 hour prior to use. Peroxidase-linked goat anti-mouse IgM and peroxidase-linked goat anti-mouse IgG were purchased from The Binding Site, San Diego, Calif. ATBS substrate was purchased from Kirkegaard & Perry Laboratories, Gaithersburg, Md. Gelatin was from BioRad Laboratories, Richmond, Calif. Polystyrene Immulon II ELISA plates "U" and flat bottom were from Dynex, Chantilly, Va. PVDF Multiscreen-IP plates were from Millipore Corp., Bedford Mass. and adapted for ELISA. Seal plate adhesive film was from PGC Scientific, Gaithersburg, Md. Sterile Dulbecco's phosphate buffered saline lacking calcium and magnesium (PBS) was from BioWhittaker, Walkersville, Md. Nonsterile PBS was prepared from standard laboratory salts.

Manufacture of Liposomes

Liposomes containing SQE or SQA were prepared by a modification of the method of Alving et al. (1993). DMPC and DMPG were dissolved in chloroform at 180 mM and 20 mM, respectively. Lipid A was dissolved in chloroform at a concentration of 1 mg/ml. Glassware was depyrogenated overnight at 250° C. Chloroform solutions of lipids, including SQE or SQA, as appropriate, were placed in a pear shaped flask, and the chloroform was removed by rotary evaporation. The neck of the flask was covered with sterile Whatman 541 filter paper to maintain sterility. The dried lipid film was placed under high vacuum (50 mbar) for at least 1 hr. PBS was added to the dried lipid film to give a final phospholipid concentration of 100 mM. After closing with a ground glass stopper, the flask was shaken until all of the dried lipids were in suspension. Liposomes were stored at 4° C.

Liposomes Containing 43% Squalene for Immunization (Group 3)

Liposomes containing low amounts of SQE (43 mol %) were made with DMPC:DMPG:SQE in a molar ratio (9:1: 7.5). Lipid A was added to give a final dose of 25 µg in 0.2 ml of 100 mM phospholipid. Six ml of DMPC, 6 ml of DMPG, 1.5 ml of lipid A, and 0.438 ml of SQE were added to a 100 ml pear shaped flask. After drying as described above, PBS was added to give a final volume of 12 ml.

Liposomes Containing 71% Squalene for Immunization (Group 4)

Liposomes containing high amounts of SQE (71 mol %) were made with DMPC:DMPG:SQE in a molar ratio (9:1: 25). Lipid A was added to give a final dose of 25 µg in 0.2 ml of 100 mM liposomal phospholipid. Six ml of DMPC, 6 ml of DMPG, 1.5 ml of lipid A, and 1.46 ml of SQE were added to a 100 ml pear shaped flask. After drying as described above, PBS was added to give a final volume of 12 ml.

Liposomes Used for ELISA

Liposomes used for ELISA were made with DMPC:DMPG or DMPC:DMPG:SQE (or SQA, as appropriate), in molar ratios of 9:1 or 9:1:7.5. Twenty ml of DMPC, 20 ml of DMPG, and 1.44 ml of SQE or 1.6 ml of SQA (or no oil antigen) were added to a 100 ml pear shaped flask. After drying as above, PBS was added and the final volume of the liposomes was adjusted to 20 ml. The liposomes are designated L(SQE) for SQE-containing liposomes, L(SQA) for SQA-containing liposomes, or L for liposomes lacking an oil antigen. The final phospholipid concentration was 100 mM.

Preparation of Emulsions for Immunization

Emulsion with 40% SQE, 10% Arlacel A. and Lipid A (Group 5)

Components for this formulation were initially prepared in two separate 2 ml vaccine vials. One vial contained 1 ml of saline. For the second vial, 2.5 mg of lyophilized lipid A was dissolved in 8 ml of SQE; 2 ml of Arlacel A were then added; and 1 ml of the combination was added to the vial. The emulsion was prepared just prior to injection by emulsifying 0.75 ml of saline with 0.75 ml SQE-Arlacel A-lipid A using 2 three ml plastic syringes and a 3-way stopcock. The saline was drawn into one syringe and the SQE-Arlacel A-lipid A was drawn into another syringe. The saline was pushed into the SQE-Arlacel A-lipid A. The mixture was passed back and forth at a rate of approximately 2 passes/sec for 5 min. to form an emulsion. The emulsion was stable for several hours at room temperature.

Emulsion with 20% SQE, 5% Tween 80, 5% Span 85, and Lipid A (Group 6)

Components were vialed in two separate 2 ml vaccine vials prior to emulsification. One vial contained 1.5 ml of saline. The components for the second vial were made by dissolving 12 mg of lyophilized lipid A in 14.4 ml of SQE. Tween 80 (7.2 ml) and Span 85 (7.2 ml) were added to the lipid A in SQE. One ml of the mixture was vialed. The emulsion was prepared just prior to injection by emulsifying 1.05 ml saline with 0.45 ml SQE-Tween 80-Span 85-lipid A using 2 three ml plastic syringes and a 3-way stopcock as described above. The emulsion was unstable and separated into 2 layers in approximately 45 min.

Aluminum Hydroxide Gel Mixed with Emulsion Containing 19% Squalene, 1% Tween 80 and Lipid A (Group 7)

Aluminum hydroxide was diluted in saline to give 1.25 mg $Al^{+3}$/ml and 1.5 ml was placed in a 2 ml vaccine vial. The components for the second vial were made by dissolving 4 mg of lyophilized lipid A in 6 ml of SQE. Tween 80 (0.32 ml) was added and 1.5 ml of the mixture was added to a 2 ml vaccine vial. The formulation was prepared just prior to injection by emulsifying 1.2 ml of aluminum hydroxide in saline with 0.3 ml of SQE-Tween 80-lipid A, as described above. The final aluminum hydroxide concentration was 1 mg $Al^{+3}$/ml. The mixture was unstable and separated into 2 layers in less than 30 min.

Aluminum Hydroxide Gel Mixed with Emulsion Containing 40% Squalene, 10% Arlacel A, and Lipid A (Group 8)

Aluminum hydroxide was diluted in saline to give 2 mg $Al^{+3}$/ml, and 1.5 ml was added to a 2 ml vaccine vial. The components for the second vial were the same SQE-lipid A-Arlacel A mixture used in group 5. The formulation was prepared just prior to injection by mixing 0.75 ml of aluminum hydroxide in saline with 0.75 ml of SQE-Arlacel A-lipid A, as described above. The final aluminum hydroxide was 1 mg $Al^{+3}$/ml. The mixture was unstable and separated into 2 layers in less than 30 min.

TABLE IV

Summary of Immunization groups

| Group No. | Antigen Composition* |
|---|---|
| 1 | Squalene alone (0.5 ml) |
| 2 | Squalene (0.5 ml) mixed with 25 µg of lipid A |
| 3 | Liposomes containing both lipid A and 43 mol % squalene |
| 4 | Liposomes containing both lipid A and 71 mol % squalene |
| 5 | Emulsion containing 40% squalene, 10% Arlacel A, and lipid A |
| 6 | Emulsion containing 20% squalene, 5% Tween 80, 5% Span 85, and lipid A |
| 7 | Aluminum hydroxide gel mixed with emulsion containing 19% squalene, 1% Tween 80 and lipid A |
| 8 | Aluminum hydroxide gel mixed with emulsion containing 40% squalene, 10% Arlacel A and lipid A |

*All injections were administered i.p. in a 0.2 ml dose, except where indicated. Lipid A, when used, was administered at 25 µg of lipid A/dose.

Example 1

Immunizations

BALB/c mice, purchased from Jackson Labs. (Bar Harbor, Me.), were immunized i.p. and bled every 2 weeks under a protocol approved by the institutional Laboratory Animal Care and Use Committee. They were fed standard mouse chow and water ad libitum. Groups of five mice received one of the following immunogens: Group 1-0.5 ml SQE; Group 2-0.5 ml of SQE containing 25 µg lipid A; Group 3-0.2 ml of 43% SQE liposomes; Group 4-0.2 ml of 71% SQE liposomes; Group 5-0.2 ml of emulsion containing 50% saline (0.9% sodium chloride), 40% SQE, 10% Arlacel A containing 25 µg lipid A/dose; Group 6-0.2 ml of an emulsion containing 70% saline, 20% SQE, 5% Tween 80, 5% Span 85 (v/v) containing 25 µg lipid A/dose; Group 7-0.2 ml aluminum hydroxide in saline, 19% SQE, 1% Tween 80, containing 25 µg lipid A/dose; Group 8-0.2 ml of aluminum hydroxide in saline, 40% SQE, 10% Arlacel A containing 25 µg lipid A/dose (Table IV). Animals were boosted every 2 weeks. Three additional mice were immunized by the intravenous route with 0.2 ml of the high SQE liposomes (group 4). Three days later, the animals were euthanized and the spleens removed for production of monoclonal antibodies.

Example 2

Production of Monoclonal Antibodies

Three days after the primary or boosting immunization, mice were euthanized and spleens obtained. Single cell suspensions of spleen cells were prepared. Spleen cells and mouse myeloma X63/Ag8.653 cells were fused in a 1:1 ratio using polyethylene glycol 1500 (Köhler and Milstein, 1975; Galfré and Milstein, 1981). After fusion, the cells were centrifuged and then suspended in DMEM containing 20% fetal bovine serum, 1 mM sodium pyruvate, 1×NEAA, 4mM glutamine, 50 units/ml penicillin, 50 µg/ml streptomycin, 1×HT (30 ml/spleen). Cells (0.1 ml/well) were plated in 96 well plates. The next day 0.1 ml of DMEM media containing 1×HAT instead of HT was added to all of the wells. On days 2, 3, 5, 8, and 11, 0.1 ml of media was removed from each well and 0.1 ml of DMEM containing HAT was added. After 8 days culture supernatants were screened for antibodies reacting with SQE and not SQA by ELISA on PVDF plates as described below. Cells from culture supernatants that were positive were expanded and then cloned twice by limiting dilution.

Example 3

ELISA for Testing Serum for Antibodies to SQE Using Polystyrene (PS) Plates

Solid-phase ELISAs were performed as described previously with minor modifications (Alving et al., 1996). For the initial serum screen assays, 10 µg of SQE or SQA in 50 µl of ethanol was placed in PS "U" bottom plates. The plates were placed overnight in a biological safety cabinet to allow the ethanol to evaporate. The plates were blocked with 0.25 ml of PBS-0.3% gelatin for 2 h. After removal of the blocking buffer, 50 µl/well of serum diluted in PBS-0.3% gelatin was added in triplicate. The plates were incubated at 4° C. overnight. The plates were then washed 3 times with PBS using a plate washer (Skatron Inc., Sterling, Va.). Peroxidase-labeled goat IgM (µ chain specific) were diluted 1000-fold in PBS-0.3% gelatin and 50 µl/well was added to the plates. Following incubation at room temperature for 1 h, the plates were washed 3 times with PBS. ABTS substrate (50 µl/well) was added and the plates were incubated for 1 h at room temperature in the dark. The absorbance at 405 nm was quantified using a UVmax Kinetic Microplate Reader (Molecular Devices, Palo Alto, Calif.). Assays were conducted in triplicate. Assay background was determined by incubation with wells lacking antigen. Background was subtracted from experimental values. Endpoint antibody titers were selected as the dilution at which the absorbance was twice background.

Example 4

ELISA for Testing Culture Supernatants for Antibodies to SQE Using PS Plates

For assay of culture supernatants of monoclonal antibodies, PS flat bottom plates were used. The assay was similar to that described above for the "U" bottom plates with the following changes. 1) The assay volumes of coating antigen, primary and secondary antibodies and substrate was increased from 50 µl to 100 µl; 2) SQE and SQA were dissolved in isopropanol; 3) Incubation of with culture supernatants was for 1 h at room temperature instead of overnight at 4° C. These changes gave less background and somewhat greater reproducibility among triplicate determinations when compared to ELISA on PS "U" bottom plates. However, better results were obtained using PVDF membranes.

Example 5

ELISA for Antibodies to SQE Using PVDF Plates

The assay for antibodies to SQE was modified from the method described for detecting antibodies to cholesterol by Dijkstra et al. (1996). 0.1 ml of SQE or SQA, as appropriate, dissolved in isopropanol were placed in each well and the plate was placed overnight in a biological safety cabinet to allow the isopropanol to evaporate. The wells were blocked with PBS-4% FBS, pH 7.4, (0.3 ml/well) and incubated at room temperature for at least 1 hr. After removal of the blocking buffer, 0.1 ml of culture supernatant (either undiluted or diluted in PBS –4% FBS) was added to each well. The plate was covered with seal plate adhesive film and placed on a orbital shaker set at 1,500 rpm for 1 hr. The plates were then washed 4 times with PBS-4% FBS. Sufficient PBS-4% FBS was added to each well until the air bubble floated off the PVDF membrane. Peroxidase-linked goat anti-mouse IgG or IgM was diluted 1 to 1000 in PBS-4% FBS and 0.1 ml was added to each well. The plates were covered with seal plate adhesive film and placed on the shaker as described above. The plates were washed 4 times with PBS as described above. ABTS substrate (0.15 ml/well) was added and the plates were covered with seal plate adhesive film. They were placed on the shaker, covered with aluminum foil, and shaken at 1,500 rpm. After 1 hr, 0.05 ml was transferred from each well and placed in a corresponding well of 96 well "U" bottom plate. The absorbance was read at 405 nm using an ELISA plate reader.

Example 6

ELISA Using L(SQE), L(SQA) and L as Capture Antigens

ELISAs using liposomes as capture antigens were performed using "U" bottom PS plates. L(SQE), L(SQA), or L, as appropriate, were diluted to 660 nmol/ml in PBS (equivalent to 10 µg SQE). Fifty µl (33 nmol) were placed in each well. The plate was placed in a biological safety cabinet overnight. The plates containing the dried film of liposomes were processed by ELISA as described in section 2.7. For serum assays, the plates containing diluted serum were incubated overnight at 4° C. For assays using diluted supernatants from the monoclonal antibodies, the plates were incubated 1 h at room temperature.

Example 7

Induction and Reactivity of Polyclonal Antisera with SQE by ELISA

Figure 2:
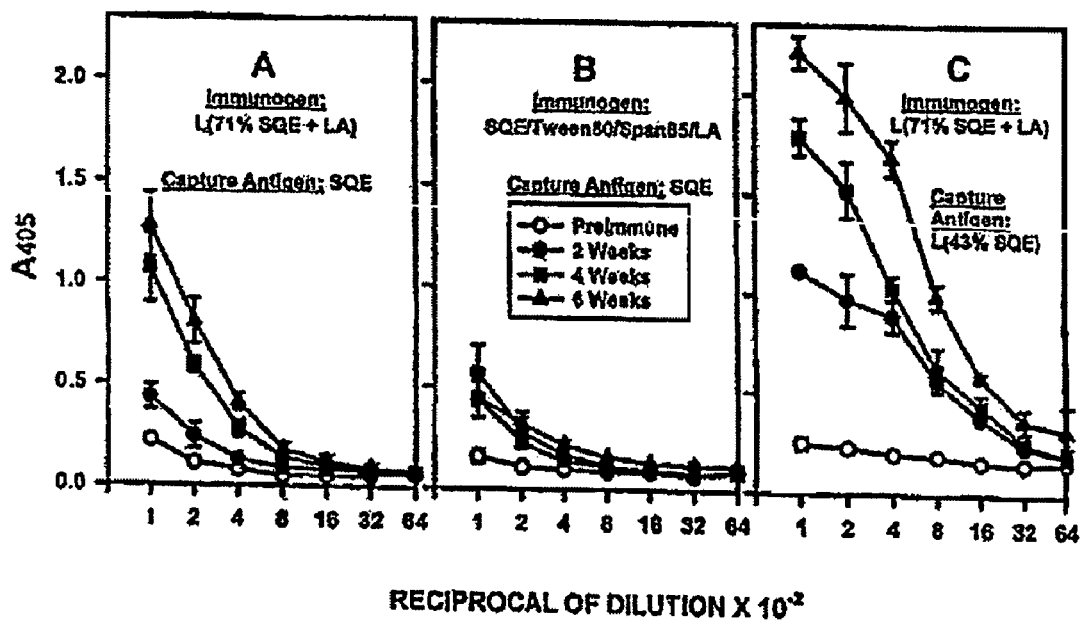

Sera from immunized mice were tested by ELISA for the presence of anti-SQE antibodies using SQE as the capture antigen. Among the eight immunization strategies employed (see Materials and Methods, and summary in Table IV), only two groups exhibited increased IgM binding activity after injection of the antigen when compared to the preimmunization serum (group 4, FIG. 2A; group 6, FIG. 2B). None of the groups developed IgG binding activity after immunization (data not shown). Mice injected with liposomes containing lipid A and 71% SQE [L(71% SQE+LA)] (group 4, see Table I) showed progressively increased IgM titers with time when compared to the pre-immunization bleeding (FIG. 2A). The animals were immunized every 2 weeks, and even at 2 weeks after a single injection, an increased IgM titer was evident. To a much lesser extent one of the SQE emulsion groups (group 6, see Table I) also developed increased titers when compared to the pre-immune sera, but even after multiple injections there was no progressive increase in the antibody titer (FIG. 2B). Because of this, in all further experiments sera from animals immunized with L(71% SQE+LA) was used.

Figure 3:
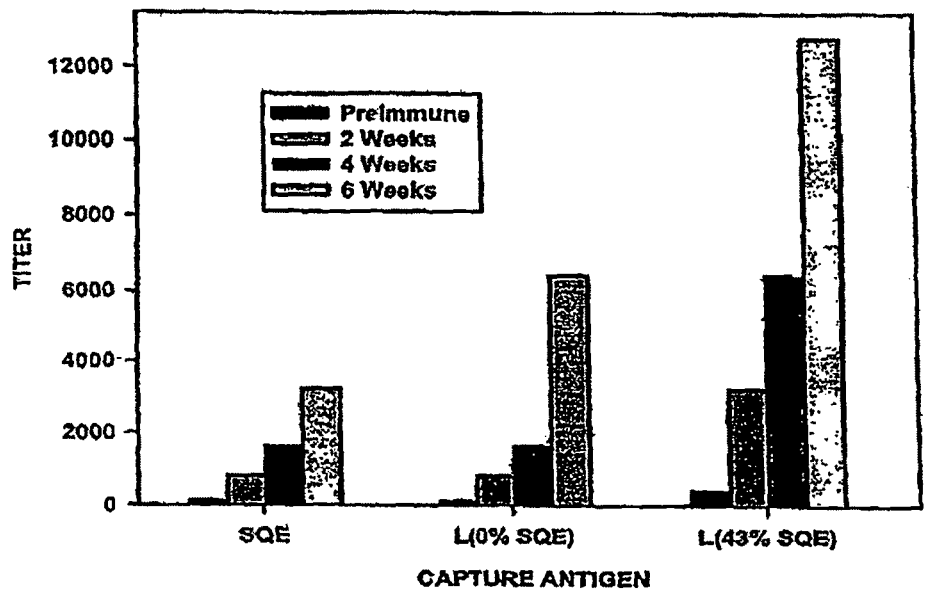

Using an alternative capture antigen in the ELISA, namely liposomes containing SQE an even higher resolution of positive results was observed when compared to the results obtained with SQE alone (FIG. 3A) as a capture antigen. However, as shown in FIG. 3, after immunization with liposomes containing SQE and lipid A, the antisera reacted not only with SQE alone but also with liposomes lacking SQE, albeit to a much lesser extent than with liposomes containing SQE. This latter observation is consistent with previous reports that antibodies to phospholipids are also induced when liposomal lipid A, or even lipid A alone, is used as an adjuvant (Schuster et al., 1979; Banerji et al., 1981; Alving, 1986).

The above data suggested that antibodies that could react with SQE were induced in mice by immunization with certain formulations that contained SQE. However, when another oil molecule, SQA, the fully hydrogenated form of SQE, was substituted for SQE as a capture antigen in the ELISA, the polyclonal antiserum to SQE reacted equally well with either SQE or SQA (data not shown). This apparent lack of monospecific binding to SQE could have been due either to extensive cross-reactivity of anti-SQE antibodies with SQA, or to a mixed population of antibodies, some of which cross-reacted with SQA and some of which did not. The possibility of nonspecific binding of IgM antibodies also existed. Because of this, we decided to try to produce monoclonal antibodies that could differentiate between SQE and SQA as antigens. In the course of this work, as shown below, we also refined the ELISA assay to minimize nonspecific effects and increase resolution.

Example 8

Development of Monoclonal Antibodies to SQE

Figure 4:
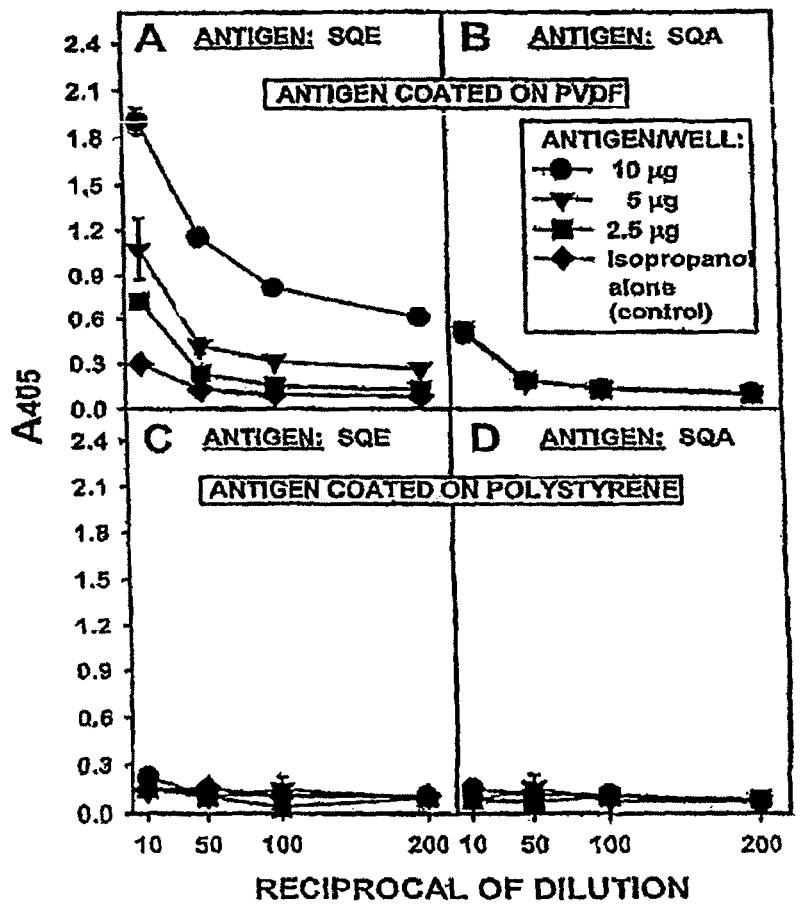

To minimize experimental variation and nonspecific effects observed after coating of hydrophobic antigens on polystyrene microtiter wells, we examined the possible benefits of coating the capture antigens on hydrophobic membranes consisting of polyvinylidene fluoride (PVDF), as described by Aniagolu et al. (1995). As shown in FIGS. 4A and B, when culture supernatants were assayed with PVDF membranes, an IgM anti-SQE mAb was identified that exhibited strong dose-dependent binding to SQE, but displayed little or no cross-reactivity to SQA. When the antigens were coated on flat bottom PS microtiter wells instead of PVDF membranes, the same anti-SQE mAb showed a complete lack of reactivity with either SQE or SQA (FIGS. 4C and D).

Figure 5:
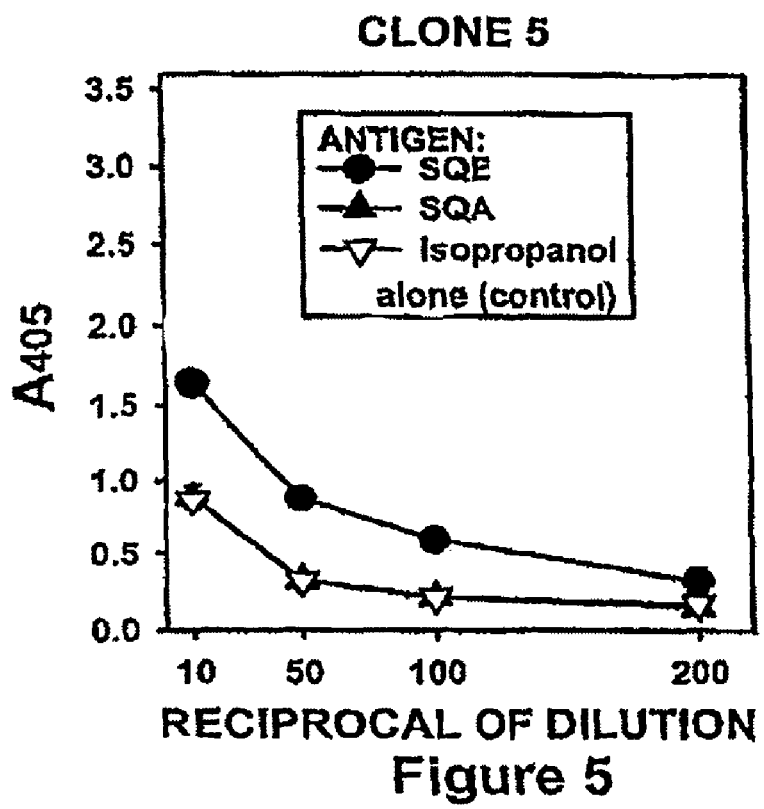
FIG. 5 shows the specific binding of mAb clone 5 to SQE, but not SQA. The assay was conducted with PVDF plates as described in the legend to FIG. 4.
Figure 6:
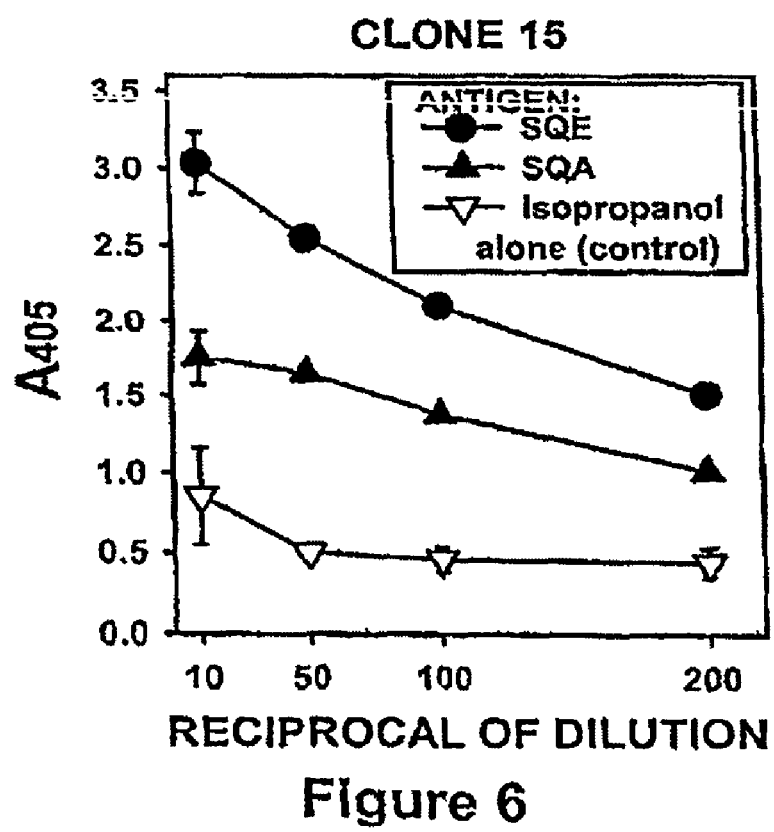
FIG. 6 shows the binding of mAb clone 15 to SQE and cross-reactivity with SQA. The assay was conducted with PVDF plates as described in the legend to FIG. 4.

Additional clones of anti-SQE mAbs were also produced which, when tested with the PVDF membrane assay, either showed striking specificity for SQE (clone 5, FIG. 5), or reactivity with both SQE and SQA (clone 15, FIG. 6). These data demonstrate that mAbs can be identified that differentiate free SQE from free SQA by ELISA, particularly when the antigens are coated on PVDF membranes.

Example 9

Evaluation of the Specificity of mAbs for Reactivity with a Capture Antigen Consisting of Liposomes Containing SQE or SQA The original immunizing antigen consisted of liposomes containing SQE+LA. FIG. 7 illustrates the results of ELISAs in which PS plates were coated with liposomes containing or lacking SQE or SQA. An irrelevant IgM mAb (anti-asialoG$_{M2}$) is shown as a negative control (FIG. 7E). When analyzed for reactivity with liposomes containing SQE [L(SQE)], liposomes containing SQA [L(SQA)], or liposomes lacking both SQE and SQA [L], four different patterns of specificity for L(SQE), L(SQA), and L alone were observed, as derived from FIG. 7 and summarized in Table II. It is noteworthy that we have never obtained a mAb that bound more strongly to SQA than to SQE. This is in keeping with the primary specificity of the antibodies for liposomal SQE.

Evaluation of the Specificity of Polyclonal Antiserum for SQE and SQA on PVDF Membranes.

The above studies demonstrate that immunization with SQE induces a mixed population of anti-SQE antibodies that includes some that do not cross-react and some that do cross-react with SQA. In view of this, polyclonal anti-SQE antiserum would be expected to exhibit both SQE reactivity and SQA cross-reactivity on PVDF membranes. As shown in FIG. 8, reactivity with both antigens was observed with polyclonal anti-SQE antiserum.

To demonstrate that specific antibodies to SQE actually do exist, we created mAbs that were selected for the ability to bind to SQE but had a relative inability to bind to SQA, as determined by ELISA with hydrophobic PVDF membranes. Monoclonal antibodies were successfully created that specifically bound to SQE but to a lesser extent, or not at all, to SQA. However, numerous anti-SQE mAbs were also created that cross-reacted strongly with SQA. It is concluded that specific differentiation of SQE from SQA demonstrates that the unsaturated bonds of SQE can play a major role in the specificity of the antibodies, and such antibodies therefore have a distinctive conformational specificity. However, the extensive cross-reactivity of numerous clones of anti-SQE antibodies with SQA also demonstrates that the unsaturated bonds are not the sole determinant of specificity.

Example 10

We have demonstrated in this study that polyclonal and monoclonal antibodies that bind to SQE can be developed after immunization of mice with liposomes containing 71% SQE and lipid A. Other methods of immunization, including immunizing with liposomes containing 43% SQE or with a variety of SQE-containing emulsions, were either completely ineffective, or considerably less effective, as immunogens. The strategy of utilizing liposomes containing 71% SQE and lipid A as an immunogen was modeled after similar success in the induction of antibodies to cholesterol by immunizing with liposomes containing 71% cholesterol and lipid A (Swartz et al., 1988; Alving and Swartz, 1991; Dijkstra et al., 1996). Although we have previously found that simple injection of silicone oil into mice can also cause the induction of antibodies to cholesterol (Alving et al., 1996), injection of non-emulsified SQE oil mixed with lipid A did not result in the induction of antibodies to SQE (group 2, Table IV). Among four emulsions containing SQE and lipid A as components, only one (group 6, Table I) induced any immune response to SQE, and this was quite weak even after multiple injections (FIG. 2B). From these data we conclude that SQE is a very poor antigen when used either as an oil or an emulsion, even when lipid A, a potent adjuvant for inducing antibodies to lipids, is included in the immunizing formulation.

The results in the present study are consistent with the concept of induction of anti-liposome mAb antibodies having specificities that include both liposomal phospholipid as well as SQE in the antigen binding site of the antibody (FIGS. 7B and C; Table V). However, as with the anti-cholesterol mAbs, anti-SQE clones were also obtained that did not react with liposomal phospholipid (FIGS. 7A and D; Table V).

TABLE V

Monoclonal Antibody Specificities Obtained After Injection of Liposomes Containing Lipid A and SQE

| | Binding Specificity* | | |
|---|---|---|---|
| Clone No. | SQE | SQA | Liposomal phospholipid |
| 15 | + | − | − |
| 4 | + | + | + |
| 18 | + | − | + |
| 14 | + | + | − |

*Based on data from FIG. 7.

Example 11

The extreme hydrophobicity of SQE raises an important theoretical problem in demonstrating specificity of antibodies because polyclonal antiserum raised by immunization with SQE shows considerable reactivity with SQA (FIG. 8). Based on serum data alone, it was therefore initially impossible to determine whether the apparent antibody activity in the antiserum is specific to SQE, or if the immunoglobulins are simply nonspecifically binding hydrophobically both to SQE and SQA. The initial experiments using PS microtiter plates did indeed demonstrate nonspecific hydrophobic binding of IgM molecules to both SQE and SQA, and other alkanes (data not shown). However, this problem was solved by coating the antigens on hydrophobic PVDF membranes, as described by Aniagolu et al. (1995). Although commercially-available PVDF membranes also present the problem that they are physically located in PS microtiter wells, they apparently do have the salutary effect of blocking most or all of the nonspecific hydrophobic binding sites of the alkane molecules.

Example 12

Culture supernatants containing monoclonal antibodies (mAbs) to SQE were grown in Dubbelco's modified Eagle's medium as described (Matyas 2000) Mice were injected with liposomes containing 71 mol percent SQE and lipid A, intraperitoneally as described (Matyas 2000). Anti-SQE positive serum was obtained by terminal bleeding three days after immunization. The serum was aliquoted and frozen at $-20°$ C. The experiments described in this paper used several different lots of monoclonal supernatants and anti-SQE serum.

Example 13

ELISA Assay on PVDF Plates

The ELISA assay in plates containing PVDF membranes were conducted as described (Matyas 2000). Briefly, SQE was diluted in isopropanol and placed in the wells of the plate. After drying overnight, the wells were blocked with PBS-4% FBS, pH 7.4, for 2 h. Serum and supernatants containing monoclonal antibodies to SQE were diluted in PBS-4% FBS and 0.1 ml was placed in a well. Following incubation for 1 h, the plate was washed four times with PBS-4% FBS by hand using a 25 ml pipet. 0.1 ml of peroxidase-linked sheep anti-mouse IgM diluted 1:1000 in PBS-4% FBS was added to each well. The plate was incubated for 1 h and then washed 4 times with PBS by hand. 0.15 ml of ABTS substrate was added to each well and the plates were incubated for 1 h. 0.1 ml/well was transferred to an Immulon 2 U bottom plate and the absorbance was read at 405 nm with a Uvmax Kinetic Microplate Reader (Molecular Devices, Palo Alto, Calif.). In some experiments PVDF plates were washed 4 times with 0.5 ml of PBS/well with an ELISA plate washer (Skatron, Sterling, Va.). The vacuum probes of the washer were positioned just above the PVDF membrane.

Example 14

ELISA Assay on Polystyrene Plates

The ELISA assay for polystyrene plates was performed as described (Matyas). The assay for polystryrene tissue culture U bottom plates is described in detail. SQE was diluted in isopropanol (1 μmol/ml; 24 μl SQE/50 ml) and 0.1 ml was placed in each well. Control wells were isopropanol alone. The plates were placed in a biological safety cabinet and incubated overnight to allow the isopropanol to evaporate. PBS-4% FBS, pH 7.4 was added to each well (0.3 ml/well) to block unbound binding sites. After incubation at room temperature for 2 h, the plates were dumped and tapped on paper towel to removed the blocked. Culture supernatants containing monoclonal antibodies to SQE or mouse serum was diluted in PBS-2% BSA and added to the plates in triplicate. Following incubation for 1 h at room temperature, the plates were washed 4 times with 0.5 ml of PBS/well using a Skatron plate washer. Peroxidase-linked sheep anti-mouse IgM was diluted 1:1000 in PBS-4% FBS and 0.1 ml was added to each well of the plate. The plates were incubated 1 h at room temperature and washed 4 times with PBS. ABTS substrate (0.1 ml/well) and the plates were incubated at room temperature for 1 h. Absorbance was read at 405 nm.

Example 15

Effect of Polystyrene Plate Type on the Measurement of Antibodies to SQE

Seven different plates coated with SQE as an antigen were compared for their ability to detect monoclonal antibodies and serum antibodies to SQE. Hand washed Millipore IP plates had low background (isopropanol-treated wells) and high anti-SQE absorbances for the mAbs, but low absorbances to SQE-coated wells were obtained for anti-SQE serum (FIG. 9A). When the Millipore IP plates were washed with an ELISA plate washer, the background absorbances for the anti-SQE serum significantly increased (FIG. 9B). Immulon 2 U and flat bottom plates had very high background absorbances for the mAbs and the anti-SQE serum (FIGS. 9G, H). Immulon 4HBX had elevated absorbances for SQE-coated wells that were not incubated with primary antibody (FIG. 9E). Maxisorp F96 plates had elevated background absorbances with anti-SQE serum. Costar U and flat-bottom tissue culture plates had low background absorbances and high absorbances for SQE-coated wells with both the mAbs and anti-SQE serum (FIGS. 9C, D). There were no real differences in ELISA values observed between the U bottom and flat bottom Costar tissue culture plates. The Costar U bottom plate was chosen for the assay of antibodies to SQE.

Example 16

Standardization of the ELISA Assay for Mouse SQE Antibodies on Costar U Bottom Tissue Culture Plates The plates were tested with various blocker/diluents in order to minimize background and maximize antibody binding to SQE. PBS-0.5% casein effectively abolished the binding of the mAbs to SQE (FIGS. 10A, B) and elevated the background with the anti-SQE serum (FIG. 11D). PBS-0.3% gelatin and PBS-0.6% gelatin inhibited the binding of the mAbs to SQE-coated wells (FIGS. 10A, B). In addition, when gelatin was used as a blocker/diluent, the results from experiment to experiment were highly variable. When PBS-1% BSA was used as a blocker/diluent, absorbances increased over 2-fold for the mAbs on SQE-coated wells ompared to similar wells using PBS-4% FBS as a blocker/diluent (FIGS. 10A, B). Background absorbances with PBS-1% BSA were similarly increased approximately 2-fold for both the mAbs, normal mouse and anti-SQE serum (FIG. 10). Various concentration of BSA were tested to determine if the background could be reduced. mABs and anti-SQE serum had high absorbances for SQE-coated wells using PBS-1% and 2% BSA as blockers/dilutents (FIG. 11). BSA concentrations greaterthan 2% caused significant reductions in the absorbances of SQE #18 (FIG. 11B) and anti-SQE serum (FIG. 11D). Background absorbances for isopropanol-treated wells were greatly reduced by increasing the BSA from 1% to 2%, but did were not dramatically reduce further with increasing concentrations of BSA (FIG. 11). PBS-2% BSA was chosen as the blocker/diluent.

The optimal incubation temperature was investigated. The binding of clone SQE #16 was independent of the incubation temperature (FIG. 12A). Maximal binding of anti-SQE serum to SQE-coated wells occurred at temperatures above 4° C. (FIG. 12B). Background binding of anti-SQE serum to isopropanol-treated wells was relatively independent of temperature. There was a slight increase in binding to isopropanol-treated wells at 22° C. Since binding was basically independent of temperature, room temperature was chosen for the standard assay.

A comparison of the time required for primary antibody binding to SQE-coated wells indicated that overnight incubation did not increase the binding of clone SQE #16 to SQE-coated wells (FIG. 13A). There was increased binding of anti-SQE serum to SQE-coated wells with overnight incubation, but this was mostly offset by and an increase in background binding to isopropanol-treated wells (FIG. 13B). One hr was chosen as the incubation time for primary antibody. Similarly, there was no difference between incubating with secondary antibody for 1 or 2 hr for both clone SQE #16 and anti-SQE serum (FIG. 14). Consequently, 1 hr was chosen as the incubation for secondary antibody.

The binding of mAbs SQE #14 and SQE #16 was dependent upon the amount of SQE added to the wells (FIGS. 15A, B). Maximal binding was observed from 10 to 25 nmol of SQE. Maximal absorbances for anti-SQE serum were obtained from 7.5 to 100 nmol of SQE. SQE amounts above or below those amounts had decreased absorbances. Control mouse IgM monoclonal antibody did not bind to SQE at any amount coated on the plate (FIG. 15A). Ten nmol of SQE was chosen as the preferred amount for the standard assay.

Example 17

Conditions for the Standard Assay for Measuring Mouse Antibodies to SQE

Based on the results described above, the following conditions were adopted as the standard assay conditions:

1. Costar 96 well "U" bottom sterile tissue culture plates were chosen.

2. A SQE concentration of 10 nmol SQE/well in 0.1 ml of isopropanol was chosen. The isopropanol was allowed to evaporate over night in a biological safety cabinet with the air turned-on.

3. The plates were blocked with 0.3 ml/well of PBS –2% BSA, pH 7.4 for 2 hr at room temperature.

4. Mouse serum or monoclonal antibodies are diluted in PBS –2% BSA.

5. The plates are dumped and tapped on paper towels. 0.1 ml/well of diluted serum or monoclonal antibody was added to the plate. The plates were covered and incubated at room temperature for 1 hr.

6. The plates were washed 4 times with PBS, pH 7.4 with 0.5 ml/well.

7. Peroxidase-linked sheep anti-mouse IgM was diluted 1:1000 in PBS –2% BSA and 0.1 ml was added to each well. The plates are covered and incubated at room temperature for 1 hr.

8. The plates were washed 4 times with PBS, pH 7.4 at 0.5 ml/well.

9. 0.1 ml of ABTS substrate was added to each well. The plates were covered with foil and incubated at room temperature for 1 hr.

10. The absorbance was read at 405 nm.

Example 18

Reproducibility of the Assay

Several different lots of Costar U bottom tissue culture plates were tested under the standard assay conditions. There was no difference among the absorbances obtained with the mAbs on the different lots of plates (FIGS. 16A, B). Slight differences in absorbances were observed with different lots of plates with anti-SQE serum on SQE-coated wells (FIG. 17C). Background absorbances were the same on the different lots of plates for both the monoclonal antibodies and the anti-SQE serum. The assay was highly reproducible from day to day both with the monoclonal antibodies (FIG. 17A) and with anti-SQE serum (FIG. 17B).

Example 19

Detection of Antibodies to Squalene in Human Sera

Squalene and squalane oils were purchased from Sigma-Aldrich Chemical Company, St. Louis, Mo. Isopropanol and casein were purchased from J. T. Baker, Phillipsburg, N.J. Gelatin was from BioRad Laboratories, Richmond, Calif. Flat and U bottom tissue culture plates were from Costar-Corning, Corning, N.Y. Affinity purified and adsorbed peroxidase-linked sheep anti-human IgG and IgM was from The Binding Site, San Diego, Calif. ABTS substrate was purchased from Kirkegaard and Perry Laboratories, Gaithersburg, Md. Human serum samples were obtained under IRB approved protocol from Phillip Pittman at the United States Army Medical Research Institute of Infectious Disease, Frederick, Md.

Elisa Assay

Squalene was diluted in isopropanol to 0.2 µmol/ml (9.6 µl squalene/100 ml) and 0.1 ml was placed in each well. Control wells contained isopropanol alone. The plates were placed in a biological safety cabinet and incubated overnight to allow the isopropanol to evaporate. PBS-0.5% casein, pH 7.4, was added to each well (0.3 ml/well). After incubation at room temperature for 2 h, the plates were dumped and tapped on a paper towel to removed the blocking buffer. Serum samples were diluted in PBS-0.5% casein and added to the plates in triplicate. Following overnight incubation at room temperature, the plates were washed 4 times with 0.5 ml of PBS/well using a MAP-C ELISA workstation (Titertek, Huntsville, Ala.). Peroxidase-linked sheep anti-human IgG and IgM was diluted 1:1000 in PBS-0.5% casein and 0.1 ml was added to each well of the plate. The plates were incubated 1 h at room temperature and washed 4 times with PBS. ABTS substrate (0.1 ml/well) and the plates were incubated at room temperature for 1 h. Absorbance was read at 405 nm.

Serum Anti-Squalene Grading Criteria

POSITIVE—The absorbance for the squalene-coated wells was at least 2.5 times that of isopropanol-treated wells and 10 times the absorbance for squalene-coated wells that were not incubated with primary antibody.

INCONCLUSIVE—(high background) The absorbance for isopropanol-treated wells was at least 5 times the absorbance of isopropanol-treated wells that were not incubated with primary antibody and the absorbance for the squalene-coated wells was at least 10 times the absorbance for squalene-coated wells that were not incubated with primary antibody.

NEGATIVE—The absorbances failed to meet the above criteria.

SUMMARY

A. 4.1% of the serum samples (8 of 197) were positive for IgG antibodies to squalene.

B. 95.9% of the serum samples (189 of 197) were negative for IgG antibodies to squalene.

C. 10.2% of the serum samples (20 of 197) were positive for IgM antibodies to squalene.

D. 14.2% of the serum samples (28 of 197) were inconclusive for IgM antibodies to squalene. These sera had high background binding to isopropanol-treated wells.

E. 75.6% of the serum samples (149 of 197) were negative for IgM antibodies to squalene.

F. Most of the positive anti-squalene samples had endpoint titers of 100-200.

The results for these experiments are shown graphically in FIGS. 18-22.

Additional Materials and Methods for Detection of Human Antibodies to Squalene Associated with the Improvement Additional Materials Squalene oil and bovine serum albumin (essentially fatty acid free; cat. # A-7030) were purchased from Sigma-Aldrich Chemical Company, St. Louis, Mo. Isopropanol (BAKER ANALYZED® A.C.S. Reagent; cat. # 9084-03) and casein were purchased from J. T. Baker, Phillipsburg, N.J. Costar round bottom 96-well sterile tissue culture plates (cat.# 3799) were purchased from Corning Inc., Corning, N.Y. FBS was from GIBCO BRL Grand Island N.Y. and was heated at 56° C. for 1 h prior to use. 10× Dulbecco's PBS without $Ca^{++}$ and $Mg^{++}$ was also purchased from GIBCO BRL. Human myelomas were purchased from the American Type Culture Collection, Chantilly, Va. and were grown as described in the supplier's instructions with culture medium and additives from GIBCO BRL. The human antibody secreting myelomas were IM-9 (IgG of unknown specificity obtained from a myeloma) (Fahey et al., 1971), SA13 (IgG to tetanus toxoid) (Larrick et al., 1986), 16M3F10 (IgG to diphtheria toxoid) (Gigliotti et al., 1984), C5 (IgM to lipid A of Gram negative bacteria (Teng et al., 1985), L612 (IgM to gangliosides GM3 and GM4) (rie., 1995) and RPMI 1788 (IgM to tumor necrosis factor beta) (Aggarwal et al., 1984). Mouse myeloma SQE #16, which secretes a monoclonal antibody to SQE, was grown as described (Matyas et. al., 2000; Matyas et al., 2002). Human IgG and IgM and mouse IgM quantitation kits were purchased from Bethyl Laboratories, Montgomery, Tex. and were used on the culture supernatants containing mAbs as per the enclosed instructions. Affinity purified and adsorbed peroxidase-linked sheep anti-human IgG (?-chain specific), anti-human IgM, anti-mouse IgG (?-chain specific) and anti-mouse IgM were purchased from The Binding Site, San Diego, Calif. ABTS substrate was purchased from Kirkegaard and Perry Laboratories, Gaithersburg, Md. Female BALB/c, B10.Br and C57BL/6 mice were purchased from Jackson Laboratories, Bar Harbor, Me. Retired breeder mice were purchased at 10 months of age. Animal research was conducted in compliance with the Animal Welfare Act and other Federal statutes and regulations relating to animals and experiments involving animals and adheres to principles stated in the Guide for the Care and Use of Laboratory Animals, NRC Publication, 1996 edition.

Volunteer Population and Serum Preparation

Volunteers were recruited according to U.S. Army regulations under human use protocols approved by the Walter Reed Army Institute of Research and the United States Army Medical Research Institute of Infectious Diseases Human Use Review Committees and the U.S. Army Human Subjects Research Review Board. Written informed consent was obtained from all volunteers prior to enrollment into the study. U.S. Army human use guidelines were strictly adhered to throughout the course of this study.

Three cohorts were studied. The first cohort consisted of retired employees of the United States Army Medical Research Institute of Infectious Diseases (referred to as USAMRIID alumni). Most had received numerous doses of AVA and other vaccines through a USAMRIID special immunization program (Pittman et al., 2002). All individuals (N=40) were greater than 58 years old (mean age 68; range 58-82; 87.5% male) and most had received multiple doses of AVA (mean of 24 doses, range 0-47 doses). Three individuals were not vaccinated with the anthrax vaccine and the vaccine status of three others was unknown.

The second cohort was of similar age (mean age 67; range 54-97; 61.8% male) from the normal population of Frederick, Md. 372 individuals were enrolled, and none had been vaccinated with AVA. Blood was collected by standard clinical laboratory methods and the serum was removed and frozen at −80° C.

For the third cohort, outdated fresh frozen plasma was purchased from Camp Memorial Blood Center, United States Army Medical Department Activities, Fort Knox, Ky. No donor information was provided to the investigators of this study. However, the overall donor population of the Fort Knox Blood Center is comprised of 85% basic trainees, ranging in age from 17-21. Their immunization status with respect to AVA administration is unknown. Pooled normal human serum, which on analysis was found to be slightly positive for IgG and IgM antibodies to SQE, was purchased from United States Biological, Swampscott, Mass. All of the above serum and plasma were thawed, aliquoted and refrozen at −80° C. prior to assay.

ELISA Assay for Antibodies to SQE in Human Serum and Plasma

SQE was diluted in ISP (0.2 μmol/ml; 9.6 μl SQE/100 ml) and 0.1 ml (20 nmol) was placed in each well of a Costar 96-well sterile round bottom tissue culture plate. Control wells contained ISP alone. The plates were placed in a biological safety cabinet and incubated overnight to allow the ISP to evaporate. PBS-0.5% boiled casein, pH 7.4 (0.3 ml) was added to each well. After incubation at room temperature for 2 h, the buffer was removed and the plates were tapped on paper towels to remove the residual blocker. Human serum was diluted serially in PBS-0.5% casein starting at a 1:25 dilution. Diluted serum (0.1 ml/well) was added to the plate in triplicate. The plates were covered with plastic wrap and incubated overnight at room temperature. The plates were then washed 4 times with 0.5 ml/well of PBS, pH 7.4. Peroxidase-linked sheep anti-human IgG (?-chain specific) and IgM (μ-chain specific) was diluted 1:1000 in PBS-0.5% casein and 0.1 ml/well was added to the plate. Following a 1 h incubation at room temperature, the plates were washed as described above. ABTS substrate (0.1 ml/well) was added and the plates were incubated at room temperature for 1 h. Absorbance was read at 405 nm. Each plate contained culture supernatant from the C5 cell line, pooled normal human serum and blocking buffer as controls. It should be noted that polystyrene pipets, tubes, or other objects containing polystyrene, should not be used in this assay. The use of polystyrene caused high background (ISP) absorbances and greatly increased the variability of the results. Highly purified ISP also was required in order to ensure low background absorbances.

ELISA Assay for Antibodies to SQE in Mouse Serum

The assay was performed as described by Matyas et al., (2002) with 10 nmol SQE per well. Briefly, the mouse serum assay was similar to the human assay except for the following: 1) PBS-3% BSA was used as a blocker and diluent. 2) Culture supernatant from hybridoma SQE#16 containing a monoclonal antibody to SQE was included as a positive control on each plate. 3) Diluted mouse serum was incubated for 1 h on the plates. 4) Peroxidase-linked sheep anti-mouse IgG (?-specific) and IgM (p-chain specific) (The Binding Site) were used a secondary antibodies.

Interpretation of Data and Statistical Analysis

Sera were judged to be positive for antibodies to SQE if two dilutions (i.e., 1:25 and 1:50 dilutions for human serum and 1:50 and 1:100 for mouse serum) had absorbances that were greater than 3 times baseline. Baseline was defined as the absorbance at which the dilution curve became horizontal. Statistical analyses were performed using Minitab Statistical Software, Release 13 and StatXact, Version 5, Cytel Software Corp., Cambridge Mass. Continuous variables were compared using t tests, and categorical data were compared using Pearson's chi-squared tests. To estimate the probability of antibodies to SQE, logistic regression was used to assess the cohort effect adjusted for the possible confounding effects of gender. The between cohort odds ratios for IgG and IgM antibodies to SQE were estimated.

Although the present invention has been described in terms of particular practices making reference to and building upon the teachings of the parent application, it is not limited to those embodiments. Alternative embodiments, practices, examples, and modifications which would still be encompassed by the invention may be made by those skilled in the art, particularly in light of the foregoing teachings.

We claim:

1. A method for detecting the presence of human squalene antibodies capable of specific binding with squalene, comprising the steps of:

providing a solid support suitable for allowing specific binding of squalene with human squalene antibodies;

immobilizing squalene on the solid support;

washing the immobilized squalene with blocking agent;

contacting the immobilized squalene with a sample containing human squalene antibodies or fragments thereof capable of specific binding with squalene;

allowing the squalene antibodies to specifically bind to the immobilized squalene to form a specific antibody complex;

contacting the antibody complex with a ligand that specifically binds to the complex;

contacting the ligand with an indicator agent; and detecting the indicator agent.

* * * * *